(12) United States Patent
Kuniyoshi et al.

(10) Patent No.: US 10,059,734 B2
(45) Date of Patent: Aug. 28, 2018

(54) THIONUCLEOSIDE DERIVATIVE OR SALT THEREOF, AND PHARMACEUTICAL COMPOSITION

(71) Applicant: FUJIFILM Corporation, Tokyo (JP)

(72) Inventors: Hidenobu Kuniyoshi, Ashigarakami-gun (JP); Daisuke Nakagawa, Ashigarakami-gun (JP); Takuya Matsumoto, Ashigarakami-gun (JP); Yuji Yoshimitsu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/581,834

(22) Filed: Apr. 28, 2017

(65) Prior Publication Data

US 2017/0233429 A1 Aug. 17, 2017

Related U.S. Application Data

(63) Continuation of application No. PCT/JP2015/080885, filed on Nov. 2, 2015.

(30) Foreign Application Priority Data

Oct. 31, 2014 (JP) ................................ 2014-222527

(51) Int. Cl.
| | | |
|---|---|---|
| C07H 19/10 | (2006.01) | |
| A61P 35/02 | (2006.01) | |
| A61K 31/7068 | (2006.01) | |
| A61P 35/00 | (2006.01) | |

(52) U.S. Cl.
CPC ......... *C07H 19/10* (2013.01); *A61K 31/7068* (2013.01); *A61P 35/00* (2018.01); *A61P 35/02* (2018.01)

(58) Field of Classification Search
CPC ..... C07H 19/10; A61K 31/7068; A61P 35/00; A61P 35/02
USPC ......................................... 544/317; 514/274
See application file for complete search history.

(56) References Cited

U.S. PATENT DOCUMENTS

| | | | |
|---|---|---|---|
| 3,116,282 A | 12/1963 | Hunter et al. | |
| 3,243,425 A | 3/1966 | Whistler | |
| 4,211,773 A | 7/1980 | Lopez et al. | |
| 4,220,774 A | 9/1980 | Kuehne | |
| 4,803,272 A | 2/1989 | Anton et al. | |
| 5,811,408 A | 9/1998 | Yoshimura et al. | |
| 6,103,707 A | 8/2000 | Yamada et al. | |
| 6,147,058 A | 11/2000 | Yoshimura et al. | |
| 6,448,415 B1 | 9/2002 | Lee et al. | |
| 7,148,223 B2 | 12/2006 | Secrist, III et al. | |
| 7,285,572 B2 * | 10/2007 | Shinagawa | C07C 217/28 |
| | | | 514/529 |
| 7,858,788 B2 * | 12/2010 | Yoshida | C07F 9/6561 |
| | | | 544/117 |
| 8,329,925 B2 | 12/2012 | Voigtlander et al. | |
| 8,420,831 B2 | 4/2013 | Voigtlander et al. | |
| 9,221,865 B2 | 12/2015 | Nakamura et al. | |
| 9,475,835 B2 | 10/2016 | Nakamura et al. | |
| 2003/0124054 A1 | 7/2003 | Toyohara et al. | |
| 2005/0129611 A1 | 6/2005 | Toyohara et al. | |
| 2006/0142238 A1 | 6/2006 | McGuigan | |
| 2009/0069263 A1 | 3/2009 | Damha et al. | |
| 2013/0252918 A1 | 9/2013 | McGuigan | |
| 2015/0011499 A1 | 1/2015 | Baba | |
| 2016/0355497 A1 | 12/2016 | Takeda et al. | |

(Continued)

FOREIGN PATENT DOCUMENTS

| | | |
|---|---|---|
| CN | 101058557 A | 10/2007 |
| CN | 101200463 A | 6/2008 |

(Continued)

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak R Rao
(74) *Attorney, Agent, or Firm* — Sughrue Mion, PLLC

(57) ABSTRACT

Disclosed are a compound and a pharmaceutical composition that exhibit an excellent drug efficacy against a tumor, in particular a tumor which has acquired resistance to gemcitabine. Specifically, provided is a thionucleoside derivative represented by General Formula [1]

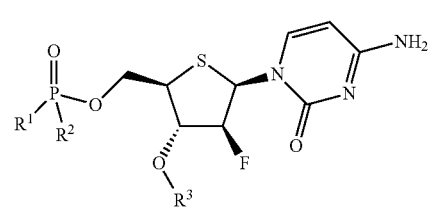

(in the formula, $R^1$ represents a hydroxyl group which may be protected, a $C_{1-20}$ alkoxy group which may be substituted, or the like; $R^2$ represents a $C_{1-20}$ alkoxy group which may be substituted, a $C_{3-8}$ cycloalkoxy group which may be substituted, or the like; and $R^3$ represents a hydrogen atom or the like); or a salt thereof. Further, provided is a pharmaceutical composition containing such a thionucleoside derivative or a salt thereof.

16 Claims, No Drawings

(56) References Cited

U.S. PATENT DOCUMENTS

| | | | |
|---|---|---|---|
| 2016/0355536 | A1 | 12/2016 | Ito et al. |
| 2016/0362389 | A1 | 12/2016 | Nakamura et al. |

FOREIGN PATENT DOCUMENTS

| | | | |
|---|---|---|---|
| CN | 101880287 A | 11/2010 | |
| EP | 0 841 344 A1 | 5/1998 | |
| EP | 2 883 866 A1 | 6/2015 | |
| JP | 53-119810 A | 10/1978 | |
| JP | 55-49395 A | 4/1980 | |
| JP | 56-92239 A | 7/1981 | |
| JP | 5/178875 A | 7/1993 | |
| JP | 6-501261 A | 2/1994 | |
| JP | 8-53490 A | 2/1996 | |
| JP | 8-504753 A | 5/1996 | |
| JP | 10-282039 A | 10/1998 | |
| JP | 2003-172990 A | 6/2003 | |
| JP | 2005-503358 A | 2/2005 | |
| JP | 2006-335737 A | 12/2006 | |
| JP | 2006-528162 A | 12/2006 | |
| JP | 2007-514643 A | 6/2007 | |
| JP | 4202327 B2 | 12/2008 | |
| JP | 2009-538829 A | 11/2009 | |
| JP | 2010-59173 A | 3/2010 | |
| JP | 4719356 B2 | 7/2011 | |
| JP | 2011-526242 A | 10/2011 | |
| JP | 2013-514260 A | 4/2013 | |
| JP | 2013/146833 A1 | 10/2013 | |
| JP | 2013-540129 A | 10/2013 | |
| JP | 2014/027658 A1 | 2/2014 | |
| WO | 91/04982 A1 | 4/1991 | |
| WO | 94/05687 A1 | 3/1994 | |
| WO | 96/01834 A1 | 1/1996 | |
| WO | 97/37993 A1 | 10/1997 | |
| WO | 97/038001 A1 | 10/1997 | |
| WO | 97/49716 A1 | 12/1997 | |
| WO | 99/28312 A2 | 6/1999 | |
| WO | 99/43690 A1 | 9/1999 | |
| WO | 02/058740 A1 | 8/2002 | |
| WO | 03/000200 A2 | 1/2003 | |
| WO | 2004/014930 A1 | 2/2004 | |
| WO | 2004/014931 A1 | 2/2004 | |
| WO | 2004/027658 A1 | 4/2004 | |
| WO | 2004/100891 A2 | 11/2004 | |
| WO | 2004/106352 A1 | 12/2004 | |
| WO | 2005/012327 A2 | 2/2005 | |
| WO | 2006/073197 A1 | 7/2006 | |
| WO | 2007/056596 A2 | 5/2007 | |
| WO | 2007/068113 A1 | 6/2007 | |
| WO | 2007/130783 A2 | 11/2007 | |
| WO | 2011/074484 A1 | 6/2011 | |
| WO | 2012/045999 A1 | 4/2012 | |
| WO | 2016/155593 A1 | 10/2016 | |

OTHER PUBLICATIONS

Simone, Oncology: Introduction, Cecil Textbook of Medicine, 20th Edition, vol. 1, pp. 1004-101 O, 1995.*

Jeong, et al., The Stereochemical Outcome of the DAST Fluorination of 4'-Thipyrimidine Nucleosides with "Up" Hydroxyl Groups is Controlled by the Oxidation State of the Sulfur Atom, Chemistry Letters, pp. 301-302, 1995. (2 pages total).

Jeong, et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572, 1994. (4 pages total).

Jeong, et al., Facile Fluorination of Deoxy-4'-thiopyrimidine Nucleosides with "Down" Hydroxyl Groups. Retention of Configuration After Fluoride Opening of the Quartenized N3-MEM Anhydronucleosides, Tetrahedron Letters, vol. 35, No. 41, pp. 7573-7576,1994. (4 pages total).

Yoshimura, et al., Synthesis of 2'-deoxy-2'-fluoro-4'-thioarabinonucleosides as potential antitumor antiviral agents from D-glucose, Nucleic Acids Symeosium Series, No. 35, pp. 15-16, 1996. (2 pages total).

Yoshimura, et al., A Novel Synthesis of New Antineoplastic 2'-Deoxy-2'-substituted -4'-thiocytidines, Journal of Organic Chemistry, vol. 61, No. 3, pp. 822-823, 1996. (2 pages total).

Tann, et al., Fluorocarbohydrates in Synthesis. An Efficient Synthesis of 1-(2-Deoxy-2-fluoro-β-D-arabino-furanosyl)-5-iodouracil (β-FIAU) and 1-(2-Deoxy-2-fluoro-β-D-arabinofuranosyl) thymine (β-FMAU), Journal of Organic Chemistry, American Chemical Society, vol. 50, No. 19, 1985. pp. 3644-3647 (4 pages total).

Jeong, et al., Participation of sulfur occurred during the Mitsunobu reaction: synthesis of novel isodideoxythionucleosides, J. Chem. Soc., Perkin Trans. 1, pp. 3325-3326, 1998. (2 pages total).

Office Action dated May 12, 1999, which issued during the prosecution of U.S. Appl. No. 08/973,529 (now U.S. Pat. No. 6,147,058).

Office Action dated Apr. 26, 2017, issued from the Mexican Patent Office in Mexican Patent Application No. MX/a/2014/011182.

Office Action dated May 19, 2017, issued from the Europe Patent Office in European Patent Application No. 13770090.2.

Notices of Allowance and Allowability dated Nov. 8, 1999, which issued during the prosecution of U.S. Appl. No. 08/973,529 (now U.S. Pat. No. 6,147,058).

Office Action dated May 8, 2017, from the European Patent Office in European Application No. 13879640.4.

Attardo, G., et al., "Efficient Synthesis of 5,8-Disubstituted-1,4-Dihydrobenzoxathiin-3-Oxides and Their Isomeric Structures, 4,7-Disubstituted-1,3-Dihydrobenzo[b] Thiophene-2,2-Dioxides", Tetrahedron Letters, vol. 35, No. 27, 1994, pp. 4743-4746 (4 pages).

International Preliminary Report on Patentability and Translation of Written Opinion, dated May 11, 2017, from the International Bureau in counterpart International Application No. PCT/JP2015/080885.

William Plunkett et al., "Preclinical characteristics of gemcitabine", Anti-Cancer Drugs, 1995, pp. 7-13, vol. 6, Suppl. 6.

Larry W. Hertel et al., "Evaluation of the Antitumor Activity of Gemcitabine (2',2'-Difluoro-2'-deoxycytidine)", Cancer Research, Jul. 15, 1990, pp. 4417-4422, vol. 50.

Hayato Fujita et al., "Gene Expression Levels as Predictive Markers of Outcome in Pancreatic Cancer after Gemcitabine-Based Adjuvant Chemotherapyl,2", NEO Plasia, Oct. 2010, pp. 807-817, vol. 12, No. 10.

Magdalena Slusarczyk et al., "Application of ProTide Technology to Gemcitabine: A Successful Approach to Overcome the Key Cancer Resistance Mechanisms Leads to a New Agent (NUC-1031) in Clinical Development", J. Med. Chem, 2014, pp. 1531-1542, vol. 57, No. 4.

Hyunah Choo et al., "Synthesis, Anti-HIV Activity, and Molecular Mechanism of Drug Resistance of L-2',3'-Didehydro-2',3'-dideoxy-2'-fluoro-4'-thionucleosides", J. Med. Chem., 2003, pp. 389-398, vol. 46, No. 3.

A. G. Cottrell et al., "Reaction of Sugar Chlorosulfates VII. Some Conformational Aspects", Canadian Journal of Chemistry, Jul. 1, 1966, pp. 1483-1491, vol. 44, No. 13.

Johan Fanton e al., "Enzymatic and Organocatalyzed Asymmetric Aldolization Reactions for the Synthesis of Thiosugar Scaffolds", European Journal of Organic Chemistry, 2012, pp. 203-210.

International Preliminary Report on Patentability and Written Opinion of the international Searching Authority (forms PCT/IB388, PCT/373, PCT/ISA 237 and PCT/IB/326), dated Feb. 26, 2015, for International Application No. PCT/JP2013/071871.

International Search Report for PCT/JP2013/071871, dated Nov. 26, 2013.

Laetitia Jean-Baptise et al., "Synthesis of 2',3'-Dideoxy-2'-Fluoro-4'-Thionucleosides from a Fluoroxanthate", Synlett, 2008, pp. 817-820, No. 6.

Masajiro Kawana et al., "The Synthesis of 2',3'-Diodexycytidene and Its 2'-Azido Analogue Applications of the Deoxygenative [1,2]-Hydride Shift of Sulfonates with Mg(OMe)2-NaBH4", The Chemical Society of Japan, Chemistry Letters, 1987, pp. 2419-2422.

(56) References Cited

OTHER PUBLICATIONS

Naveen K. Khare et al., "Synthesis of 4-deoxy-4-thioarabinofuranosyl disaccharides, analogs of Mycobactrial arabinoglactan", Indian Journal of Chemistry, Nov. 2008, pp. 1748-1752, vol. 47B.
Office Action issued in U.S. Appl. No. 14/621,119, dated Mar. 24, 2015.
N. Ototani et al., "Preparation and Antitumor Activity of 4'-Thio Analogs of 2,2'-Anhydro-1-β-D-arabinofuranosylcytosine", Journal of Medicinal Chemistry, 1974, pp. 535-537, vol. 17, No. 5.
Wu-Bao Wang et al., "A Practical Synthesis of Sugar-Derived Cyclic Nitrones: Powerful Synthons for the Synthesis of Iminosugars", Synlett, 2010, pp. 488-492, No. 3.
Yuichi Yoshimura et al., "An Alternative Synthesis of the Anthineoplastic Nucleoside 4'-ThioFAC and Its Application to the Synthesis of 4'-ThionFAG and 4'-Thiocytarazid", J. Org. Chem., 1999, pp. 7912-7920, vol. 64, No. 21.
Australian Office Action for Application No. 2013303534, dated Dec. 1, 2015.
Official Action for Canadian Patent Application No. 2,880,794, dated Nov. 2, 2015.
Chinese Office Action for Application No. 201380042642.1, dated Nov. 2, 2015.
Extended European Search Report for Application No. 13879640.4 dated May 18, 2016.
Japanese Office Action for Application No. 2014-530560 dated Mar. 1, 2016.
Korean Office Action for Application No. 10-2015-7003655, dated May 12, 2016.
Office Action issued in U.S. Appl. No. 14/873,966, dated Feb. 8, 2016.
Notice of Allowance issued in U.S. Appl. No. 14/873,966, dated May 26, 2016.
Partial Supplementary European Search Report issued in European Application No. 13879640.4, dated Feb. 16, 2016.
Russian Office Action for Application No. 2015108790, dated Apr. 25, 2016.
Supplemental Notice of Allowance issued in U.S. Appl. No. 14/873,966, dated Jul. 6, 2016.
Karmal N. Tiwari et al., "Synthesis and Biological Activity of 4'-Thio-L-Xylofuranosyl Nuclesides", Nucleosides, Nucleotides & Nucleic Acids, 2001, pp. 743-746, vol. 20, Nos. 4-7.
Yuichi Yoshimura et al., "Synthetic Studies on 2'-Substituted-4'-Thiocytidine Derivatives As Antineoplastic Agents", Nucleosides & Nucleotides, 1999, pp. 815-820, vol. 18, Nos. 4&5.
Official Action issued in Canadian Patent Application No. 2,880,794, dated Aug. 18, 2016.
Notice of Final Rejection issued in Korean Patent Application No. 10-2015-7003655, dated Nov. 21, 2016.
Official Action issued in Korean Patent Application No. 10-2015-7003655, dated Jan. 11, 2017.
Feng Zheng et al., "Synthesis of L-β-3'Deoxy-2',3'-difluoro-4'-thionucleosides", Organic Letters, 2006, pp. 6083-6086, vol. 8, No. 26.
Official Action issued in Russian Patent Application No. 2015108790, dated Dec. 29, 2016.
Official Action issued in Chinese Patent Application No. 201380042642.1, dated Jan. 16, 2017.
Extended European Search Report issued in European Patent Application No. 17150141.4, dated Mar. 16, 2017.
David Baker et al., "Large-scale preparation of D-allose: observations on the stereoselectivity of the reduction of 1,2:5,6-di-O-isopropylidene-α-D-ribo-hexofuranos-3-ulose hydrate", Carbohydrate Research, 1972, pp. 192-197, vol. 24.
Lak Shin Jeong et al., "N6-Substituted D-4'-Thioadenosine-5'-methyluronamides: Potent and Selective Agonists at the Human A3 Adenosine Receptor", J. Med. Chem., 2003, pp. 3775-3777, vol. 46, No. 18.
Takashi Komine et al., "Synthesis and Structure-Activity Relationship Studies of Highly Potent Novel Oxzolidinone Antibacterials", J. Med. Chem., 2008, pp. 6558-6562, vol. 51, No. 20.
Shinji Miura et al., "Antitumor activity of a novel orally effective nucleoside, 1-(2-deoxy-2-fluoro-4-thio-B-D-arabinofuranosyl) cytosine", Cancer Letters, 1998, pp. 103-110, vol. 129.
Shinji Miura et al., "Comparison of 1-(2-deoxy-2fluoro-4-thio-β-D-arabinofuranosyl)cytosine with gemcitabine in its antitumor activity", Cancer Letters, 1999, pp. 177-182, vol. 144.
Koen Vanhessche et al., "L-Ribulose A: Novel Chiral Pool Compound", Tetrahedron Letters, pp. 2337-2340, 1990, vol. 31, No. 16.
Oscar Varela et al., "First Synthesis of Aldopentono-1,4-thiolactones", J. Org. Chem., 1993, pp. 7860-7864, vol. 58 No. 27.
Chia-Lin J. Wang et al., "Synthesis of 2'(S), 3'(R), 5'-Trihydroxypentyladenine", Tetrahedron Letters, 1988, pp. 1107-1110, vol. 29, No. 10.
Jonathan K. Watts et al., Synthesis and Conformal Analysis of 2'-Fluoro-5-methyl-4'-thioarabinouridine (4'S-FAMAU), J. Org. Chem., 2006, pp. 921-925, vol. 71.
Yuichi Yoshimura et al., "A Novel Synthesis of 2'-Modified 2'-Deoxy-4'-thocytidines from D-Glucose1", J. Org. Chem., 1997, pp. 3140-3152, vol. 62, No. 10.
Yuichi Yoshimura et al., "An alternative synthesis of antineoplastic nucleoside 4'-thioFAC", Nucleic Acids Symposium Series, 1998, pp. 11-12, No. 39.
Yuichi Yoshimura et al., "An Alternative Synthesis of Antineoplastic 4'-Thiocytidine Analogue 4'-ThioFAC", Tetrahedron Letters, 1999, pp. 1937-1940, vol. 40.
Yuichi Yoshimura e al., "Synthesis and Biological Activities of 2'-Deoxy-2'fluoro-4'thioarabinofuranosylpyrimidine and -Purine Nucleosides", Bioorganic & Medicinal Chemistry, 2000, pp. 1545-1558, vol. 8.
Deborah A. Zajchowski et al., "Anti-tumor efficacy of the nucleoside analog 1-(-deoxy-2-fluoro-4-thio-(β-D-arabinofuranosyl) cytosine (4'-thio-FAC) on human pancreatic and ovarian tumor xenograft models", Int. J. Cancer, 2005, pp. 1002-1009, vol. 114.
Partial European Search Report issued in European Patent Application No. 10163406.1, dated Nov. 24, 2010.
PCT International Preliminary Report on Patentability (IPRP), dated Jun. 19, 2012 for PCT International Application No. PCT/JP2010/072182.
International Search Report and Written Opinion for PCT/JP2010/072182, dated Apr. 29, 2011.
Thomas B. Mercer et al., Looking glass inhibitors: both enantiomeric N-benzyl derivatives of 1,4-dideoxy-1,4-imino-D-lyxitol [a potent competitive inhibitor of a-D-glactosidase ] and of 1-4-dideoxy-1,4-imino-L-lyxitol [a weak competitive inhibitor of a-D-glactosidase] inhibit naringinase, an α-L-rhamnosidase competitively, Tetrahedron: Asymmetry, 2009, pp. 2368-2373, vol. 20, No. 20.
Paul Karrer, "Organic Chemistry", 2nd Edition, Elsevier Publ. Comp., Inc. NY, 1946, pp. 92-102.
Shinji Miura et al., "Potent antitumor effect of 1-(2-deoxy-2-fluoro-4-thio-B-D-arabinofuransoyl)cytosine on peritoneal dissemination models of gastrointestinal cancers", Oncology Reports, 2002, pp. 1319-1322, vol. 9, No. 6.
International Search Report and Written Opinion for PCT/JP2013/058896, dated Jun. 4, 2013.
International Preliminary Report on Patentability, dated Oct. 9, 2014, from the International Bureau of WIPO in Application No. PCT/JP2013/058896.
Official Action issued in Singapore Patent Application No. 11201406080V, dated Mar. 19, 2015.
Official Action issued in New Zealand Patent Application No. 701245, dated Jan. 28, 2015.
Official Action issued in Japanese Patent Application No. 2014-507938, dated Apr. 7, 2015.
Official Action issued in New Zealand Patent Application No. 701245, dated Aug. 21, 2015.

(56) References Cited

OTHER PUBLICATIONS

Mayumi Takahashi et al., "Synthesis and crystal structure of 20-deoxy-20-fluoro-40-thioribonucleosides: substrates for the synthesis of novel modified RNAs", Tetrahedron, 2008, pp. 4313-4324, vol. 64.
Official Action issued in Chinese Patent Application No. 201380016308.9, dated Jul. 1, 2015.
Official Action issued in Australian Patent Application No. 2013241341, dated Oct. 5, 2015.
Extended European Search Report issued in European Patent Application No. 13770090.2, dated Oct. 12, 2015.
Official Action issued in Russian Patent Application No. 2014143277/04, dated Nov. 5, 2015.
Official Action issued in Canadian Patent Application No. 2,865,742, dated Mar. 29, 2016.
Official Action issued in Russian Patent Application No. 2014143277/04, dated Mar. 21, 2016.
Official Action issued in Taiwanese Patent Application No. 102110915, dated May 25, 2016.
Stephen M. Berge et al., "Pharmaceutical Salts", Journal of Pharmaceutical Sciences, Jan. 1977, pp. 1-19, vol. 66, No. 1.
Abu T.M. Serajuddin, "Salt formation to improve drug solubility", Advanced Drug Delivery Reviews, 2007, pp. 603-616, vol. 59, No. 7.
Official Action issued in Israeli Patent Application No. 23422, dated Sep. 13, 2016.
Official Action issued in Taiwanese Patent Application No. 102110915, dated Sep. 30, 2016.
Official Action issued in Korean Patent Application No. 10-2014-7030209, dated Oct. 25, 2016.
Notice of Final Rejection issued in Korean Patent Application No. 10-2014-7030209, dated Apr. 3, 2017.
International Search Report for PCT/JP2015/080885, dated Feb. 2, 2016.
Written Opinion for PCT/JP2015/080885, dated Feb. 2, 2016.
Jeong et al., Chemistry Letters, pp. 301-302, 1995.
Jeong et al., Tetrahedron Letters, 35(41):7569-7572, 1994.
Jeong et al., Tetrahedron Letters, 35(41):7573-7576, 1994.
Y. Yoshimura et al., Nucleic Acids Symposium Series, No. 35, pp. 15-16 (1996).
Y. Yoshimura et al., Journal of Organic Chemistry, vol. 61, No. 3, pp. 822-823 (1996).
Notice of Allowance dated Feb. 15, 2017 in U.S. Appl. No. 14/498,334.
Office Action dated Aug. 11, 2016 in U.S. Appl. No. 14/498,334.
Office Action dated Nov. 8, 2012 in U.S. Appl. No. 13/606,746 (now U.S. Pat. No. 8,420,831).
Notice of Allowance dated Aug. 30, 2012 in U.S. Appl. No. 12/959,735 (now U.S. Pat. No. 8,329,925).
Office Action dated Mar. 13, 2017 in U.S. Appl. No. 15/238,784.
Zheng, F., et al., "Synthesis of L-β-3'-Deoxy-3',3'difluoro-4'-thionucleosides", Organic Letters, vol. 8, No. 26, pp. 6083-6086, 2006 (4 pages total).
Office Action dated May 19, 2017, issued from the Canadian Patent Office in Canadian Patent Application No. 2,880,794.
Office Action dated Sep. 26, 2017 from the Japanese Patent Office in Japanese Application No. 2016-136575.
Raoul, S., et al "$^{1}$H, $^{13}$C and $^{15}$N Nuclear magnetic resonance analysis and chemical features of the two main radical oxidation products of 2'-deoxyguanosine: oxazolone and imidazolone nucleosides", J. Chemical Soc., Perkin Trans. 2, 1996, Issue 3, pp. 371-381 (11 pages).
International Preliminary Report on Patentability, dated Oct. 9, 2014, from the International Bureau of WIPO in International Application No. PCT/JP2013/058896.
Communication dated Apr. 4, 2017 from the Japanese Patent Office in Japanese Application No. 2014-029978.
Communication dated Mar. 28, 2017 from the European Patent Office in European Application No. 15751531.3.
Communication dated Mar. 13, 2017 from the U.S. Patent and Trademark Office in U.S. Appl. No. 15/238,232.
Communication dated Apr. 18, 2017 from the Japanese Patent Office in Japanese Application No. 2016-504110.
Communication dated Jan. 31, 2017 from the European Patent Office in European Application No. 15751503.2.
Communication dated Jul. 2, 2015 from the U.S. Patent and Trademark Office in U.S. Appl. No. 14/621,119.
Communication dated Nov. 30, 2015 from the U.S. Patent and Trademark Office in U.S. Appl. No. 14/621,119.
Communication dated Sep. 12, 2016 from the U.S. Patent and Trademark Office in U.S. Appl. No. 14/873,966.
Vorbruggen et al., Org. Reactions (2000), pp. 55.
Watts et al., Nuclei. Acids Res. (2007) vol. 35(5), pp. 1441-1451.
Karrer, Org Chem. 2nd Ed. (1996). pp. 92-102.
Kamal N. Tiwari et al., "The Synthesis and Biological Activity of 1-(2-Deoxy 4-Thio-a-L-Threo-Pentofuranosyl) Thymine", Nucleosides & Nucleotides, 12(8), pp. 841-846 (1993).
Hiroshi Satoh et al., "Synthesis of L-Enantiomers of 4'-Thioarabinofuranosyl Pyrimidine Nucleosides", Bioorganic & Medicinal Chemistry Letters 8 (1998) pp. 989-992.
Yuichi Yoshimura et al., "A Facile, Alternative Synthesis of 4'-Thloarabinonucleosides and their Biological Activities", J. Med. Chem. 1997, 40(14); pp. 2177-2183.
Yun-Lung Fu et al., "An Alternative Synthesis of Anomeric Methyl 2-Deoxy-4-thio-D-erythro-pentofuranosides", J. Org. Chem., vol. 41, No. 24; 1976, pp. 3831-3834 (4 pages total).
John A. Secrist III et al., "Synthesis and Biological Activity of 2'-Deoxy-4'-thio Pryimidine Nucleosides", J. Med. Chem. 1991, 34, No. 8 (pp. 2361-2366).
International Search Report, issued by International Searching Authority on May 19, 2015, in International Application No. PCT/JP2015/054305.
Martin W. Bredenkamp et al., "Stannylene Directed Selective Acylation of Some Open-Chain L-Arabinose Derivatives", Tetrahedron Letters, 1990, 31(19) pp. 2759-2762.
Elmer J. Reist et al., "Thio Sugars, Synthesis of the Adenine Nucleosides of 4-Thio-D-Xylose and 4-Thio-D-Arabinose", Journal of Organic Chemistry, 1968, 33(1) pp. 189-192.
Elmer J. Reist et al., "Synthesis the 4-Thio-D-and-L-Ribofuranose and the Corresponding Adenine Nucleosides", Journal of the American Chemical Society, 1964, 86(24), pp. 5658-5663.
Stephanie A. Hartsel et al., "Synthesis of 9-(4-Thioxylofuranosyl) adenine via a Novel Glycosylation Reaction", Tetrahedron Letters 39 (1998) pp. 205-208.
Vjera Pejanovic et al., "Synthesis and Biological Evaluation of Some Novel 4'-Thio-L-ribonucleosides with Modified Nucleobase Moieties", Bioorganic & Medicinal Chemistry Letters, 2003, 13(11) pp. 1849-1852.
Kamal N. Tiwari et al., "Synthesis and Anti-cancer Activity of Some Novel 5-Azacytosine Nucleosides", Nucleosides, Nucleotides & Nucleic Acids, 2003, 22(12), pp. 2161-2170.
International Preliminary Report on Patentability issued from the International Bureau in International Application No. PCT/JP2015/054305, dated Jan. 4, 2016.
Peter Haeberli et al., "Syntheses of 4'-thioribonucleosides and thermodynamic stability and crystal structure of RNA oligomers with incorporated 4'-thiocytosine", Nucleic Acids Research, 2005, vol. 33 No. 13; pp. 3965-3975.
G. Inguaggiato et al., "Novel Triazole 2'-Deoxy-4'-Thionucleosides: Stereoselective Synthesis and Biological Evaluation", Nucleosides & Nucleotides, 1999; vol. 18 No. 3; pp. 457-467.
Houssine Ait-sir et al, "Synthesis and configurational assignments of 3-substituted 2-deoxy-4-thio-Derythro-pentofuranose derivatives", Journal of the Chemical Society, Perkin transactions 1, 1996; No. 14; pp. 1665-1671.
Miura et al., "Suppression of Peritoneal Dissemination by 4'-thio-FAC," Oncology Reports, vol. 9, No. 6, Nov.-Dec. 2002, pp. 1319-1322 (9 pages total).
King, "Bioisosteres, Conformational Restriction, and Pro-drugs—Case History: An Example of a Conformational Restriction Approach", Med. Chem., Principle and Practice (1994), pp. 206-208.

(56) References Cited

OTHER PUBLICATIONS

Communication dated Dec. 22, 2016, from the European Patent Office in European Application No. 15751531.3.
Cox, J.M., et al., "Cyclic Hemithioacetals: Analogues of Thiosugars with Sulphur in the Ring", J. Chem. Soc., Section C, 1967, pp. 1130-1134.
International Search Report, issued by International Searching Authority in corresponding International Application No. PCT/JP2015/052304, dated Mar. 10, 2015.
Hua Lin et al., "Highly Efficient Asymmetric Synthesis of Enantiopure Dihydro-1, 2-oxazines: Dual-Organocatalyst-Promoted Asymmetric Cascade Reaction", Organic Letters (2012), vol. 14, No. 15; pp. 3818-3821.
David A. Berges et al., "Bicyclic diazasugars. Part 3: β-D-Mannose and 6 deoxy β-L-gulose analogues", Tetrahedron, 2001, vol. 57; pp. 9915-9924.
Ronald C. Horton Jr. et al, "Aldehyde-Terminated Self-Assembled Monolayers on Gold: Immobilization of Amines onto Gold Surfaces", J. Am. Chem. Soc., 1997, vol. 119; pp. 12980-12981.
H. Driguez et al., "A Novel Synthesis of 5-Thio-D-Glucose", Tetrahedron Letters, 1981, vol. 22, No. 50, pp. 5061-5062.
R. M. Rowell et al., "Derivatives of a-D-Glucothiopyranose", J. Org. Chem., 1996, vol. 31; pp. 1514-1516.
Eva Bozo et al., "Synthesis of 4-cyrophenyl and 4-nitrophenyl 1,5-dithio-L-and -D-arabinopyranosides possessing antithrombotic activity[1,2]", Carbohydrate Research 1998, vol. 311; pp. 191-202.
International Preliminary Report on Patentability issued from the International Bureau in International Application No. PCT/JP2015/052304, dated Feb. 16, 2016.
Johan Fanton et al, "Enzymatic and Organocatalyzed Asymmetric Aldolization Reactions for the Synthesis of Thiosugar Scaffolds", Eur. Journal Org. Chem. 2012, pp. 203-210.
Junji Fujita et al., "Synthesis of thiosaccharides employing the Pummerer rearrangement of tetrahydrothiopyran oxides", Tetrahedron 2004, vol. 60, No. 32, pp. 6829-6851.
Dusan Miljkovic et al., "An improved synthesis of methyl 5-thio-D-arabino-pyranosides", Journal of the Serbian Chemical Society, vol. 55, 1990; pp. 359-361.
Hironobu Hashimoto et al., "Novel conversion of aldopyranosides into 5-thioaldopyranosides via acyclic monothioacetals with inversion and retention of configuration at C-5", Carbohydrate Research, vol. 282, Issue 2 (Feb. 23, 1996) pp. 207-221.
Communication dated Jun. 14, 2017 from the State of Israel Patent Office in Israeli Application No. 237086.
Office Action dated Oct. 27, 2017, from Intellectual Property India in Indian Patent Application No. 6251/CHENP/2012.
Office Action in Taiwanese Application No. 99142198 dated Sep. 11, 2014.
Office Action in Australian Application No. 2010331367 dated Jul. 25, 2016.
Office Action in Canadian Application No. 2,784,399 dated Oct. 6, 2016.
Office Action in European Application No. 10801279.0 dated Jun. 4, 2013.
Office Action in European Application No. 10801279.0 dated Dec. 16, 2013.
Extended European Search Report (EESR) issued in European Application No. 14177042.0 dated Oct. 2, 2014.
Office Action in European Application No. 14177042.0 dated Aug. 19, 2015.
Office Action in Korean Application No. 10-2012-7018741 dated Dec. 1, 2016.
Office Action in Russian Application No. 2012130422 dated Jan. 22, 2015 .

Office Action in Singapore Application No. 2012044368 dated Jun. 11, 2014.
Office Action in Vietnamese Application No. 1-2012-02041 dated Jul. 4, 2013.
Office Action in Vietnamese Application No. 1-2012-02041 dated Mar. 7, 2014.
Office Action in Chinese Application No. 201380042642.1 dated Aug. 2, 2017.
Extended European Search Report (EESR) issued in European Application No. 15853887.6 dated Aug. 17, 2017.
Watt et al., "Synthesis and Conformational Analysis of 2'-Fluoro-5-methy 1-4'-thioarabinouridine (4'-SFMAU)", Journal of Organic Chemistry, vol. 71, No. 3, Jan. 22, 2006, pp. 921-925, XP002606716.
J. Allen Miter et al., "2,2'-Anhydro-4'-Thionucleosides: Precursors for 2'-Azido- and 2'-Chloro-4'thionucleosides and for a Novel Thiolane to Thietane Rearrangement", Nucleosides, Nucleotides and Nucleic Acids, vol. 19, No. 9, Sep. 24, 2000, pp. 1475-1486, XP055207502.
Corrected Notice of Allowability dated Nov. 17, 2017 from the United States Patent and Trademark Office in U.S. Appl. No. 14/498,334.
Office Action dated Jan. 23, 2018 from the Japanese Patent Office in counterpart Japanese Application No. 2016-556227.
Office Action dated Mar. 22, 2018, issued by the Korean Intellectual Property Office in Korean Application No. 10-2017-7018337.
Office Action dated Mar. 27, 2018 from the Intellectual Properly Office of India in Indian Application No. 1391/CHENP/2015.
Kawana et al, "The Synthesis of 2',3'-Dideoxycytidine and Its 2'-Azldo Analogue. Applications of the Deoxygenative [1,2]-Hydride Shift of Sulfonates with Mg(OMe)$_2$-NaBH$_4$", Chemistry Letters, Sep. 19, 1987, pp. 2419-2422(4 pages total).
Khare et al, "Synthesis of 4-deoxy-4-thioarabinofuranosyl disaccharides, analogs of Mycobacterial arabinogalactan", Indian Journal of Chemistry, Nov. 2008, vol. 47B, pp. 1748-1752 (5 pages total).
Cottrell et al, "Reactions of Sugar Chlorosulfates", Canadian Journal of Chemistry, Jul. 1, 1966, vol. 44, No. 13, pp. 1483-1491 (9 pages total).
Zheng et al, "Synthesis of L-β-3'-Deoxy-3',3'-difluoro-4'-thionucleosides", Organic Letters, Oct. 19, 2006, vol. 8, No. 26, pp. 6083-6086(4 pages total).
Jean-Baptiste et al, "Synthesis of 2',3'-Dideoxy-2'-Fluoro-4'-Thionucleosides from a Fluoroxanthate", Synlett, Jan. 8, 2008, No. 6, pp. 817-820 (5 pages total).
Yoshimura et al, "An Alternative Synthesis of the Antineoplastic Nucleoside 4'-ThioFAC and Its Application to the Synthesis of 4'-ThioFAG and 4'-Thiocytarazid", J.Org Chem., vol. 64, Jun. 14, 1999, pp. 7912-7920 (9 pages total).
Ototani et al., "Preparation and Antitumor Activity of 4'-Thio Analogs of 2,2'-Anhydro-1-β-D-arabinofuranosylcytosine," Journal of Medicinal Chemistry, 1974, vol. 17, No. 5, pp. 535-537 (3 pages total).
Wang et al, "A Practical Synthesis of Sugar-Derived Cyclic Nitrones: Powerful Synthons for the Synthesis of Iminosugars", SYNLETT, 2010, No. 3, pp. 488-492 (5 pages total).
Office Action dated Apr. 12, 2018 from the Canadian Patent Office in counterpart Canadian Application No. 2966138.
Office Action dated Apr. 28, 2018 from the Russian Patent Office in counterpart Russian Application No. 2017114338/04.
Zefirova, O.N., et al., "On history of emergence and development of bioisoterism concept", Moscow University Herald, Series 2, Chemistry, 2002, T. 43, No. 4, pp. 251-256 (6 pages).
Communication dated Jul. 3, 2018 issued by the European Patent Office in European Patent Application No. 17150141.4.
Communication dated May 30, 2018 issued by the Intellectual Property Office of Indonesia in Application No. W00201202819.

* cited by examiner

THIONUCLEOSIDE DERIVATIVE OR SALT THEREOF, AND PHARMACEUTICAL COMPOSITION

CROSS-REFERENCE TO RELATED APPLICATIONS

The present application is a continuation of PCT/JP2015/080885 filed on Nov. 2, 2015 and claims priorities under 35 U.S.C. § 119 of JP Patent Application No. 2014-222527 filed on Oct. 31, 2014.

BACKGROUND OF THE INVENTION

1. Field of the Invention

The present invention relates to a thionucleoside derivative or a salt thereof which is useful as a tumor treatment agent and a pharmaceutical composition.

2. Description of the Related Art

It has been known that 1-(2-deoxy-2-fluoro-4-thio-β-D-arabinofuranosyl) cytosine (hereinafter, also referred to as compound A), which is a thionucleoside, has an excellent antitumor action and is useful in the treatment of malignant tumors (for example, lung cancer, esophageal cancer, stomach cancer, colon cancer, rectal cancer, pancreatic cancer, breast cancer, renal cancer, bladder cancer, uterine cancer, osteosarcoma, and melanoma) and the like (WO1997/038001A).

On the other hand, it has been known that gemcitabine (2',2'-difluoro-2'-deoxycytidine), which is a nucleoside, is effective against cancerous tumors such as the large intestine, lung, pancreas, breast, bladder and ovarian tumors (Cancer Research, Vol. 50, pp 4417 to 4422, 1990 and Anti-Cancer Drugs, Vol. 6, pp 7 to 13, 1995). Gemcitabine has become a standard chemotherapy of pancreatic cancer after receiving the FDA approval in 1996 and has also recently received an approval for use in the treatment of non-small cell lung cancer, ovarian cancer, bladder cancer, and breast cancer.

In this regard, congenital or acquired resistance to nucleoside analogues (for example, gemcitabine, 5-fluorouracil, cytarabine, and fludarabine) is a common problem in cancer therapy and is considered as an important cause of a low patient survival rate. Like other nucleoside analogues, gemcitabine is also faced with many problems of congenital or acquired drug resistance (Journal of Medicinal Chemistry, Vol. 57, pp 1531 to 1542, 2014). It has been reported that acquisition of the resistance to gemcitabine by tumor cells results in a decreased overall survival time of cancer patients (Neoplasia, Vol. 12, pp 807 to 817, 2010).

To overcome the resistance to gemcitabine, the development of new drugs based on resistance mechanisms has been carried out and for example, a compound obtained by adding an amide phosphite ester to gemcitabine is known (Journal of Medicinal Chemistry, Vol. 57, pp 1531 to 1542, 2014).

SUMMARY OF THE INVENTION

An object of the present invention is to provide a compound and a pharmaceutical composition which exhibit an excellent drug efficacy against a tumor, in particular a tumor that has acquired resistance to gemcitabine.

As a result of extensive studies, the present inventors have found that a certain derivative of compound A exhibits an excellent drug efficacy against a tumor, in particular a tumor which has acquired resistance to gemcitabine. The present invention has been completed based on such a finding.

The present invention provides the following.

(1) A thionucleoside derivative represented by General Formula [1]:

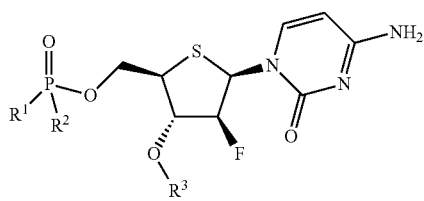

in the formula, $R^1$ represents a hydroxyl group which may be protected, a $C_{1-20}$ alkoxy group which may be substituted, a $C_{3-8}$ cycloalkoxy group which may be substituted, an aryloxy group which may be substituted, a heterocyclic oxy group which may be substituted, or an amino group which may be substituted; $R^2$ represents a $C_{1-20}$ alkoxy group which may be substituted, a $C_{3-8}$ cycloalkoxy group which may be substituted, an aryloxy group which may be substituted, a heterocyclic oxy group which may be substituted, or an amino group which may be substituted; or $R^1$ and $R^2$, together with the phosphorus atom to which they are bonded, may form a 5- to 10-membered nitrogen.phosphorus-containing heterocyclic ring which may be substituted, a 5- to 10-membered oxygen.phosphorus-containing heterocyclic ring which may be substituted, or a 5- to 10-membered nitrogen.oxygen.phosphorus-containing heterocyclic ring; and $R^3$ represents a hydrogen atom; or $R^2$ and $R^3$, together with the phosphorus atom to which $R^2$ is bonded, an oxygen atom, methylene, two carbon atoms constituting the tetrahydrothiophene ring and the oxygen atom to which $R^3$ is bonded, may form a 6 to 10-membered oxygen.phosphorus-containing heterocyclic ring which may be substituted; or a salt thereof.

(2) The thionucleoside derivative according to (1), in which $R^1$ is a hydroxyl group which may be protected, a $C_{1-6}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or an amino group which may be substituted with one or more substituents selected from Substituent group A; or the salt thereof.

(3) The thionucleoside derivative according to (1) or (2), in which $R^2$ is a $C_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A; or the salt thereof.

(4) The thionucleoside derivative according to any one of (1) to (3), in which $R^1$ is a hydroxyl group which may be protected, a $C_{1-6}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or an amino group which may be substituted with one or more substituents selected from Substituent group A; and $R^2$ is a $C_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A; or the salt thereof.

(5) The thionucleoside derivative according to any one of (1) to (4), in which $R^1$ is an aryloxy group which may be substituted with one or more substituents selected from Substituent group A, and $R^2$ is an amino group which may be substituted with one or more substituents selected from Substituent group A, or $R^1$ is a $C_{1-6}$ alkoxy group which may be substituted with one or more substituents selected from Substituent group A, and $R^2$ is a $C_{1-6}$ alkoxy group which may be substituted with one or more substituents selected from Substituent group A; or the salt thereof (6) The thionucleoside derivative according to (1), in which the thionucleoside derivative is a compound selected from:

(2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate, (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-chlorophenoxy)phosphoryl)amino)propanoate, (2S)-cyclobutyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate, (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-bromophenoxy)phosphoryl)amino)propanoate, (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-iodophenoxy)phosphoryl)amino)propanoate, ((2R,3S,4S,5R)-5-(4-amino-2-oxopyrimidin-1(2H)-yl)-4-fluoro-3-hydroxytetrahydrothiophen-2-yl)methyl bis(S-pivaloyl-2-mercaptoethan-1-yl) phosphate, ((2R,3S,4S,5R)-5-(4-amino-2-oxopyrimidin-1(2H)-yl)-4-fluoro-3-hydroxytetrahydrothiophen-2-yl)methyl bis(S-isobutyryl-2-mercaptoethan-1-yl) phosphate, ((2R,3S,4S,5R)-5-(4-amino-2-oxopyrimidin-1(2H)-yl)-4-fluoro-3-hydroxytetrahydrothiophen-2-yl)methyl bis(S-propionyl-2-mercaptoethan-1-yl) phosphate, (((RS)-(((2R,3S,4S,5R)-5-(4-amino-2-oxopyrimidin-1(2H)-yl)-4-fluoro-3-hydroxytetrahydrothiophen-2-yl)methoxy)(2-(pivaloylthio)ethoxy)phosphoryl)oxy)methyl pivalate, S-(2-(((RS)-(((2R,3S,4S,5R)-5-(4-amino-2-oxopyrimidin-1(2H)-yl)-4-fluoro-3-hydroxytetrahydrothiophen-2-yl)methoxy)(((isopropoxycarbonyl)oxy)methoxy)phosphoryl)oxy)ethyl) 2,2-dimethylpropanethioate, ((2R,3S,4S,5R)-5-(4-amino-2-oxopyrimidin-1(2H)-yl)-4-fluoro-3-hydroxytetrahydrothiophen-2-yl)methyl bis(pivaloyloxymethyl) phosphate, ((2R,3S,4S,5R)-5-(4-amino-2-oxopyrimidin-1(2H)-yl)-4-fluoro-3-hydroxytetrahydrothiophen-2-yl)methyl bis(2-((2-(benzyloxy)ethyl)disulfanyl)ethyl) phosphate, ((2R,3S,4S,5R)-5-(4-amino-2-oxopyrimidin-1(2H)-yl)-4-fluoro-3-hydroxytetrahydrothiophen-2-yl)methyl bis(2-((2-pivaloyloxyethyl)disulfanyl)ethyl) phosphate, ((2R,3S,4S,5R)-5-(4-amino-2-oxopyrimidin-1(2H)-yl)-4-fluoro-3-hydroxytetrahydrothiophen-2-yl)methyl bis(2-((2-isobutyroyloxyethyl)disulfanyl)ethyl) phosphate, S-(2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)oxy)ethyl) 2,2-dimethylpropanethioate, 4-amino-1-((2R,3S,4S,5R)-3-fluoro-4-hydroxy-5-((((RS)-2-oxido-4H-benzo[d][1,3,2]dioxaphosphinin-2-yl)oxy)methyl)tetrahydrothiophen-2-yl)pyrimidin-2(1H)-one, (2S)-benzyl 2-(((2RS,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)amino)propanoate, and (2S)-isopropyl 2-(((2RS,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)amino)propanoate; or the salt thereof.

(7) A pharmaceutical composition comprising the thionucleoside derivative or the salt thereof according to any one of (1) to (6).

(8) The pharmaceutical composition according to (7), for use in the treatment of a tumor.

(9) The pharmaceutical composition according to (7), for use in the treatment of lung cancer, esophageal cancer, stomach cancer, colon cancer, rectal cancer, pancreatic cancer, breast cancer, renal cancer, bladder cancer, uterine cancer, osteosarcoma, melanoma, leukemia, multiple myeloma, or malignant lymphoma.

The present invention also provides the following.

(a) A thionucleoside derivative represented by the above defined General Formula [1] or a salt thereof, for use as a medicine.

(b) A thionucleoside derivative represented by General Formula [1] or a salt thereof, for use in the treatment of a tumor.

(c) A thionucleoside derivative represented by General Formula [1] or a salt thereof, for use in the treatment of lung cancer, esophageal cancer, stomach cancer, colon cancer, rectal cancer, pancreatic cancer, breast cancer, renal cancer, bladder cancer, uterine cancer, osteosarcoma, melanoma, leukemia, multiple myeloma, or malignant lymphoma.

(d) A pharmaceutical composition comprising a pharmacologically acceptable additive in conjunction with a thionucleoside derivative represented by General Formula [1] or a salt thereof.

(e) Use of a thionucleoside derivative represented by General Formula [1] or a salt thereof, in the manufacture of a medicine for use in the treatment of a tumor.

(f) Use of a thionucleoside derivative represented by General Formula [1] or a salt thereof, in the manufacture of a medicine for use in the treatment of lung cancer, esophageal cancer, stomach cancer, colon cancer, rectal cancer, pancreatic cancer, breast cancer, renal cancer, bladder cancer, uterine cancer, osteosarcoma, melanoma, leukemia, multiple myeloma, or malignant lymphoma.

(g) A method for the treatment of a tumor, comprising the step of administering a therapeutically effective amount of a thionucleoside derivative represented by General Formula [1] or a salt thereof to a subject (a mammal including a human) in need of such a treatment.

(h) A method for the treatment of lung cancer, esophageal cancer, stomach cancer, colon cancer, rectal cancer, pancreatic cancer, breast cancer, renal cancer, bladder cancer, uterine cancer, osteosarcoma, melanoma, leukemia, multiple myeloma, or malignant lymphoma, comprising the step of administering a therapeutically effective amount of a thionucleoside derivative represented by General Formula [1] or a salt thereof to a subject (a mammal including a human) in need of such a treatment.

The thionucleoside derivative or the salt thereof of the present invention is useful as a tumor treatment agent. The thionucleoside derivative or the salt thereof of the present invention is useful as a tumor treatment agent, in particular, for a tumor which has acquired resistance to gemcitabine.

DESCRIPTION OF THE PREFERRED EMBODIMENTS

Hereinafter, the present invention will be described in detail.

In the present invention, unless otherwise indicated, the individual terms have the following meanings.

The halogen atom refers to a fluorine atom, a chlorine atom, a bromine atom, or an iodine atom.

The $C_{1-6}$ alkyl group refers to a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, or a hexyl group.

The $C_{1-20}$ alkyl group refers to a linear or branched $C_{1-20}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a heptyl group, a 1-methylhexyl group, a 2-methylhexyl group, a 3-methylhexyl group, a 4-methylhexyl group, a 5-methylhexyl group, a 1-propylbutyl group, a 4,4-dimethylpentyl group, an octyl group, a 1-methylheptyl group, a 2-methylheptyl group, a 3-methylheptyl group, a 4-methylheptyl group, a 5-methylheptyl group, a 6-methylheptyl group, a 1-propylpentyl group, a 2-ethylhexyl group, a 5,5-dimethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, or an eicosanyl group.

The $C_{1-6}$ alkylsulfonyl group refers to a $C_{1-6}$ alkylsulfonyl group such as a methylsulfonyl group, an ethylsulfonyl group, or a propylsulfonyl group.

The $C_{1-6}$ alkylsulfonyloxy group refers to a $C_{1-6}$ alkylsulfonyloxy group such as a methylsulfonyloxy group or an ethylsulfonyloxy group.

The $C_{1-6}$ alkyldisulfanyl group refers to a linear or branched $C_{1-6}$ alkyldisulfanyl group such as a methyldisulfanyl group, an ethyldisulfanyl group, a propyldisulfanyl group, an isopropyldisulfanyl group, a butyldisulfanyl group, a sec-butyldisulfanyl group, an isobutyldisulfanyl group, a tert-butyldisulfanyl group, a pentyldisulfanyl group, an isopentyldisulfanyl group, a 2-methylbutyldisulfanyl group, a 2-pentyldisulfanyl group, a 3-pentyldisulfanyl group, or a hexyldisulfanyl group.

The $C_{2-6}$ alkenyl group refers to a linear or branched $C_{2-6}$ alkenyl group such as a vinyl group, an allyl group, a propenyl group, an isopropenyl group, a butenyl group, an isobutenyl group, a 1,3-butadienyl group, a pentenyl group, or a hexenyl group.

The $C_{2-6}$ alkynyl group refers to a linear or branched $C_{2-6}$ alkynyl group such as an ethynyl group, a propynyl group, a butynyl group, a pentynyl group, or a hexynyl group.

The $C_{3-8}$ cycloalkyl group refers to a $C_{3-8}$ cycloalkyl group such as a cyclopropyl group, a cyclobutyl group, a cyclopentyl group, a cyclohexyl group, or a cycloheptyl group.

The $C_{3-8}$ cycloalkyldisulfanyl group refers to a $C_{3-8}$ cycloalkyldisulfanyl group such as a cyclopropyldisulfanyl group, a cyclobutyldisulfanyl group, cyclopentyldisulfanyl group, a cyclohexyldisulfanyl group, or a cycloheptyldisulfanyl group.

The $C_{1-6}$ alkoxy group refers to a linear or branched $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group, or a hexyloxy group.

The $C_{1-20}$ alkoxy group refers to a linear or branched $C_{1-20}$ alkyloxy group such as a methoxy group, an ethoxy group, a propoxy group, an isopropoxy group, a butoxy group, an isobutoxy group, a sec-butoxy group, a tert-butoxy group, a pentyloxy group, a hexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, or an eicosanyloxy.

The $C_{1-6}$ alkoxy $C_{1-6}$ alkyl group refers to a $C_{1-6}$ alkyloxy $C_{1-6}$ alkyl group such as a methoxymethyl group or a 1-ethoxyethyl group.

The $C_{1-6}$ alkoxycarbonyl group refers to a linear or branched $C_{1-6}$ alkyloxycarbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, or a hexyloxycarbonyl group.

The $C_{1-20}$ alkoxycarbonyl group refers to a linear or branched $C_{1-20}$ alkyloxycarbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a hexyloxycarbonyl group, a heptyloxycarbonyl group, an octyloxycarbonyl group, a nonyloxycarbonyl group, a decyloxycarbonyl group, an undecyloxycarbonyl group, a dodecyloxycarbonyl group, a tridecyloxycarbonyl group, a tetradecyloxycarbonyl group, a pentadecyloxycarbonyl group, a hexadecyloxycarbonyl group, a heptadecyloxycarbonyl group, an octadecyloxycarbonyl group, a nonadecyloxycarbonyl group, or an eicosanyloxycarbonyl group.

The $C_{1-6}$ alkoxycarbonyloxy group refers to a linear or branched $C_{1-6}$ alkyloxycarbonyloxy group such as a methoxycarbonyloxy group, an ethoxycarbonyloxy group, a propoxycarbonyloxy group, an isopropoxycarbonyloxy group, a butoxycarbonyloxy group, an isobutoxycarbonyloxy group, a sec-butoxycarbonyloxy group, a tert-butoxycarbonyloxy group, a pentyloxycarbonyloxy group, or a hexyloxycarbonyloxy group.

The $C_{3-8}$ cycloalkoxy group refers to a $C_{3-8}$ cycloalkyloxy group such as a cyclopropoxy group, a cyclobutoxy group, a cyclopentyloxy group, a cyclohexyloxy group, or a cycloheptyloxy group.

The $C_{3-8}$ cycloalkoxycarbonyl group refers to a $C_{3-8}$ cycloalkoxycarbonyl group such as a cyclopropoxycarbonyl group, a cyclobutoxycarbonyl group, a cyclopentyloxycarbonyl group, a cyclohexyloxycarbonyl group, a cycloheptyloxycarbonyl group, or a cyclooctyloxycarbonyl group.

The aryl group refers to a phenyl group or a naphthyl group.

The aryloxy group refers to a phenoxy group, a naphthalen-1-yloxy group, or a naphthalen-2-yloxy group.

The arylsulfonyl group refers to a benzenesulfonyl group, a p-toluenesulfonyl group, or a naphthalenesulfonyl group.

The arylsulfonyloxy group refers to a benzenesulfonyloxy group or a p-toluenesulfonyloxy group.

The aryldisulfanyl group refers to a phenyldisulfanyl group or a naphthyldisulfanyl group.

The ar-$C_{1-6}$ alkyl group refers to an ar-$C_{1-6}$ alkyl group such as a benzyl group, a diphenylmethyl group, a trityl group, a phenethyl group, a 2-phenylpropyl group, a 3-phenylpropyl group, or a naphthylmethyl group.

The ar-$C_{1-6}$ alkoxy group refers to an ar-$C_{1-6}$ alkyloxy group such as a benzyloxy group, a diphenylmethoxy group, a trityloxy group, a phenethyloxy group, a 2-phenylpropoxy group, a 3-phenylpropoxy group, or a naphthylmethoxy group.

The ar-$C_{1-6}$ alkoxy $C_{1-6}$ alkyl group refers to an ar-$C_{1-6}$ alkyloxy $C_{1-6}$ alkyl group such as a benzyloxymethyl group or a phenethyloxymethyl group.

The ar-$C_{1-6}$ alkoxycarbonyl group refers to an ar-$C_{1-6}$ alkyloxycarbonyl group such as a benzyloxycarbonyl group or a phenethyloxycarbonyl group.

The monocyclic nitrogen-containing heterocyclic group refers to a monocyclic nitrogen-containing heterocyclic group which contains only a nitrogen atom as a heteroatom forming the following ring, such as an aziridinyl group, an azetidinyl group, a pyrrolidinyl group, a pyrrolinyl group, a pyrrolyl group, a piperidyl group, a tetrahydropyridyl group, a dihydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group, or a tetrazolyl group.

The monocyclic oxygen-containing heterocyclic group refers to a monocyclic oxygen-containing heterocyclic group which contains only an oxygen atom as a heteroatom forming the following ring, such as an oxetanyl group, a tetrahydrofuranyl group, a furanyl group, a tetrahydropyranyl group, a pyranyl group, a 1,3-dioxanyl group, or a 1,4-dioxanyl group.

The monocyclic sulfur-containing heterocyclic group refers to a thienyl group.

The monocyclic nitrogen.oxygen-containing heterocyclic group refers to a monocyclic nitrogen.oxygen-containing heterocyclic group which contains only a nitrogen atom and an oxygen atom as heteroatoms forming the following ring, such as an oxazolyl group, an isoxazolyl group, an oxadiazolyl group, a morpholinyl group, or an oxazepanyl group.

The monocyclic nitrogen.sulfur-containing heterocyclic group refers to a monocyclic nitrogen.sulfur-containing heterocyclic group which contains only a nitrogen atom and a sulfur atom as heteroatoms forming the following ring, such as a thiazolyl group, an isothiazolyl group, a thiadiazolyl group, a thiomorpholinyl group, a 1-oxidothiomorpholinyl group, or a 1,1-dioxidothiomorpholinyl group.

The monocyclic heterocyclic group refers to a monocyclic nitrogen-containing heterocyclic group, a monocyclic oxygen-containing heterocyclic group, a monocyclic sulfur-containing heterocyclic group, a monocyclic nitrogen.oxygen-containing heterocyclic group, or a monocyclic nitrogen.sulfur-containing heterocyclic group.

The bicyclic nitrogen-containing heterocyclic group refers to a bicyclic nitrogen-containing heterocyclic group which contains only a nitrogen atom as a heteroatom forming the following ring, such as an indolinyl group, an indolyl group, an isoindolinyl group, an isoindolyl group, a benzimidazolyl group, an indazolyl group, a benzotriazolyl group, a pyrazolopyridinyl group, a quinolyl group, a tetrahydroquinolinyl group, a quinolyl group, a tetrahydroisoquinolinyl group, an isoquinolinyl group, a quinolizinyl group, a cinnolinyl group, a phthalazinyl group, a quinazolinyl group, a dihydroquinoxalinyl group, a quinoxalinyl group, a naphthyridinyl group, a purinyl group, a pteridinyl group, or a quinuclidinyl group.

The bicyclic oxygen-containing heterocyclic group refers to a bicyclic oxygen-containing heterocyclic group which contains only an oxygen atom as a heteroatom forming the following ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, or a 1,4-benzodioxanyl group.

The bicyclic sulfur-containing heterocyclic group refers to a bicyclic sulfur-containing heterocyclic group which contains only a sulfur atom as a heteroatom forming the following ring, such as a 2,3-dihydrobenzothienyl group or a benzothienyl group.

The bicyclic nitrogen.oxygen-containing heterocyclic group refers to a bicyclic nitrogen.oxygen-containing heterocyclic group which contains only a nitrogen atom and an oxygen atom as heteroatoms forming the following ring, such as a benzoxazolyl group, a benzisoxazolyl group, a benzoxadiazolyl group, a benzomorpholinyl group, a dihydropyranopyridyl group, a dioxolopyridyl group, a furopyridinyl group, a dihydrodioxynopyridyl group, or a dihydropyridooxazinyl group.

The bicyclic nitrogen.sulfur-containing heterocyclic group refers to a bicyclic nitrogen.sulfur-containing heterocyclic group which contains a nitrogen atom and a sulfur atom as heteroatoms forming the following ring, such as a benzothiazolyl group, a benzoisothiazolyl group, or a benzothiadiazolyl group.

The bicyclic heterocyclic group refers to a bicyclic nitrogen-containing heterocyclic group, a bicyclic oxygen-containing heterocyclic group, a bicyclic sulfur-containing heterocyclic group, a bicyclic nitrogen.oxygen-containing heterocyclic group, or a bicyclic nitrogen.sulfur-containing heterocyclic group.

The spiro heterocyclic group refers to a spiro heterocyclic group which contains a nitrogen atom, an oxygen atom, or a sulfur atom as a heteroatom forming the following ring, such as a 2-oxa-6-azaspiro[3.3]heptyl group, a 1,4-dioxaspiro[4.5]decyl group, a 1-oxa-8-azaspiro[4.5]decyl group, or a 1-thia-8-azaspiro[4.5]decyl group.

The bridged heterocyclic group refers to a bridged heterocyclic group which contains a nitrogen atom, an oxygen atom, or a sulfur atom as a heteroatom forming the following ring, such as a 3-oxa-8-azabicyclo[3.2.1]octyl group, an 8-oxa-3-azabicyclo[3.2.1]octyl group, or a quinuclidinyl group.

The heterocyclic group refers to a monocyclic heterocyclic group, a bicyclic heterocyclic group, a spiro heterocyclic group, or a bridged heterocyclic group.

The heterocyclic oxy group refers to a substituent in which an oxygen atom is bonded to a heterocyclic group such as pyrrolidinyloxy, piperidinyloxy, tetrahydrofuranyloxy, tetrahydropyranyloxy, or tetrahydrothiopyranyloxy.

The 5- to 10-membered nitrogen.phosphorus-containing heterocyclic ring refers to a 5- to 10-membered nitrogen.phosphorus-containing heterocyclic ring which contains only a nitrogen atom and a phosphorus atom as heteroatoms forming the following ring, such as 1,3,2-diazaphospholidine, 1,3,2-diazaphosphinane, 1,3,2-diazaphosphepane, or 1,3,2-diazaphosphocane and which may be fused.

The 5- to 10-membered oxygen.phosphorus-containing heterocyclic ring refers to a 5- to 10-membered oxygen.phosphorus-containing heterocyclic ring which contains only an oxygen atom and a phosphorus atom as heteroatoms forming the following ring, such as 1,3,2-dioxaphospholane, 1,3,2-dioxaphosphinane, 1,3,2-dioxaphosphepane, 1,3,2-dioxaphosphocane, benzo[d][1,3,2]dioxaphosphor, or 4H-benzo[d][1,3,2]dioxaphosphinine and which may be fused.

The 5- to 10-membered nitrogen.oxygen.phosphorus-containing heterocyclic ring refers to a 5- to 10-membered nitrogen.oxygen.phosphorus-containing heterocyclic ring which contains only a nitrogen atom, an oxygen atom, and a phosphorus atom as heteroatoms forming the following ring, such as 1,3,2-oxazaphospholidine, 2,3-dihydrobenzo[d][1,3,2]oxazaphosphor, 1,3,2-oxazaphosphinane, or 3,4-dihydro-4H-benzo[e][1,3,2]oxazaphosphinine and which may be fused.

The 6 to 10-membered oxygen.phosphorus-containing heterocyclic ring refers to a 6 to 10-membered oxygen.phosphorus-containing heterocyclic ring which contains only an oxygen atom and a phosphorus atom as heteroatoms forming the following ring, such as 1,3,2-dioxaphosphinane, 1,3,2-dioxaphosphepane, or 1,3,2-dioxaphosphocane and which may be fused.

The $C_{2-6}$ alkanoyl group refers to a linear or branched $C_{2-6}$ alkanoyl group such as an acetyl group, a propionyl group, a valeryl group, an isovaleryl group, or a pivaloyl group.

The $C_{3-8}$ cycloalkylcarbonyl group refers to a $C_{3-8}$ cycloalkylcarbonyl group such as a cyclopropylcarbonyl group, a cyclobutylcarbonyl group, a cyclopentylcarbonyl group, a cyclohexylcarbonyl group, or a cycloheptylcarbonyl group.

The aroyl group refers to a benzoyl group, a naphthoyl group, or the like.

The heterocyclic carbonyl group refers to a heterocyclic carbonyl group such as pyrrolylcarbonyl, pyridylcarbonyl, furanylcarbonyl, or thienylcarbonyl.

The acyl group refers to a formyl group, a succinyl group, a glutaryl group, a maleoyl group, a phthaloyl group, a $C_{2-6}$ alkanoyl group, a $C_{3-8}$ cycloalkylcarbonyl group, an aroyl group, or a heterocyclic carbonyl group.

The $C_{2-6}$ alkanoyloxy group refers to a linear or branched $C_{2-6}$ alkanoyloxy group such as an acetyloxy group, a propionyloxy group, a valeryloxy group, an isovaleryloxy group, or a pivaloyloxy group.

The $C_{3-8}$ cycloalkylcarbonyloxy group refers to a $C_{3-8}$ cycloalkylcarbonyloxy group such as a cyclopropylcarbonyloxy group, a cyclobutylcarbonyloxy group, a cyclopentylcarbonyloxy group, a cyclohexylcarbonyloxy group, or a cycloheptylcarbonyloxy group.

The aroyloxy group refers to a benzoyloxy group, a naphthoyloxy group, or the like.

The heterocyclic carbonyloxy group refers to a heterocyclic carbonyloxy group such as pyrrolylcarbonyloxy, pyridylcarbonyloxy, furanylcarbonyloxy, or thienylcarbonyloxy.

The acyloxy group refers to a $C_{2-6}$ alkanoyloxy group, a $C_{3-8}$ cycloalkylcarbonyloxy group, an aroyloxy group, or a heterocyclic carbonyloxy group.

The $C_{2-6}$ alkanoylthio group refers to a linear or branched $C_{2-6}$ alkanoylthio group such as an acetylthio group, a propionylthio group, a valerylthio group, an isovalerylthio group, or a pivaloylthio group.

The $C_{3-8}$ cycloalkylcarbonylthio group refers to a $C_{3-8}$ cycloalkylcarbonylthio group such as a cyclopropylcarbonylthio group, a cyclobutylcarbonylthio group, a cyclopentylcarbonylthio group, a cyclohexylcarbonylthio group, or a cycloheptylcarbonylthio group.

The aroylthio group refers to a benzoylthio group, a naphthoylthio group, or the like.

The heterocyclic carbonylthio group refers to a heterocyclic carbonylthio group such as pyrrolylcarbonylthio, pyridylcarbonylthio, furanylcarbonylthio, or thienylcarbonylthio.

The acylthio group refers to a $C_{2-6}$ alkanoylthio group, a $C_{3-8}$ cycloalkylcarbonylthio group, an aroylthio group, or a heterocyclic carbonylthio group.

The silyl group refers to trimethylsilyl, triethylsilyl, a tributylsilyl group, or tert-butylmethylsilyl.

The leaving group refers to a halogen atom, a $C_{1-6}$ alkylsulfonyloxy group, an aryloxy group, or an arylsulfonyloxy group. The $C_{1-6}$ alkylsulfonyloxy group, aryloxy group, and arylsulfonyloxy group may be substituted with one or more substituents selected from a halogen atom, a nitro group, a $C_{1-6}$ alkyl group, and a $C_{1-6}$ alkoxy group.

The hydroxyl protecting group is any conventional group which can be used as a protecting group for a hydroxyl group, and examples thereof include the groups described in, for example, T. W. Greene et al., Protective Groups in Organic Synthesis 4th edition, pp. 16 to 299, 2007, John Wiley & Sons, Inc. Specific examples of the hydroxyl protecting group include a $C_{1-6}$ alkyl group, a $C_{2-6}$ alkenyl group, an ar-$C_{1-6}$ alkyl group, a $C_{1-6}$ alkoxy $C_{1-6}$ alkyl group, an ar-$C_{1-6}$ alkoxy $C_{1-6}$ alkyl group, an acyl group, a $C_{1-6}$ alkoxycarbonyl group, an ar-$C_{1-6}$ alkoxycarbonyl group, a $C_{1-6}$ alkylsulfonyl group, an arylsulfonyl group, a silyl group, a tetrahydrofuranyl group, and a tetrahydropyranyl group.

Aliphatic hydrocarbons refer to pentane, hexane, heptane, cyclohexane, methylcyclohexane, and ethylcyclohexane.

Halogenated hydrocarbons refer to dichloromethane, chloroform, and dichloroethane.

Ethers refer to diethyl ether, diisopropyl ether, dioxane, tetrahydrofuran, anisole, ethylene glycol dimethyl ether, diethylene glycol dimethyl ether, and diethylene glycol diethyl ether.

Ketones refer to acetone, 2-butanone, 4-methyl-2-pentanone, and methyl isobutyl ketone.

Esters refer to methyl acetate, ethyl acetate, propyl acetate, and butyl acetate.

Amides refer to N,N-dimethylformamide, N,N-dimethylacetamide, and N-methylpyrrolidone.

Nitriles refer to acetonitrile and propionitrile.

Sulfoxides refer to dimethyl sulfoxide and sulfolane.

Aromatic hydrocarbons refer to benzene, toluene, and xylene.

The inorganic base refers to sodium hydroxide, potassium hydroxide, sodium methoxide, sodium ethoxide, tert-butoxy sodium, tert-butoxy potassium, sodium hydrogen carbonate, sodium carbonate, potassium carbonate, tripotassium phosphate, potassium acetate, cesium fluoride, cesium carbonate, or tert-butyl magnesium chloride.

The organic base refers to triethylamine, N,N-diisopropylethylamine, 1,8-diazabicyclo(5.4.0)undec-7-ene (DBU), pyridine, 4-dimethylaminopyridine, N-methylmorpholine, or imidazole.

Individual substituent groups have the following meanings.

<Substituent group A> a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; a $C_{1-6}$ alkoxycarbonyloxy group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B.

<Substituent group B> a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an ar-$C_{1-6}$ alkoxycarbonyl group; an aryl group; an aryloxy group; a heterocyclic oxy group which may be substituted with one or more substituents selected from a hydroxyl group and a hydroxymethyl group; an ar-$C_{1-6}$ alkoxy group; and an acyloxy group.

Examples of salts of the thionucleoside derivative represented by General Formula [1] include salts in basic groups such as an amino group, and salts in acidic groups such as a hydroxyl group and a carboxyl group, which are commonly known.

Examples of salts in basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Examples of salts in acidic groups include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Among the salts mentioned above, preferred salts include pharmacologically acceptable salts.

The preventing refers to inhibition of disease onset, reduction of disease onset risk, delay of disease onset, or the like.

The treating refers to improvement of, inhibition of progression of, or the like of a target disease or condition.

The treatment refers to preventing, treating, or the like of a variety of diseases.

The treatment agent refers to a substance which is provided for the purpose of preventing or treating a variety of diseases.

The benign tumor refers to a tumor in which a tumor cell and a sequence thereof take a form close to a normal cell from which the tumor cell and the sequence thereof are derived, and which is free of invasiveness or metastatic properties.

The malignant tumor refers to a tumor in which the morphology and sequence of a tumor cell are different from a normal cell from which such a tumor cell is derived, and which exhibits invasiveness or metastatic properties.

The tumor refers to a benign tumor or a malignant tumor.

The thionucleoside derivative or the salt thereof of the present invention can be used in the treatment of a tumor.

The thionucleoside derivative or the salt thereof of the present invention is preferably used in the treatment of, for example, lung cancer, esophageal cancer, stomach cancer, colon cancer, rectal cancer, pancreatic cancer, breast cancer, renal cancer, bladder cancer, uterine cancer, osteosarcoma, melanoma, leukemia, multiple myeloma, or malignant lymphoma.

In another embodiment, the thionucleoside derivative or the salt thereof of the present invention is preferably used in the treatment of a tumor which has acquired resistance to gemcitabine.

The thionucleoside derivative of the present invention is represented by General Formula [1]

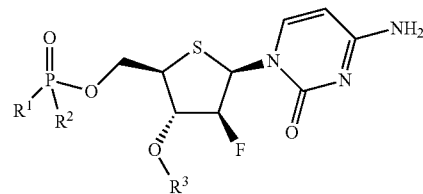

(in the formula, $R^1$, $R^2$, and $R^3$ have the same meanings as above).

$R^1$ $R^1$ is a hydroxyl group which may be protected, a $C_{1-20}$ alkoxy group which may be substituted, a $C_{3-8}$ cycloalkoxy group which may be substituted, an aryloxy group which may be substituted, a heterocyclic oxy group which may be substituted, or an amino group which may be substituted.

$R^1$ is preferably a hydroxyl group which may be protected, a $C_{1-6}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or an amino group which may be substituted with one or more substituents selected from Substituent group A, more preferably a $C_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A, and still more preferably a $C_{1-6}$ alkoxy group which may be substituted with one or more substituents selected from Substituent group A or an aryloxy group which may be substituted with one or more substituents selected from Substituent group A.

The substituent of the $C_{1-6}$ alkoxy group which may be substituted with one or more substituents selected from Substituent group A in the definition of $R^1$ is preferably a $C_{1-6}$ alkyldisulfanyl group which may be substituted with one or more substituents selected from Substituent group B, a $C_{1-6}$ alkoxycarbonyloxy group which may be substituted with one or more substituents selected from Substituent group B, an acyloxy group which may be substituted with one or more substituents selected from Substituent group B, or an acylthio group which may be substituted with one or more substituents selected from Substituent group B, and more preferably a $C_{1-6}$ alkyldisulfanyl group which may be substituted with one or more substituents selected from Substituent group B, a $C_{1-6}$ alkoxycarbonyloxy group which may be substituted with one or more substituents selected from Substituent group B, a $C_{2-6}$ alkanoyloxy group which may be substituted with one or more substituents selected from Substituent group B, or a $C_{2-6}$ alkanoylthio group which may be substituted with one or more substituents selected from Substituent group B.

Here, the substituent of the $C_{1-6}$ alkyldisulfanyl group which may be substituted with one or more substituents selected from Substituent group B is preferably a hydroxyl group, a $C_{1-6}$ alkoxy group, an ar-$C_{1-6}$ alkoxy group, or an acyloxy group and more preferably a hydroxyl group, a $C_{1-6}$ alkoxy group, an ar-$C_{1-6}$ alkoxy group, or a $C_{2-6}$ alkanoyloxy group.

The substituent of the aryloxy group which may be substituted with one or more substituents selected from Substituent group A in the definition of $R^1$ is preferably a halogen atom or a $C_{1-6}$ alkoxy group which may be substituted with one or more substituents selected from Substituent group B.

The substituent of the amino group which may be substituted with one or more substituents selected from Substituent group A in the definition of $R^1$ is preferably a $C_{1-6}$ alkyl group which may be substituted with one or more substituents selected from Substituent group B.

Here, the substituent of the $C_{1-6}$ alkyl group which may be substituted with one or more substituents selected from Substituent group B is preferably a $C_{1-6}$ alkoxycarbonyl group, an aryl group, or an ar-$C_{1-6}$ alkoxycarbonyl group.

$R^2$ $R^2$ is a $C_{1-20}$ alkoxy group which may be substituted, a $C_{3-8}$ cycloalkoxy group which may be substituted, an aryloxy group which may be substituted, a heterocyclic oxy group which may be substituted, or an amino group which may be substituted.

$R^2$ is preferably a $C_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A and more preferably a $C_{1-6}$ alkoxy group which may be substituted with one or more substituents selected from Substituent group A or an amino group which may be substituted with one or more substituents selected from Substituent group A.

The substituent of the $C_{1-6}$ alkoxy group which may be substituted with one or more substituents selected from Substituent group A in the definition of $R^2$ is preferably a $C_{1-6}$ alkyldisulfanyl group which may be substituted with one or more substituents selected from Substituent group B, a $C_{1-6}$ alkoxycarbonyloxy group which may be substituted with one or more substituents selected from Substituent group B, a heterocyclic oxy group which may be substituted with one or more substituents selected from Substituent group B, an acyloxy group which may be substituted with one or more substituents selected from Substituent group B, an acylthio group which may be substituted with one or more substituents selected from Substituent group B, an aminocarbonyloxy group which may be substituted with one or more substituents selected from Substituent group B, or an aminocarbonylthio group which may be substituted with one or more substituents selected from Substituent group B, more preferably a $C_{1-6}$ alkyldisulfanyl group which may be substituted with one or more substituents selected from Substituent group B, a $C_{1-6}$ alkoxycarbonyloxy group which may be substituted with one or more substituents selected from Substituent group B, an acyloxy group which may be substituted with one or more substituents selected from Substituent group B, or an acylthio group which may be substituted with one or more substituents selected from Substituent group B, and still more preferably a $C_{1-6}$ alkyldisulfanyl group which may be substituted with one or more substituents selected from Substituent group B, a $C_{1-6}$ alkoxycarbonyloxy group which may be substituted with one or more substituents selected from Substituent group B, a $C_{2-6}$ alkanoyloxy group which may be substituted with one or more substituents selected from Substituent group B, or a $C_{2-6}$ alkanoylthio group which may be substituted with one or more substituents selected from Substituent group B.

Here, the substituent of the $C_{1-6}$ alkyldisulfanyl group which may be substituted with one or more substituents selected from Substituent group B is preferably a hydroxyl group, an ar-$C_{1-6}$ alkoxy group, or an acyloxy group and more preferably a hydroxyl group, an ar-$C_{1-6}$ alkoxy group, or a $C_{1-6}$ alkanoyloxy group.

The substituent of the heterocyclic oxy group which may be substituted with one or more substituents selected from Substituent group B is preferably a hydroxyl group or a hydroxymethyl group.

The substituent of the amino group which may be substituted with one or more substituents selected from Substituent group A in the definition of $R^2$ is preferably a $C_{1-6}$ alkyl group which may be substituted with one or more substituents selected from Substituent group B or a heterocyclic group which may be substituted with one or more substituents selected from Substituent group B.

Here, the substituent of the $C_{1-6}$ alkyl group which may be substituted with one or more substituents selected from Substituent group B is preferably a carboxyl group, a $C_{1-6}$ alkoxycarbonyl group, a $C_{3-8}$ cycloalkoxycarbonyl group, an aryl group, or an ar-$C_{1-6}$ alkoxycarbonyl group.

$R^1$ and $R^2$, together with the phosphorus atom to which they are bonded, may form a 5- to 10-membered nitrogen. phosphorus-containing heterocyclic ring which may be substituted, a 5- to 10-membered oxygen.phosphorus-containing heterocyclic ring which may be substituted, or a 5- to 10-membered nitrogen.oxygen.phosphorus-containing heterocyclic ring which may be substituted.

The ring formed by $R^1$ and $R^2$ together with the phosphorus atom to which they are bonded is preferably a 5- to 10-membered oxygen.phosphorus-containing heterocyclic ring which may be substituted and more preferably 1,3,2-dioxaphosphinane or 4H-benzo[d][1,3,2]dioxaphosphinine.

The substituent of the 5- to 10-membered nitrogen.phosphorus-containing heterocyclic ring which may be substituted, the 5- to 10-membered oxygen.phosphorus-containing heterocyclic ring which may be substituted, or the 5- to 10-membered nitrogen.oxygen.phosphorus-containing heterocyclic ring which may be substituted, each of which being formed by $R^1$ and $R^2$ together with the phosphorus atom to which they are bonded, is preferably a $C_{1-6}$ alkoxy group which may be substituted with one or more substituents selected from Substituent group A or an aryl group which may be substituted with one or more substituents selected from Substituent group A.

Here, the substituent of the aryl group which may be substituted with one or more substituents selected from Substituent group A is preferably a halogen atom.

$R^3$ $R^3$ is a hydrogen atom.

$R^2$ and $R^3$, together with the phosphorus atom to which $R^2$ is bonded, an oxygen atom, methylene, two carbon atoms constituting the tetrahydrothiophene ring and the oxygen atom to which $R^3$ is bonded, may form a 6 to 10-membered oxygen.phosphorus-containing heterocyclic ring which may be substituted.

The ring formed by $R^2$ and $R^3$ together with the phosphorus atom to which $R^2$ is bonded, an oxygen atom, methylene, two carbon atoms constituting the tetrahydrothiophene ring and the oxygen atom to which $R^3$ is bonded is preferably 1,3,2-dioxaphosphinane.

The compound represented by General Formula [1] is preferably a compound in which $R^1$ is a hydroxyl group which may be protected, a $C_{1-20}$ alkoxy group which may be substituted, a $C_{3-8}$ cycloalkoxy group which may be substituted, an aryloxy group which may be substituted, a heterocyclic oxy group which may be substituted, or an amino group which may be substituted; $R^2$ is a $C_{1-20}$ alkoxy group which may be substituted, a $C_{3-8}$ cycloalkoxy group which may be substituted, an aryloxy group which may be substituted, a heterocyclic oxy group which may be substituted, or an amino group which may be substituted; and $R^3$ is a hydrogen atom, and more preferably a compound in which $R^1$ is a hydroxyl group which may be protected, a $C_{1-6}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or an amino group which may be substituted with one or more substituents selected from Substituent group A; $R^2$ is a $C_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A; and $R^3$ is a hydrogen atom.

In the case where isomers (for example, a tautomer, an optical isomer, and a geometric isomer) are present for the thionucleoside derivative represented by General Formula [1] or the salt thereof, the present invention also encompasses those isomers and further encompasses solvates, hydrates, and various forms of crystals.

Next, the production method of the compound of the present invention will be described.

The compound of the present invention is produced by combining per se known methods, and for example, can be produced according to the following production methods.

[Production Method A]

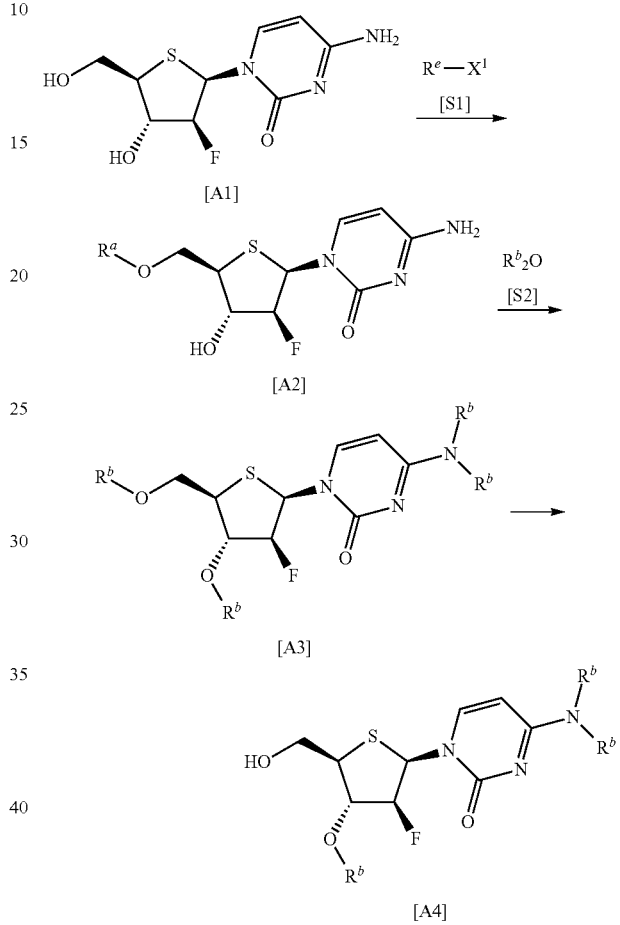

(in the formulae, $R^a$ represents a silyl group which may be substituted; $R^b$ represents a $C_{1-20}$ alkoxycarbonyl group which may be substituted or a $C_{3-8}$ cycloalkoxycarbonyl group which may be substituted; and $X^1$ represents a leaving group).

First Step

As the compound of General Formula [S1], for example, tert-butyldiphenylchlorosilane is known.

The compound of General Formula [A2] can be produced by reacting the compound of Formula [A1] with the compound of General Formula [S1] in the presence of a base.

The solvent used in this reaction is not particularly limited as long as it does not affect the reaction, and examples thereof include aliphatic hydrocarbons, halogenated hydrocarbons, ethers, ketones, esters, amides, nitriles, sulfoxides, and aromatic hydrocarbons. These solvents may be used as a mixture thereof.

Examples of the preferred solvent include amides. More preferred is N,N-dimethylformamide.

The amount of the solvent to be used is not particularly limited, but may be 1 to 50-fold amount (v/w) with respect to the compound of Formula [A1].

The amount of the compound of General Formula [S1] to be used may be 1 to 5-fold molar excess and preferably 1 to 2-fold molar excess with respect to the compound of Formula [A1].

The base used in this reaction may be, for example, an inorganic base or an organic base and is preferably an organic base and more preferably imidazole.

The amount of the base to be used may be 1 to 10-fold molar excess and preferably 1 to 5-fold molar excess with respect to the compound of Formula [A1].

This reaction may be carried out at 0° C. to 100° C., preferably 10° C. to 50° C. for 30 minutes to 48 hours.

Second Step

As the compound of General Formula [S2], for example, di-tert-butyldicarbonate is known.

The compound of General Formula [A3] can be produced by reacting the compound of General Formula [A2] with the compound of General Formula [S2] in the presence of a base.

The solvent used in this reaction is not particularly limited as long as it does not affect the reaction, and examples thereof include aliphatic hydrocarbons, halogenated hydrocarbons, ethers, ketones, esters, amides, nitriles, sulfoxides, and aromatic hydrocarbons. These solvents may be used as a mixture thereof.

Examples of the preferred solvent include halogenated hydrocarbons. More preferred is methylene chloride.

The amount of the solvent to be used is not particularly limited, but may be 1 to 50-fold amount (v/w) with respect to the compound of General Formula [A2].

The amount of the compound of General Formula [S2] to be used may be 3 to 10-fold molar excess and preferably 3 to 6-fold molar excess with respect to the compound of General Formula [A2].

The base used in this reaction may be, for example, an inorganic base or an organic base and is preferably an organic base and more preferably pyridine, triethylamine, or diisopropylethylamine. These bases may be used as a mixture thereof.

The amount of the base to be used may be 3 to 20-fold molar excess and preferably 3 to 10-fold molar excess with respect to the compound of General Formula [A2]. In addition, the base may be used as a solvent.

It is preferred to add a reaction accelerator to this reaction.

The reaction accelerator may be, for example, 4-dimethylaminopyridine.

The amount of the reaction accelerator to be used may be 0.01 to 1-fold molar excess with respect to the compound of General Formula [A2].

This reaction may be carried out at 0° C. to 100° C., preferably 10° C. to 50° C. for 30 minutes to 48 hours.

Third Step

The compound of General Formula [A4] can be produced by deprotecting the compound of General Formula [A3].

This reaction may be carried out in accordance with the method described in, for example, T. W. Greene et al., Protective Groups in Organic Synthesis, 4th edition, pp. 16 to 366, 2007, John Wiley & Sons, Inc.

[Production Method B]

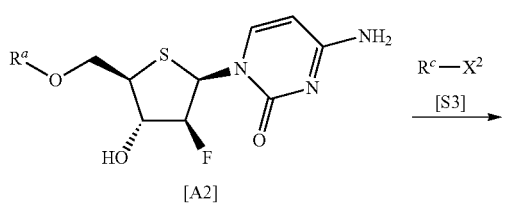

[A2]

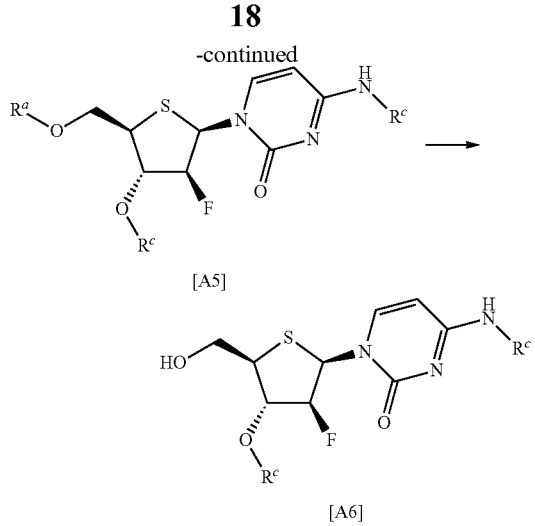

[A5]

[A6]

(in the formulae, $R^c$ represents an acyl group which may be substituted, a $C_{1-20}$ alkoxycarbonyl group which may be substituted, or a $C_{3-8}$ cycloalkoxycarbonyl group which may be substituted; $X^2$ represents a leaving group; and $R^a$ has the same meaning as above).

First Step

As the compound of General Formula [S3], for example, benzoyl chloride is known.

The compound of General Formula [A5] can be produced by reacting the compound of General Formula [A2] with the compound of General Formula [S3] in the presence of a base.

The solvent used in this reaction is not particularly limited as long as it does not affect the reaction and examples thereof include aliphatic hydrocarbons, halogenated hydrocarbons, ethers, ketones, esters, amides, nitriles, sulfoxides, and aromatic hydrocarbons. These solvents may be used as a mixture thereof.

Examples of the preferred solvent include halogenated hydrocarbons, ethers, and amides. More preferred are methylene chloride, tetrahydrofuran, and N,N-dimethylformamide.

The amount of the solvent to be used is not particularly limited, but may be 1 to 50-fold amount (v/w) with respect to the compound of General Formula [A2].

The amount of the compound of General Formula [S3] to be used may be 2 to 20-fold molar excess and preferably 2 to 5-fold molar excess with respect to the compound of General Formula [A2].

The base used in this reaction may be, for example, an inorganic base or an organic base and is preferably an organic base and more preferably pyridine, triethylamine, or diisopropylethylamine. These bases may be used as a mixture thereof.

The amount of the base to be used may be 2 to 20-fold molar excess and preferably 2 to 10-fold molar excess with respect to the compound of General Formula [A2]. In addition, the base may be used as a solvent.

If necessary, a reaction accelerator may be added to this reaction.

The reaction accelerator may be, for example, 4-dimethylaminopyridine.

The amount of the reaction accelerator to be used may be 0.01 to 1-fold molar excess with respect to the compound of General Formula [A2].

This reaction may be carried out at 0° C. to 100° C., preferably 0° C. to 40° C. for 30 minutes to 48 hours.

Second Step

The compound of General Formula [A6] can be produced by deprotecting the compound of General Formula [A5].

This reaction may be carried out in accordance with the third step of production method A.

[Production Method C]

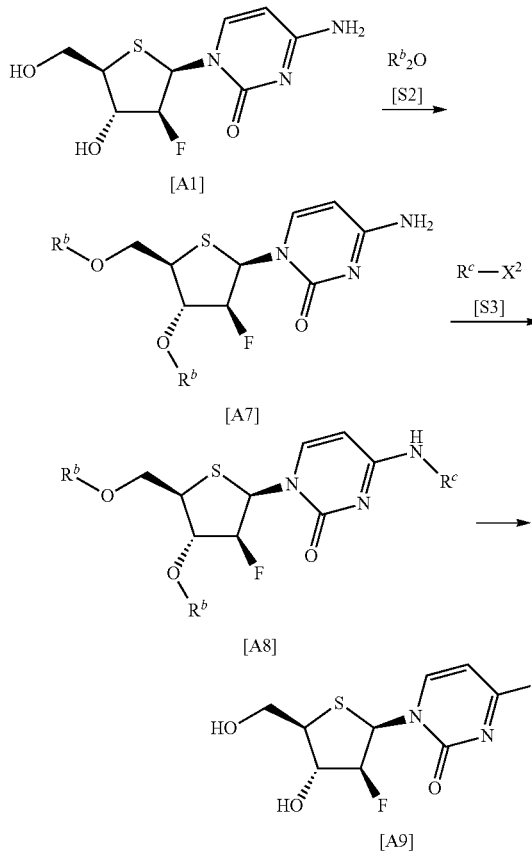

(in the formulae, $R^b$, $R^c$, and $X^2$ have the same meanings as above).

First Step

As the compound of General Formula [S2], for example, di-tert-butyldicarbonate is known.

The compound of General Formula [A7] can be produced by reacting the compound of Formula [A1] with the compound of General Formula [S2] in the presence of a base.

The solvent used in this reaction is not particularly limited as long as it does not affect the reaction and examples thereof include ethers and water. These solvents may be used as a mixture thereof.

Examples of the preferred solvent include tetrahydrofuran, 1,4-dioxane, and water. More preferred are a mixed solvent of tetrahydrofuran and water and a mixed solvent of 1,4-dioxane and water.

The amount of the solvent to be used is not particularly limited, but may be 1 to 50-fold amount (v/w) with respect to the compound of General Formula [A1].

The amount of the compound of General Formula [S2] to be used may be 2 to 20-fold molar excess and preferably 2 to 10-fold molar excess with respect to the compound of General Formula [A1].

The base used in this reaction may be, for example, an inorganic base or an organic base and is preferably an inorganic base and more preferably sodium hydroxide or potassium hydroxide. These bases may be used as a mixture thereof.

The amount of the base to be used may be 2 to 30-fold molar excess and preferably 2 to 15-fold molar excess with respect to the compound of General Formula [A1]. In addition, the base may be used as a solvent.

If necessary, a reaction accelerator may be added to this reaction.

The reaction accelerator may be, for example, 4-dimethylaminopyridine.

The amount of the reaction accelerator to be used may be 0.01 to 1-fold molar excess with respect to the compound of General Formula [A1].

This reaction may be carried out at 0° C. to 100° C., preferably 0° C. to 40° C. for 30 minutes to 48 hours.

Second Step

The compound of General Formula [A8] can be produced by reacting the compound of General Formula [A7] with the compound of General Formula [S3] in the presence of a base.

This reaction may be carried out in accordance with the first step of production method B.

Third Step

The compound of General Formula [A9] can be produced by deprotecting the compound of General Formula [A8].

This reaction may be carried out in accordance with the third step of production method A.

[Production Method 1]

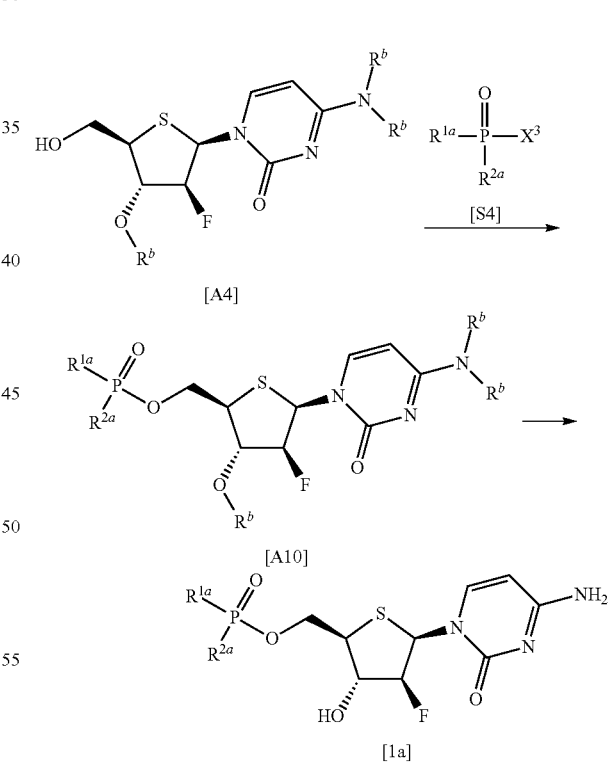

(in the formulae, $R^{1a}$ and $R^{2a}$ are the same or different and represent a $C_{1-20}$ alkoxy group which may be substituted, a $C_{3-8}$ cycloalkoxy group which may be substituted, an aryloxy group which may be substituted, a heterocyclic oxy group which may be substituted, or an amino group which may be substituted; or $R^{1a}$ and $R^{2a}$, together with the phosphorus atom to which they are bonded, may form a 5- to 10-membered nitrogen.phosphorus-containing heterocyclic ring which may be substituted, a 5- to 10-membered oxygen.phosphorus-containing heterocyclic ring which may be substituted, or a 5- to 10-membered nitrogen.oxygen.phosphorus-containing heterocyclic ring which may be substituted; $X^3$ represents a leaving group: and $R^b$ has the same meaning as above).

First Step

As the compound of General Formula [S4], for example, (2S)-benzyl 2-(((RS)-chloro(phenoxy)phosphoryl)amino)propanoate, (2S)-benzyl 2-(((RS)-chloro(4-chlorophenoxy)phosphoryl)amino)propanoate, S-(2-(((RS)-chloro(phenoxy)phosphoryl)oxy)ethyl) 2,2-dimethylpropanethioate, and (2RS,4R)-2-(4-nitrophenoxy)-4-phenyl-1,3,2-dioxaphosphinane 2-oxide are known.

The compound of General Formula [A10] can be produced by reacting the compound of General Formula [A4] with the compound of General Formula [S4] in the presence of a base.

The solvent used in this reaction is not particularly limited as long as it does not affect the reaction and examples thereof include ethers and aromatic hydrocarbons. These solvents may be used as a mixture thereof.

Examples of the preferred solvent include ethers. More preferred is tetrahydrofuran.

The amount of the solvent to be used is not particularly limited, but may be 1 to 50-fold amount (v/w) with respect to the compound of General Formula [A4].

The amount of the compound of General Formula [S4] to be used may be 1 to 20-fold molar excess and preferably 1 to 10-fold molar excess with respect to the compound of General Formula [A4].

The base used in this reaction may be, for example, tert-butyl magnesium chloride.

The amount of the base to be used may be 1 to 5-fold molar excess and preferably 1 to 2-fold molar excess with respect to the compound of General Formula [A4].

This reaction may be carried out at −78° C. to 100° C., preferably −78° C. to 40° C. for 30 minutes to 48 hours.

Second Step

The compound of General Formula [1a] can be produced by deprotecting the compound of General Formula [A10].

This reaction may be carried out in accordance with the third step of production method A.

[Production Method 2]

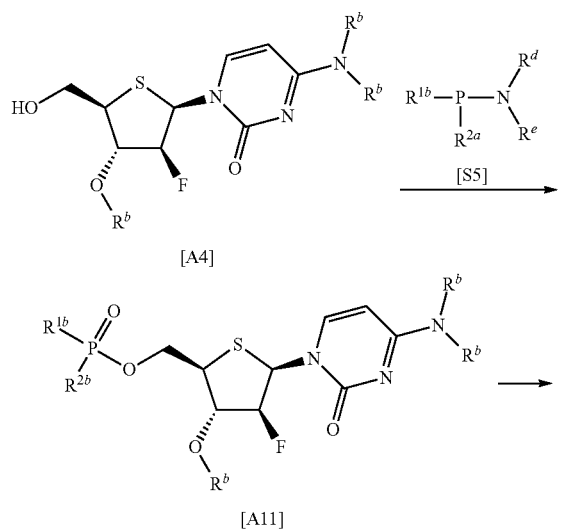

[A4]

[A11]

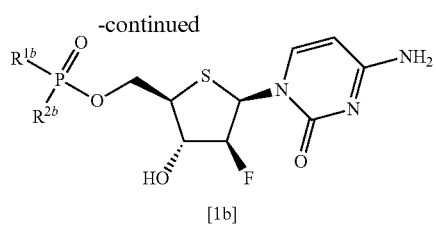

[1b]

(in the formulae, $R^{1b}$ and $R^{2b}$ are the same or different and represent a $C_{1-20}$ alkoxy group which may be substituted or a $C_{3-8}$ cycloalkoxy group which may be substituted; $R^d$ and $R^e$ are the same or different and represent a $C_{1-20}$ alkyl group which may be substituted; and $R^b$ has the same meaning as above).

First Step

As the compound of General Formula [S5], for example, S,S'-(((((diisopropylamino)phosphinediyl)bis(oxy))bis(ethane-2,1-diyl)) bis(2,2-dimethylpropanethioate) and S-(2-(((2-cyanoethoxy)(diisopropylamino)phosphino)oxy)ethyl) 2,2-dimethylpropanethioate are known.

The compound of General Formula [A11] can be produced by reacting the compound of General Formula [A4] with the compound of General Formula [S5], followed by reaction with an oxidizing agent.

The solvent used in this reaction is not particularly limited as long as it does not affect the reaction and examples thereof include halogenated hydrocarbons, ethers, amides, and nitriles. These solvents may be used as a mixture thereof.

Examples of the preferred solvent include methylene chloride, tetrahydrofuran, N,N-dimethylformamide, and acetonitrile. More preferred is methylene chloride.

The amount of the solvent to be used is not particularly limited, but may be 1 to 50-fold amount (v/w) with respect to the compound of General Formula [A4].

The amount of the compound of General Formula [S5] to be used may be 1 to 10-fold molar excess and preferably 1 to 5-fold molar excess with respect to the compound of General Formula [A4].

It is preferred to add a reaction accelerator to this reaction.

The reaction accelerator may be, for example, 1H-tetrazole.

The amount of the reaction accelerator to be used may be 1 to 10-fold molar excess and preferably 1 to 5-fold molar excess with respect to the compound of General Formula [A4].

The reaction with the compound of General Formula [S5] may be carried out at −78° C. to 40° C. for 30 minutes to 24 hours.

The oxidizing agent to be used in this reaction may be, for example, meta-chloroperbenzoic acid.

The amount of the oxidizing agent to be used may be 1 to 5-fold molar excess and preferably 1 to 2-fold molar excess with respect to the compound of General Formula [A4].

The reaction with the oxidizing agent may be carried out at −78° C. to 40° C. for 30 minutes to 24 hours.

Second Step

The compound of General Formula [1b] can be produced by deprotecting the compound of General Formula [A11].

This reaction may be carried out in accordance with the third step of production method A.

[Production Method 3]

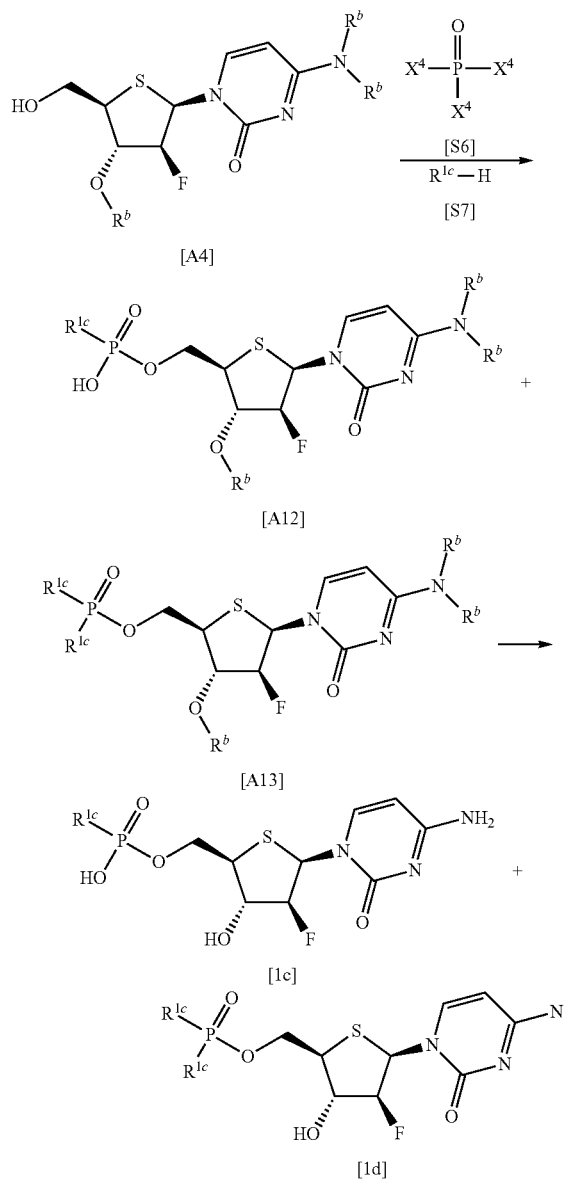

(in the formulae, $R^{1c}$ represents a $C_{1-20}$ alkoxy group which may be substituted, a $C_{3-8}$ cycloalkoxy group which may be substituted, or an amino group which may be substituted; $X^4$ represents a leaving group: and $R^b$ has the same meaning as above).

First Step

As the compound of General Formula [S6], for example, phosphorus oxychloride is known.

As the compound of General Formula [S7], for example, L-alanine benzyl ester and 2,2'-disulfanediyldiethanol are known.

The compounds of General Formula [A12] and General Formula [A13] can be produced by reacting the compound of General Formula [A4] with the compound of General Formula [S6] in the presence of a base, followed by reaction with the compound of General Formula [S7].

The solvent used in this reaction is not particularly limited as long as it does not affect the reaction and examples thereof include halogenated hydrocarbons, ethers, and aromatic hydrocarbons. These solvents may be used as a mixture thereof.

Examples of the preferred solvent include halogenated hydrocarbons. More preferred is methylene chloride.

The amount of the solvent to be used is not particularly limited, but may be 1 to 50-fold amount (v/w) with respect to the compound of General Formula [A4].

The amount of the compound of General Formula [S6] to be used may be 1 to 3-fold molar excess and preferably 1 to 2-fold molar excess with respect to the compound of General Formula [A4].

The base used in this reaction is preferably an organic base and more preferably triethylamine or diisopropylethylamine. These bases may be used as a mixture thereof.

The amount of the base to be used may be 3 to 15-fold molar excess and preferably 3 to 6-fold molar excess with respect to the compound of General Formula [A4].

The reaction with the compound of General Formula [S6] may be carried out at −78° C. to 0° C. for 30 minutes to 24 hours.

The amount of the compound of General Formula [S7] to be used may be 1 to 5-fold molar excess and preferably 2 to 3-fold molar excess with respect to the compound of General Formula [A4].

The reaction with the compound of General Formula [S7] may be carried out at −78° C. to 0° C. for 30 minutes to 24 hours.

The reaction with the compound of General Formula [S7] may be carried out at 0° C. to 100° C., preferably 0° C. to 40° C. for 30 minutes to 24 hours.

Second Step

The compounds of General Formula [1c] and General Formula [1d] can be produced by deprotecting the compounds of General Formula [A12] and General Formula [A13].

This reaction may be carried out in accordance with the third step of production method A.

[Production Method 4]

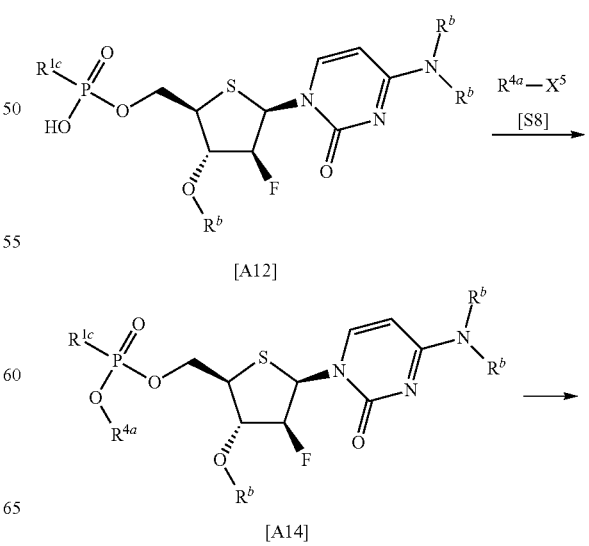

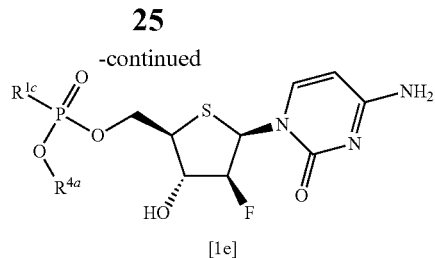

[1e]

(in the formulae, $R^{4a}$ represents a $C_{1-20}$ alkyl group which may be substituted; $X^5$ represents a leaving group; and $R^b$ and $R^{1c}$ have the same meanings as above).

First Step

As the compound of General Formula [S8], for example, chloromethyl isopropyl carbonate and chloromethyl pivalate are known.

The compound of General Formula [A14] can be produced by reacting the compound of General Formula [A12] with the compound of General Formula [S8] in the presence of a base.

The solvent used in this reaction is not particularly limited as long as it does not affect the reaction and examples thereof include amides, nitriles, and sulfoxides. These solvents may be used as a mixture thereof.

Examples of the preferred solvent include amides. More preferred is N,N-dimethylformamide.

The amount of the solvent to be used is not particularly limited, but may be 1 to 50-fold amount (v/w) with respect to the compound of General Formula [A12].

The amount of the compound of General Formula [S8] to be used may be 1 to 10-fold molar excess and preferably 1 to 5-fold molar excess with respect to the compound of General Formula [A12].

The base used in this reaction may be, for example, an inorganic base or an organic base and is preferably an organic base and more preferably triethylamine or N,N-diisopropylethylamine. These bases may be used as a mixture thereof.

The amount of the base to be used may be 1 to 20-fold molar excess and preferably 1 to 10-fold molar excess with respect to the compound of General Formula [A12]. In addition, the base may be used as a solvent.

This reaction may be carried out at 0° C. to 100° C., preferably 50° C. to 80° C. for 30 minutes to 48 hours.

Second Step

The compound of General Formula [1e] can be produced by deprotecting the compound of General Formula [A14].

This reaction may be carried out in accordance with the third step of production method A.

[Production Method 5]

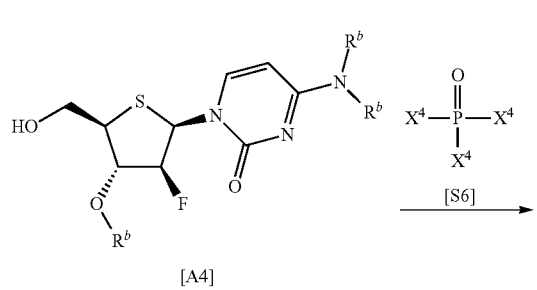

[A4]

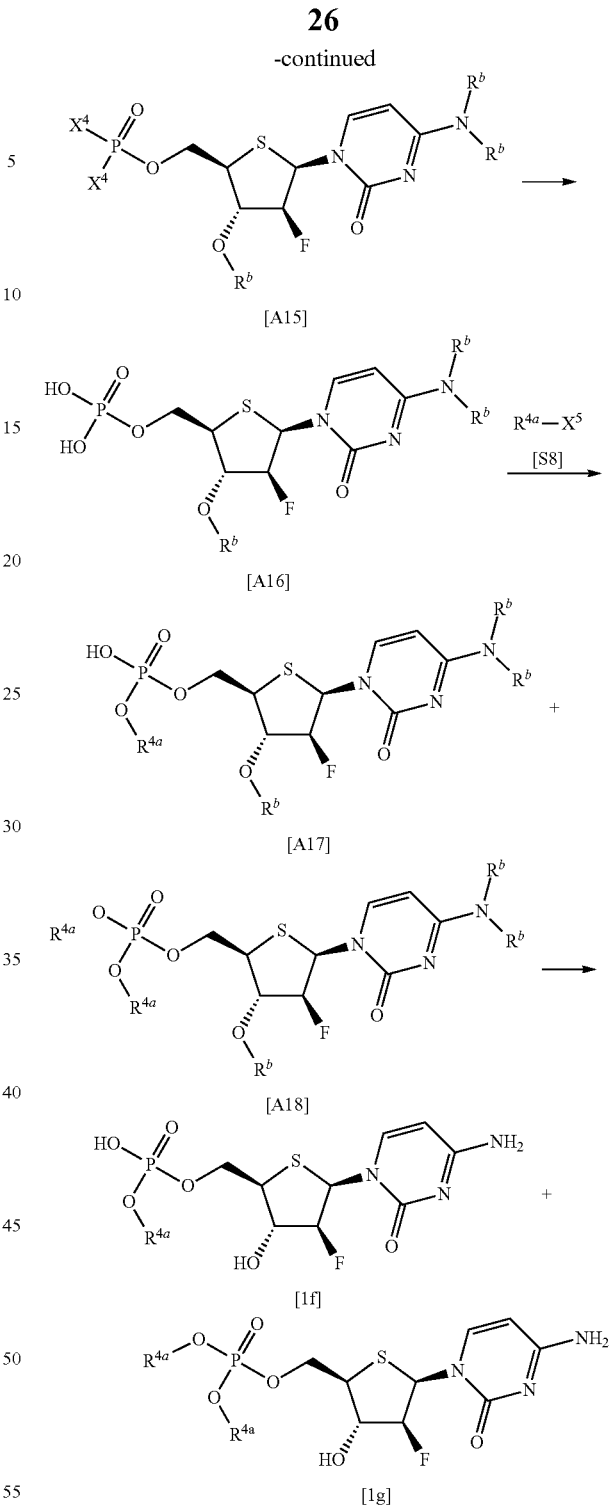

(in the formulae, $R^{4a}$, $R^b$, $X^4$, and $X^5$ have the same meanings as above).

First Step

As the compound of General Formula [S6], for example, phosphorus oxychloride is known.

The compound of General Formula [A15] can be produced by reacting the compound of Formula [A4] with the compound of General Formula [S6] in the presence of a base.

The solvent used in this reaction is not particularly limited as long as it does not affect the reaction and examples thereof include halogenated hydrocarbons, ethers, and aromatic hydrocarbons. These solvents may be used as a mixture thereof.

Examples of the preferred solvent include halogenated hydrocarbons. More preferred is methylene chloride.

The amount of the solvent to be used is not particularly limited, but may be 1 to 50-fold amount (v/w) with respect to the compound of General Formula [A4].

The amount of the compound of General Formula [S6] to be used may be 1 to 3-fold molar excess and preferably 1 to 2-fold molar excess with respect to the compound of General Formula [A4].

The base used in this reaction is preferably an organic base and more preferably triethylamine or diisopropylethylamine. These bases may be used as a mixture thereof.

The amount of the base to be used may be 1 to 5-fold molar excess and preferably 1 to 2-fold molar excess with respect to the compound of General Formula [A4].

The reaction with the compound of General Formula [S6] may be carried out at −78° C. to 0° C. for 30 minutes to 24 hours.

The compound of General Formula [A15] is preferably used in the next step without isolation thereof.

Second Step

The compound of General Formula [A16] can be produced by reacting the compound of General Formula [A15] with water in the presence of a base.

The base used in this reaction is preferably an organic base and more preferably triethylamine or diisopropylethylamine. These bases may be used as a mixture thereof.

The amount of the base to be used may be 2 to 10-fold molar excess and preferably 2 to 4-fold molar excess with respect to the compound of General Formula [A15].

This reaction may be carried out at 0° C. to 50° C. for 30 minutes to 24 hours.

Third Step

As the compound of General Formula [S8], for example, chloromethyl isopropylcarbonate and chloromethyl pivalate are known.

The compounds of General Formula [A17] and General Formula [A18] can be produced by reacting the compound of General Formula [A16] with the compound of General Formula [S8] in the presence of a base.

The solvent used in this reaction is not particularly limited as long as it does not affect the reaction and examples thereof include amides, nitriles, and sulfoxides. These solvents may be used as a mixture thereof.

Examples of the preferred solvent include amides. More preferred is N,N-dimethylformamide.

The amount of the solvent to be used is not particularly limited, but may be 1 to 50-fold amount (v/w) with respect to the compound of General Formula [A16].

The amount of the compound of General Formula [S8] to be used may be 2 to 20-fold molar excess and preferably 2 to 10-fold molar excess with respect to the compound of General Formula [A16].

The base used in this reaction may be, for example, an inorganic base or an organic base and is preferably an organic base and more preferably triethylamine or N,N-diisopropylethylamine. These bases may be used as a mixture thereof.

The amount of the base to be used may be 2 to 20-fold molar excess and preferably 2 to 10-fold molar excess with respect to the compound of General Formula [A16]. In addition, the base may be used as a solvent.

This reaction may be carried out at 0° C. to 100° C., preferably 50° C. to 80° C. for 30 minutes to 48 hours.

Fourth Step

The compounds of General Formulae [1f] and [1g] can be produced by deprotecting the compounds of General Formula [A17] and General Formula [A18].

This reaction may be carried out in accordance with the third step of production method A.

[Production Method 6]

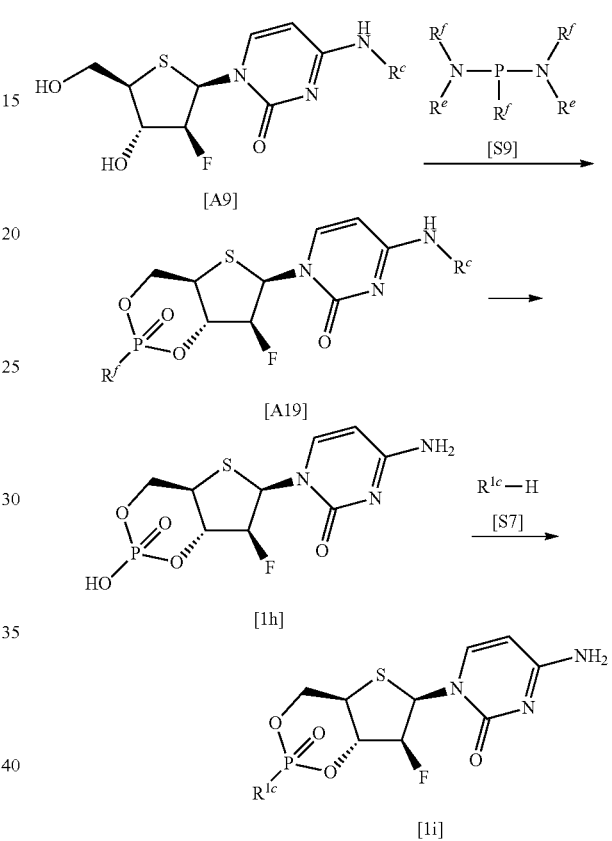

(in the formulae, $R^f$ represents a $C_{1-20}$ alkoxy group which may be substituted; and $R^c$, $R^e$, and $R^{1c}$ have the same meanings as above).

First Step

As the compound of General Formula [S9], for example, 2-cyanoethyl N,N,N',N'-tetraisopropyl phosphorodiamidite is known.

The compound of General Formula [A19] can be produced by reacting the compound of General Formula [A9] with the compound of General Formula [S9], followed by reaction with an oxidizing agent.

The solvent used in this reaction is not particularly limited as long as it does not affect the reaction and examples thereof include halogenated hydrocarbons, ethers, amides, and nitriles. These solvents may be used as a mixture thereof.

Examples of the preferred solvent include methylene chloride, tetrahydrofuran, N,N-dimethylformamide, and acetonitrile. More preferred is methylene chloride.

The amount of the solvent to be used is not particularly limited, but may be 1 to 50-fold amount (v/w) with respect to the compound of General Formula [A9].

The amount of the compound of General Formula [S9] to be used may be 1 to 10-fold molar excess and preferably 1 to 5-fold molar excess with respect to the compound of General Formula [A9].

It is preferred to add a reaction accelerator to this reaction.

The reaction accelerator may be, for example, 1H-tetrazole.

The amount of the reaction accelerator to be used may be 2 to 10-fold molar excess and preferably 2 to 5-fold molar excess with respect to the compound of General Formula [A9].

The reaction with the compound of General Formula [S9] may be carried out at −78° C. to 40° C. for 30 minutes to 24 hours.

The oxidizing agent to be used in this reaction may be, for example, meta-chloroperbenzoic acid.

The amount of the oxidizing agent to be used may be 1 to 5-fold molar excess and preferably 1 to 2-fold molar excess with respect to the compound of General Formula [A9].

The reaction with the oxidizing agent may be carried out at −78° C. to 40° C. for 30 minutes to 24 hours.

Second Step

The compound of Formula [1h] can be produced by deprotecting the compound of General Formula [A19].

This reaction may be carried out in accordance with the third step of production method A.

Third Step

As the compound of General Formula [S7], for example, L-alanine benzyl ester and isopropyl alcohol are known.

The compound of General Formula [1i] can be produced by reacting the compound of Formula [1h] with an activating agent, followed by reaction with the compound of General Formula [S7].

The solvent used in this reaction is not particularly limited as long as it does not affect the reaction and examples thereof include halogenated hydrocarbons, ethers, and aromatic hydrocarbons. These solvents may be used as a mixture thereof.

Examples of the preferred solvent include halogenated hydrocarbons. More preferred is methylene chloride.

The amount of the solvent to be used is not particularly limited, but may be 1 to 50-fold amount (v/w) with respect to the compound of Formula [1h].

The activating agent may be, for example, oxalyl chloride.

The amount of the activating agent to be used may be 1 to 5-fold molar excess and preferably 1 to 2-fold molar excess with respect to the compound of Formula [1h].

The reaction with the activating agent may be carried out at −78° C. to 40° C., preferably −78° C. to 0° C. for 30 minutes to 24 hours.

The amount of the compound of General Formula [S7] to be used may be 1 to 5-fold molar excess and preferably 2 to 3-fold molar excess with respect to the compound of Formula [1h].

It is preferred to add a reaction accelerator to this reaction.

The reaction accelerator may be, for example, N,N-dimethylformamide.

The amount of the reaction accelerator to be used may be 0.01 to 1-fold molar excess with respect to the compound of Formula [1h].

The reaction with the compound of General Formula [S7] may be carried out at 0° C. to 100° C., preferably 0° C. to 40° C. for 30 minutes to 24 hours.

The compounds obtained by the above-mentioned production methods can be derived into other compounds, for example, by a per se known reaction such as condensation, addition, oxidation, reduction, rearrangement, substitution, halogenation, dehydration, or hydrolysis, or by suitably combining these reactions.

In the case where an amino group, a hydroxyl group, or a carboxyl group is present in the compounds obtained by the above-mentioned production methods and the intermediates thereof, the reaction can be carried out by suitably rearranging those protective groups. Further, in the case where two or more protecting groups are present, a per se known reaction can be carried out to make selective deprotection.

With respect to the compounds used in the above-mentioned production methods, the compound capable of taking the form of a salt may be used as a salt. Examples of such a salt include the same salts as the salts of the thionucleoside derivative represented by General Formula [1] which is the thionucleoside derivative of the present invention described above.

In the case where isomers (for example, a tautomer, an optical isomer, and a geometric isomer) are present for the compounds used in the above-mentioned production methods, these isomers may also be used. In addition, in the case where solvates, hydrates and various forms of crystals are present, these solvates, hydrates and various forms of crystals may also be used.

In a pharmaceutical composition containing the thionucleoside derivative represented by General Formula [1] or the salt thereof according to the present invention, an additive commonly used in formulation may be appropriately mixed.

Examples of the additive include an excipient, a disintegrating agent, a binding agent, a lubricant, a flavoring agent, a colorant, an aromatizer, a surfactant, a coating agent, and a plasticizer.

Examples of the excipient include sugar alcohols such as erythritol, mannitol, xylitol, and sorbitol; sugars such as white sugar, powdered sugar, lactose, and glucose; cyclodextrins such as α-cyclodextrin, β-cyclodextrin, γ-cyclodextrin, hydroxypropyl β-cyclodextrin, and sodium sulfobutylether β-cyclodextrin; celluloses such as crystalline cellulose and microcrystalline cellulose; and starches such as a corn starch, a potato starch, and a pregelatinized starch.

Examples of the disintegrating agent include carmellose, carmellose calcium, croscarmellose sodium, sodium carboxymethyl starch, crospovidone, low-substituted hydroxypropyl cellulose, and a partially pregelatinized starch.

Examples of the binding agent include hydroxypropyl cellulose, carmellose sodium, and methylcellulose.

Examples of the lubricant include stearic acid, magnesium stearate, calcium stearate, talc, hydrated silicon dioxide, light anhydrous silicic acid, and sucrose fatty acid ester.

Examples of the flavoring agent include aspartame, saccharin, stevia, thaumatin, and acesulfame potassium.

Examples of the colorant include titanium dioxide, iron sesquioxide, yellow ferric oxide, black iron oxide, Food Red No. 102, Food Yellow No. 4, and Food Yellow No. 5.

Examples of the aromatizer include an essential oil such as an orange oil, a lemon oil, a peppermint oil, or a pine oil; an essence such as an orange essence or a peppermint essence; a flavor such as a cherry flavor, a vanilla flavor, or a fruit flavor; a powder fragrance such as an apple micron, a banana micron, a peach micron, a strawberry micron, or an orange micron; vanillin; and ethyl vanillin.

Examples of the surfactant include sodium lauryl sulfate, dioctyl sodium sulfosuccinate, polysorbate, and polyoxyethylene hydrogenated castor oil.

Examples of the coating agent include hydroxypropyl methyl cellulose, an aminoalkyl methacrylate copolymer E, an aminoalkyl methacrylate copolymer RS, ethyl cellulose, cellulose acetate phthalate, hydroxypropyl methyl cellulose phthalate, a methacrylic acid copolymer L, a methacrylic acid copolymer LD, and a methacrylic acid copolymer S.

Examples of the plasticizer include triethyl citrate, macrogol, triacetin, and propylene glycol.

These additives may be used alone or in combination of two or more thereof.

Although the blending amount of the additives is not particularly limited, the additives may be suitably blended such that the effects thereof are sufficiently exhibited depending on the respective purposes.

The pharmaceutical composition to which a mixture has been suitably added can be orally or parenterally administered according to a conventional method in the form of a tablet, a capsule, a powder, a syrup, a granule, a pill, a suspension, an emulsion, a solution, a powdered formulation, a suppository, an eye drop, a nasal drop, an ear drop, a patch, an ointment, an injection, or the like. It is preferred that the pharmaceutical composition is orally administered in the form of a tablet, a capsule, a powder, a syrup, a granule, a pill, a suspension, an emulsion, a solution, a powdered formulation, or the like.

The administration method, dosage, and administration frequency of the thionucleoside derivative represented by General Formula [1] or the salt thereof according to the present invention can be appropriately selected depending on a patient's age, body weight, and symptoms. Typically, for an adult, 0.01 to 1000 mg/kg/day may be administered orally or parenterally once or in several divided portions. It is preferred that 0.01 to 1000 mg/kg/day is administered orally once or in several divided portions.

EXAMPLES

Hereinafter, the present invention will be described with reference to Reference Examples and Examples, but the present invention is not limited thereto.

Unless otherwise specified, purification by column chromatography was carried out using an automated purification apparatus ISOLERA (manufactured by Biotage AB) or a medium-pressure liquid chromatograph YFLC-Wprep2XY.N (manufactured by Yamazen Corporation).

Unless otherwise specified, a SNAPKP-Sil Cartridge (manufactured by Biotage AB), or a HI-FLASH COLUMN W001, W002, W003, W004, or W005 (manufactured by Yamazen Corporation) was used as a carrier in silica gel column chromatography, and a SNAP KP-NH Cartridge (manufactured by Biotage AB) was used as a carrier in basic silica gel column chromatography.

In preparative thin layer chromatography, PLC glass plate silica gel $F_{60}$ (Merck Ltd.) was used.

In preparative reversed phase HPLC, a Waters 2998 Photodiode Array (PDA) Detector (manufactured by Waters Corporation), a Waters 600 Controller (manufactured by Waters Corporation), a Waters 2767 Sample Manager (manufactured by Waters Corporation), and a YMC-Actus ProC18, 30×50 mm column (manufactured by YMC Co., Ltd.) were used.

The mixing ratio in the eluent was a volume ratio. For example, "hexane:ethyl acetate gradient elution=100:0 to 50:50" means that an eluent of 100% hexane/0% ethyl acetate was finally changed to an eluent of 50% hexane/50% ethyl acetate.

MS spectra were measured using an ACQUITY SQD LC/MS System (manufactured by Waters Corporation, ionization method: Electro Spray Ionization (ESI) method), an M-8000 type (manufactured by Hitachi, Ltd., ionization method: ESI method), or an LCMS-2010EV (manufactured by Shimadzu Corporation, ionization method: method of carrying out ESI and Atmospheric Pressure Chemical Ionization (APCI) at the same time).

NMR spectra were measured using a Bruker AV300 (manufactured by Bruker Corporation, 300 MHz) and using tetramethylsilane as an internal standard, and all δ values were shown in ppm.

The retention time (RT) was measured using a SQD (manufactured by Waters Corporation), and was shown in minutes (min).

Column: BEHC 18 1.7 μm, 2.1×30 mm (manufactured by Waters Corporation)

Solvent: liquid A: 0.1% formic acid-water liquid B: 0.1% formic acid-acetonitrile Gradient cycle: 0.00 min (liquid A/liquid B=95/5), 2.00 min (liquid A/liquid B=5/95), 3.00 min (liquid A/liquid B=5/95), 3.01 min (liquid A/liquid B=100/0), 3.80 min (liquid A/liquid B=100/0)

Flow rate: 0.5 mL/min

Column temperature: room temperature

Detection wavelength: 254 nm

Abbreviations in individual Examples have the following meanings.

Ac: acetyl

Boc: tert-butoxycarbonyl

TBDPS: tert-butyldiphenylsilyl

Ts: tosyl (para-toluenesulfonyl)

RT (min): retention time (min)

DMSO-$d_6$: deuterated dimethyl sulfoxide

\*: bonding position

Reference Example 1

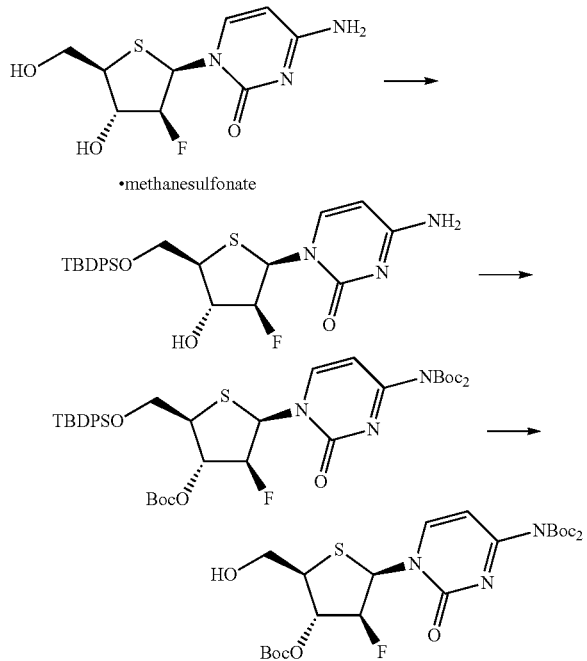

First Step

Imidazole (5.70 g) and tert-butyldiphenylchlorosilane (11.5 g) were added to a mixture of methanesulfonate (10.0 g) of 4-amino-1-((2R,3S,4S,5R)-3-fluoro-4-hydroxy-5-(hydroxymethyl)tetrahydrothiophen-2-yl)pyrimidin-2(1H)-one and N,N-dimethylformamide (100 mL) which was then stirred at room temperature for 1.5 hours. Water was added to the reaction liquid which was then extracted with ethyl acetate, and the organic layer was dried over anhydrous sodium sulfate. The solvent was distilled off under reduced pressure to give 4-amino-1-((2R,3S,4S,5R)-5-(((tert-butyldiphenylsilyl)oxy)methyl)-3-fluoro-4-hydroxytetrahydrothiophen-2-yl)pyrimidin-2(1H)-one (13.8 g) as a colorless oil.

MS (ESI m/z): 500 (M+H)
RT (min): 1.50

Second Step

N,N-dimethyl-4-aminopyridine (100 mg) and triethylamine (12.5 mL) were added to a mixture of 4-amino-1-((2R,3S,4S,5R)-5-(((tert-butyldiphenylsilyl)oxy)methyl)-3-fluoro-4-hydroxytetrahydrothiophen-2-yl)pyrimidin-2(1H)-one (13.8 g) obtained in the first step and methylene chloride (100 mL), and a mixture of di-tert-butyldicarbonate (20 mL) and methylene chloride (20 mL) was slowly added dropwise thereto at room temperature. After stirring at room temperature for 6 hours, triethylamine (5.0 mL) and di-tert-butyldicarbonate (5.0 mL) were added thereto, followed by stirring for 20 minutes. Triethylamine (3.0 mL) and di-tert-butyldicarbonate (3.0 mL) were added to the reaction liquid which was then stirred for 30 minutes, and the solvent was distilled off under reduced pressure. The resulting residue was purified by silica gel column chromatography (hexane:ethyl acetate=100:0 to 70:30) to give tert-butyl tert-butoxycarbonyl(1-((2R,3S,4S,5R)-4-((tert-butoxycarbonyl)oxy)-5-(((tert-butyldiphenylsilyl)oxy)methyl)-3-fluorotetrahydrothiophen-2-yl)-2-oxo-1,2-dihydropyrimidin-4-yl)carbamate (21.8 g) as a white solid.

MS (ESI m/z): 800 (M+H)
RT (min): 2.52

Third Step

A mixture of acetic acid (3.0 mL) and a 1 mol/L tetrabutylammonium fluoride/tetrahydrofuran solution (30 mL) was added to a mixture of tert-butyl tert-butoxycarbonyl(1-((2R,3S,4S,5R)-4-((tert-butoxycarbonyl)oxy)-5-(((tert-butyldiphenylsilyl)oxy)methyl)-3-fluorotetrahydrothiophen-2-yl)-2-oxo-1,2-dihydropyrimidin-4-yl)carbamate (14.8 g) and tetrahydrofuran (30 mL) which was then stirred at room temperature for 45 minutes. The solvent was distilled off under reduced pressure and the resulting residue was purified by silica gel column chromatography (hexane:ethyl acetate=100:0 to 50:50) to give tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (7.50 g) as a white solid.

MS (ESI m/z): 562 (M+H)
RT (min): 1.71

Reference Example 2

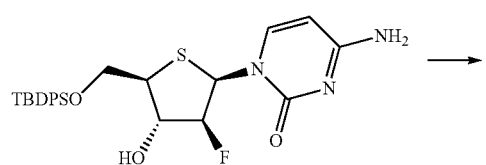

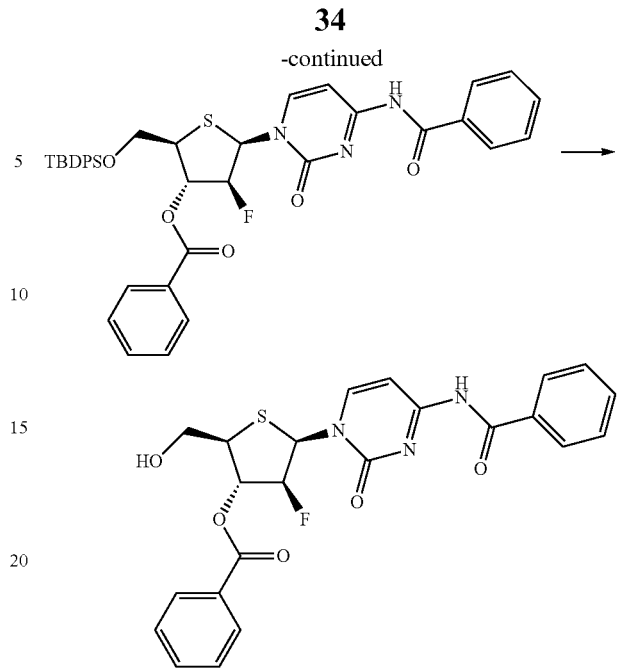

First Step

Benzoyl chloride (7.94 mL) was added under ice-cooling to a mixture of 4-amino-1-((2R,3S,4S,5R)-5-(((tert-butyldiphenylsilyl)oxy)methyl)-3-fluoro-4-hydroxytetrahydrothiophen-2-yl)pyrimidin-2(1H)-one (11.5 g) and pyridine (115 mL) which was then stirred at room temperature for 1 hour. The solvent was distilled off under reduced pressure, and water was added to the resulting residue which was then extracted with ethyl acetate. The organic layer was washed with water and an aqueous saturated sodium chloride solution and dried over anhydrous sodium sulfate. The solvent was distilled off under reduced pressure and the resulting residue was purified by silica gel column chromatography (hexane:ethyl acetate=90:10 to 0:100) to give (2R,3S,4S,5R)-5-(4-benzamido-2-oxopyrimidin-1(2H)-yl)-2-(((tert-butyldiphenylsilyl)oxy)methyl)-4-fluorotetrahydrothiophen-3-yl benzoate (8.48 g) as a white solid.

MS (ESI m/z): 708 (M+H)
RT (min): 2.28

Second Step

A 1 mol/L tetrabutylammonium fluoride/tetrahydrofuran solution (24 mL) was added to a mixture of (2R,3S,4S,5R)-5-(4-benzamido-2-oxopyrimidin-1(2H)-yl)-2-(((tert-butyldiphenylsilyl)oxy)methyl)-4-fluorotetrahydrothiophen-3-yl benzoate (8.48 g) and tetrahydrofuran (48 mL) which was then stirred at room temperature for 30 minutes. Methylene chloride was added to the reaction liquid, and the organic layer was washed with water and dried over anhydrous sodium sulfate. The solvent was distilled off under reduced pressure and the resulting residue was purified by silica gel column chromatography (hexane:ethyl acetate=90:10 to 0:100) to give (2R,3S,4S,5R)-5-(4-benzamido-2-oxopyrimidin-1(2H)-yl)-4-fluoro-2-(hydroxymethyl)tetrahydrothiophen-3-yl benzoate (5.56 g) as a white solid.

$^1$H-NMR (DMSO-$d_6$) δ: 11.36 (s, 1H), 8.71 (d, 1H, J=7.6 Hz), 8.05-7.99 (m, 4H), 7.76-7.45 (m, 7H), 6.60 (dd, 1H, J=12.4, 5.4 Hz), 5.86-5.79 (m, 1H), 5.71-5.48 (m, 2H), 3.82-3.68 (m, 3H).

MS (ESI m/z): 470 (M+H)
RT (min): 1.24

Reference Example 3

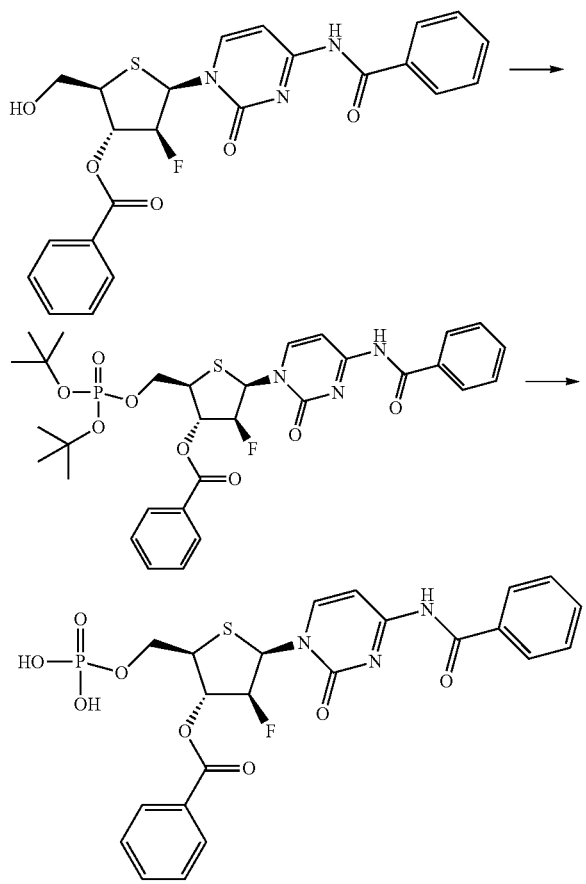

First Step

Di-tert-butyl N,N-diisopropyl phosphoramidite (12.8 mL) was added to a mixture of (2R,3S,4S,5R)-5-(4-benzamido-2-oxopyrimidin-1(2H)-yl)-4-fluoro-2-(hydroxymethyl)tetrahydrothiophen-3-yl benzoate (9.50 g), 1H-tetrazole (4.30 g) and methylene chloride (190 mL) which was then stirred at room temperature for 30 minutes. meta-Chloroperbenzoic acid (7.00 g) was added thereto at −40° C., followed by stirring for 30 minutes under ice-cooling. Under ice-cooling, a mixture of sodium sulfite (7.70 g) and water (100 mL) was added thereto, followed by stirring at room temperature for 30 minutes. The water layer was removed, and the organic layer was dried over anhydrous sodium sulfate. The solvent was distilled off under reduced pressure and the resulting residue was purified by silica gel column chromatography (hexane:ethyl acetate=50:50 to 20:80) to give (2R,3S,4S,5R)-5-(4-benzamido-2-oxopyrimidin-1(2H)-yl)-2-(((di-tert-butoxyphosphoryl)oxy) methyl)-4-fluorotetrahydrothiophen-3-yl benzoate (4.93 g) as a white solid.

$^1$H-NMR (DMSO-d$_6$) δ: 11.38 (s, 1H), 8.56 (d, 1H, J=7.9 Hz), 8.05-8.00 (m, 4H), 7.76-7.71 (m, 1H), 7.67-7.45 (m, 6H), 6.62 (dd, 1H, J=14.4, 5.1 Hz), 5.92-5.83 (m, 1H), 5.76-5.53 (m, 1H), 4.37-4.17 (m, 2H), 3.97-3.89 (m, 1H), 1.42 (s, 9H), 1.41 (s, 9H).

MS (ESI m/z): 662 (M+H)
RT (min): 1.71

Second Step

A mixture of (2R,3S,4S,5R)-5-(4-benzamido-2-oxopyrimidin-1(2H)-yl)-2-((((di-tert-butoxyphosphoryl)oxy) methyl)-4-fluorotetrahydrothiophen-3-yl benzoate (3.50 g) and a 4.0 mol/L hydrogen chloride/1,4-dioxane solution (27 mL) was stirred at room temperature for 30 minutes. The solvent was distilled off under reduced pressure and the resulting residue was washed with ethyl acetate to give (2R,3S,4S,5R)-5-(4-benzamido-2-oxopyrimidin-1(2H)-yl)-4-fluoro-2-((phosphonooxy)methyl) tetrahydrothiophen-3-yl benzoate (2.63 g) as a white solid.

$^1$H-NMR (DMSO-d$_6$) δ: 8.61 (d, 1H, J=7.6 Hz), 8.05-8.00 (m, 4H), 7.77-7.70 (m, 1H), 7.68-7.49 (m, 5H), 7.45 (d, 1H, J=7.6 Hz), 6.62 (dd, 1H, J=13.5, 5.3 Hz), 5.87-5.80 (m, 1H), 5.74-5.54 (m, 1H), 4.31-4.12 (m, 2H), 3.91 (dd, 1H, J=11.1, 6.1 Hz).

MS (ESI m/z): 550 (M+H)
RT (min): 0.92

Reference Example 4

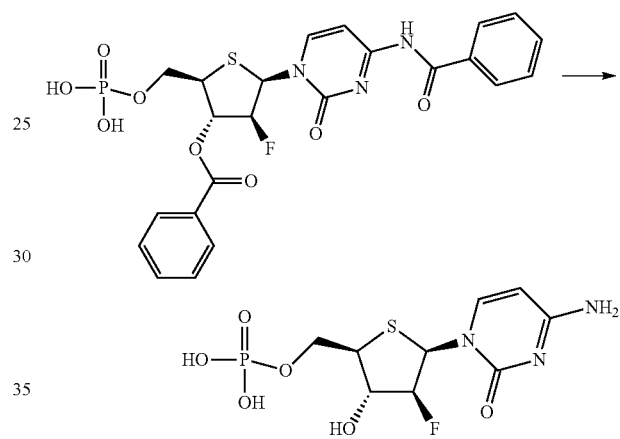

A mixture of (2R,3S,4S,5R)-5-(4-benzamido-2-oxopyrimidin-1(2H)-yl)-4-fluoro-2-((phosphonooxy)methyl) tetrahydrothiophen-3-yl benzoate (1.70 g) and a 7.0 mol/L ammonia/methanol solution (100 mL) was stirred at room temperature for 17 hours. The insoluble matter was separated by filtration and the solvent was distilled off under reduced pressure. The resulting residue was washed with acetone to give ((2R,3S,4S,5R)-5-(4-amino-2-oxopyrimidin-1(2H)-yl)-4-fluoro-3-hydroxytetrahydrothiophen-2-yl) methyl dihydrogen phosphate (733 mg) as a white solid.

$^1$H-NMR (DMSO-d$_6$) δ: 8.00 (d, 1H, J=7.6 Hz), 7.31 (s, 1H), 7.17 (s, 1H), 6.42 (dd, 1H, J=11.2, 5.3 Hz), 5.80 (d, 1H, J=7.6 Hz), 5.04-4.80 (m, 1H), 4.34-4.22 (m, 1H), 3.97-3.79 (m, 2H), 3.34-3.26 (m, 1H).

MS (ESI m/z): 342 (M+H)
RT (min): 0.19

Reference Example 5

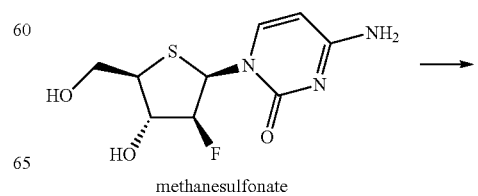

methanesulfonate

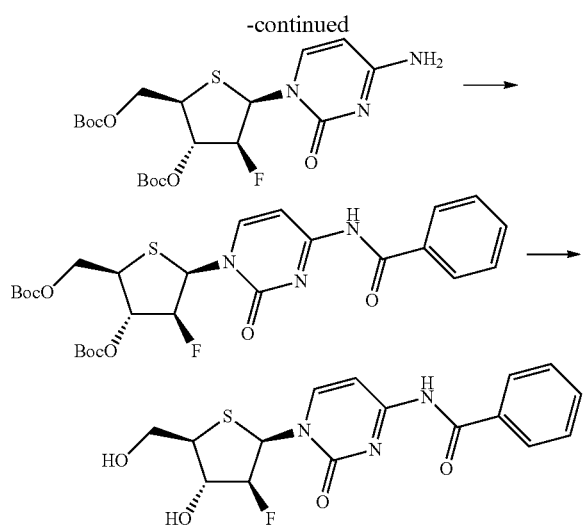

First Step

To a mixture of methanesulfonate (2.40 g) of 4-amino-1-((2R,3S,4S,5R)-3-fluoro-4-hydroxy-5-(hydroxymethyl)tetrahydrothiophen-2-yl)pyrimidin-2(1H)-one and a 1.0 mol/L aqueous potassium hydroxide solution (160 mL), a mixture of di-tert-butyldicarbonate (17.4 g) and 1,4-dioxane (160 mL) was slowly added over 20 minutes. After stirring at room temperature for 3.5 hours following the completion of the dropwise addition, a 1.0 mol/L aqueous potassium hydroxide solution (80 mL) and di-tert-butyldicarbonate (8.72 g) were added to the reaction liquid which was then stirred at room temperature for 30 minutes. After standing at room temperature for 15 hours, the reaction liquid was extracted with ethyl acetate. The organic layer was washed with water and an aqueous saturated sodium chloride solution and dried over anhydrous sodium sulfate. The solvent was distilled off under reduced pressure and the resulting residue was purified by silica gel column chromatography (ethyl acetate:methanol=100:0 to 90:10) to give tert-butyl ((2R,3S,4S,5R)-3-((tert-butoxycarbonyl)oxy)-5-(4-amino-2-oxopyrimidin-1(2H)-yl)-4-fluorotetrahydrothiophen-2-yl)methyl carbonate (1.35 g) as a colorless oil.

MS (ESI m/z): 462 (M+H)

RT (min): 1.29

Second Step

Benzoyl chloride (18.8 µL) was added to a mixture of tert-butyl ((2R,3S,4S,5R)-3-((tert-butoxycarbonyl)oxy)-5-(4-amino-2-oxopyrimidin-1(2H)-yl)-4-fluorotetrahydrothiophen-2-yl)methyl carbonate (50.0 mg), N,N-diisopropylethylamine (36.7 µL) and methylene chloride (1.0 mL) which was then stirred at room temperature for 18 hours. An aqueous saturated sodium hydrogen carbonate solution was added to the reaction liquid which was then extracted with ethyl acetate and dried over anhydrous sodium sulfate. The solvent was distilled off under reduced pressure. Ethyl acetate was added to the resulting residue, and the precipitated solid was collected by filtration to give tert-butyl (((2R,3S,4S,5R)-3-((tert-butoxycarbonyl)oxy)-4-fluoro-5-(4-benzamido-2-oxopyrimidin-1(2H)-yl)tetrahydrothiophen-2-yl)methyl) carbonate (38.0 mg) as a white solid.

MS (ESI m/z): 566 (M+H)

RT (min): 1.78

Third Step

Trifluoroacetic acid (1.0 mL) was added to tert-butyl (((2R,3S,4S,5R)-3-((tert-butoxycarbonyl)oxy)-4-fluoro-5-(4-benzamido-2-oxopyrimidin-1(2H)-yl)tetrahydrothiophen-2-yl)methyl) carbonate (31.0 mg) which was then stirred at room temperature for 3 hours. The solvent was distilled off under reduced pressure. Ethyl acetate (1.0 mL) and an aqueous saturated sodium hydrogen carbonate solution (1.0 mL) were added to the resulting residue which was then stirred. The water layer was removed, the organic layer was dried over anhydrous sodium sulfate, and the solvent was distilled off under reduced pressure. The resulting residue was purified by silica gel column chromatography (chloroform:methanol=95:5 to 88:12) to give N-(1-((2R,3S,4S,5R)-3-fluoro-4-hydroxy-5-(hydroxymethyl)tetrahydrothiophen-2-yl)-2-oxo-1,2-dihydropyrimidin-4-yl)benzamide (9.2 mg) as a white solid.

$^1$H-NMR (DMSO-$d_6$) δ: 11.31 (s, 1H), 8.63 (d, 1H, J=7.6 Hz), 8.01 (d, 2H, J=7.6 Hz), 7.67-7.59 (m, 1H), 7.56-7.47 (m, 2H), 7.40 (d, 1H, J=7.3 Hz), 6.47 (dd, 1H, J=10.9, 5.6 Hz), 5.96 (d, 1H, J=5.3 Hz), 5.38-5.30 (m, 1H), 5.20-4.95 (m, 1H), 4.34-4.21 (m, 1H), 3.83-3.62 (m, 2H), 3.30-3.21 (m, 1H).

MS (ESI m/z): 366 (M+H)

RT (min): 0.88

Reference Example 6

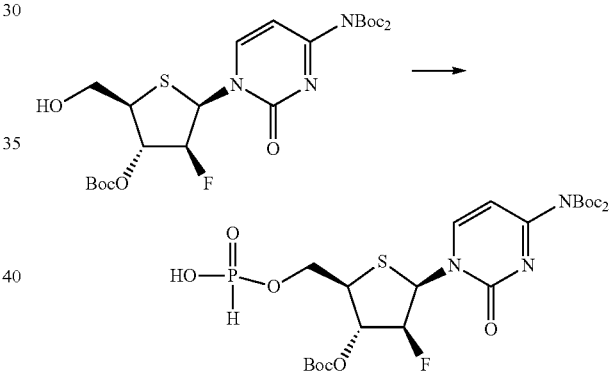

A mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (400 mg) and pyridine (1.8 mL) was added to a mixture of diphenyl phosphite (272 µL) and pyridine (1.8 mL) which was then stirred at room temperature for 10 minutes. A mixture of water (712 µL) and triethylamine (712 µL) was added thereto, followed by stirring at room temperature for 5 minutes. The solvent was distilled off under reduced pressure and the resulting residue was purified by silica gel column chromatography (chloroform:methanol=100:0 to 60:40) to give ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl hydrogen phosphonate (283 mg) as a colorless oil.

MS (ESI m/z): 626 (M+H)

RT (min): 1.26

Reference Example 7

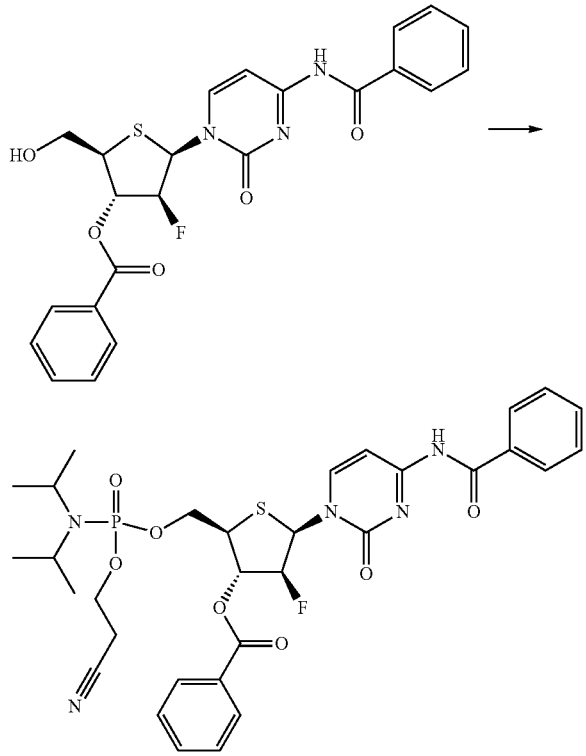

1H-tetrazole (870 mg) was added to a mixture of (2R,3S,4S,5R)-5-(4-benzamido-2-oxopyrimidin-1(2H)-yl)-4-fluoro-2-(hydroxymethyl)tetrahydrothiophen-3-yl benzoate (3.90 g), 2-cyanoethyl N,N,N',N'-tetraisopropylphosphorodiamidite (5.00 g), N,N-diisopropylethylamine (2.2 mL), acetonitrile (28 mL) and tetrahydrofuran (28 mL) which was then stirred at room temperature for 20 minutes. Water was added to the reaction liquid which was then extracted with ethyl acetate, and the organic layer was dried over anhydrous magnesium sulfate. Then, the solvent was distilled off under reduced pressure. The resulting residue was purified by silica gel column chromatography (hexane:ethyl acetate=50:50 to 0:100) to give a white solid. The resulting white solid was dissolved in methanol and ethyl acetate, and hexane was added to result in precipitation, thereby affording (2R,3S,4S,5R)-5-(4-benzamido-2-oxopyrimidin-1(2H)-yl)-2-((((2-cyanoethoxy)(diisopropylamino)phosphoryl)oxy)methyl)-4-fluorotetrahydrothiophen-3-yl benzoate (1.50 g) as a white solid.

$^1$H-NMR (DMSO-$d_6$) δ: 11.37 (s, 1H), 8.70-8.54 (m, 1H), 8.07-7.39 (m, 10H), 6.66-6.55 (m, 1H), 5.93-5.80 (m, 1H), 5.76-5.66 (m, 1H), 5.60-5.48 (m, 1H), 4.12-3.70 (m, 5H), 3.65-3.48 (m, 2H), 2.85-2.74 (m, 2H), 1.18-1.09 (m, 12H).

Reference Example 8-1

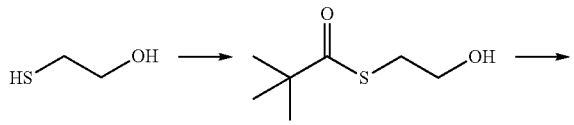

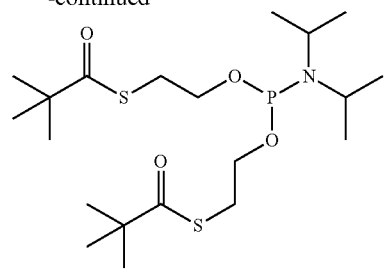

First Step

To a mixture of 2-mercaptoethanol (1.5 mL), triethylamine (4.0 mL) and methylene chloride (55 mL), pivaloyl chloride (2.64 mL) was slowly added dropwise at −78° C. over 1 hour, followed by stirring at room temperature for 1 hour. Water (30 mL) was added to the reaction liquid which was then stirred for 30 minutes and extracted with ethyl acetate, and the organic layer was dried over anhydrous sodium sulfate. The solvent was distilled off under reduced pressure to give S-(2-hydroxyethyl) 2,2-dimethylpropanethioate (3.69 g) as a colorless oil.

$^1$H-NMR (CDCl$_3$) δ: 3.76 (t, 2H, J=6.1 Hz), 3.06 (t, 2H, J=6.1 Hz), 1.25 (s, 9H).

Second Step

A mixture of 1,1-dichloro-N,N-diisopropylphosphineamine (1.01 g) and tetrahydrofuran (35 mL) was added dropwise at −78° C. to a mixture of S-(2-hydroxyethyl) 2,2-dimethylpropanethioate (1.62 g), triethylamine (3.0 mL) and tetrahydrofuran (25 mL) which was then stirred at room temperature for 2 hours. The insoluble matter was separated by filtration, and the solvent was distilled off under reduced pressure. The resulting residue was purified by silica gel column chromatography (hexane:ethyl acetate=96:4 to 75:25) to give S,S'-((((diisopropylamino)phosphinediyl)bis(oxy))bis(ethane-2,1-diyl)) bis(2,2-dimethylpropanethioate) (751 mg) as a colorless oil.

$^1$H-NMR (CDCl$_3$) δ: 4.24 (t, 4H, J=7.3 Hz), 3.79-3.59 (m, 2H), 2.89-2.76 (m, 4H), 1.27-1.15 (m, 30H).

Reference Example 8-2

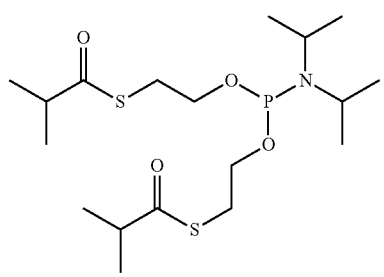 [SMILES: CC(C)C(=O)SCCOP(OCCSC(=O)C(C)C)N(C(C)C)C(C)C]

The following compound was obtained in the same manner as in Reference Example 8-1.

S,S'-((((diisopropylamino)phosphinediyl)bis(oxy))bis(ethane-2,1-diyl)) bis(2-methylpropanethioate)

$^1$H-NMR (CDCl$_3$) δ: 4.25 (t, 4H, J=6.9 Hz), 2.89-2.77 (m, 4H), 2.63-2.47 (m, 4H), 1.24-1.14 (m, 24H).

Reference Example 8-3

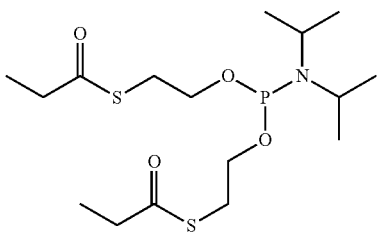 [SMILES: CCC(=O)SCCOP(OCCSC(=O)CC)N(C(C)C)C(C)C]

The following compound was obtained in the same manner as in Reference Example 8-1.

S,S'-(((((diisopropylamino)phosphinediyl)bis(oxy))bis(ethane-2,1-diyl)) dipropanethioate $^1$H-NMR (CDCl$_3$) δ: 4.26 (t, 4H, J=6.9 Hz), 3.79-3.60 (m, 2H), 2.90-2.73 (m, 4H), 1.19 (d, 12H, J=6.6 Hz), 1.14 (t, 6H, J=7.6 Hz).

Reference Example 9-1

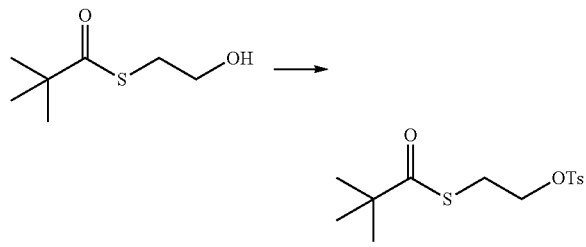

Para-toluenesulfonyl chloride (881 mg) was added to a mixture of S-(2-hydroxyethyl) 2,2-dimethylpropanethioate (500 mg), pyridine (0.5 mL) and methylene chloride (5.0 mL) which was then stirred at room temperature for 19 hours. An aqueous saturated sodium hydrogen carbonate solution (5.0 mL) was added to the reaction liquid which was then stirred for 1.5 hours and extracted with ethyl acetate. The organic layer was washed with 1.0 mol/L hydrochloric acid, water and an aqueous saturated sodium chloride solution, and dried over anhydrous sodium sulfate. The solvent was distilled off under reduced pressure to give S-(2-(tosyloxy)ethyl) 2,2-dimethylpropanethioate (762 mg) as a colorless oil.

$^1$H-NMR (CDCl$_3$) δ: 7.80 (d, 2H, J=8.3 Hz), 7.35 (d, 2H, J=8.3 Hz), 4.08 (t, 2H, J=6.6 Hz), 3.08 (t, 2H, J=6.6 Hz), 2.45 (s, 3H), 1.18 (s, 9H).

Reference Example 9-2

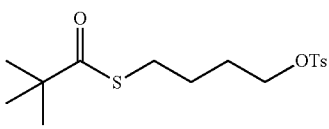 [SMILES: Cc1ccc(S(=O)(=O)OCCCCSC(=O)C(C)(C)C)cc1]

The following compound was obtained in the same manner as in Reference Example 9-1.

S-(4-(tosyloxy)butyl) 2,2-dimethylpropanethioate
MS (ESI m/z): 345 (M+H)
RT (min): 1.90

Reference Example 10-1

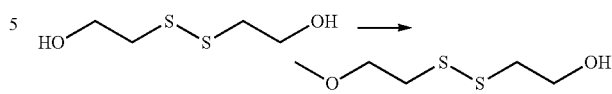

Under a nitrogen atmosphere, 60% sodium hydride (130 mg) was added to a mixture of 2,2'-disulfanediyldiethanol (500 mg) and tetrahydrofuran (5.0 mL) which was then stirred at room temperature for 10 minutes. Methyl iodide (202 μL) was added to the reaction liquid which was then stirred for 3 hours, and water was added thereto, followed by extraction with ethyl acetate. The organic layer was washed with an aqueous saturated sodium chloride solution and dried over anhydrous sodium sulfate, and the solvent was distilled off under reduced pressure. The resulting residue was purified by silica gel column chromatography (hexane: ethyl acetate=72:28 to 51:49) to give 2-((2-methoxyethyl)disulfanyl)ethanol (187 mg) as a colorless oil.

$^1$H-NMR (CDCl$_3$) δ: 3.95-3.85 (m, 2H), 3.67 (t, 2H, J=6.3 Hz), 3.39 (s, 3H), 2.91 (t, 2H, J=6.3 Hz), 2.88 (t, 2H, J=5.6 Hz), 2.23-2.15 (m, 1H).

Reference Example 10-2

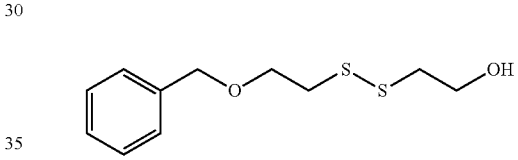

The following compound was obtained in the same manner as in Reference Example 10-1.

2-((2-(benzyloxy)ethyl)disulfanyl)ethanol $^1$H-NMR (CDCl$_3$) δ: 7.39-7.27 (m, 5H), 4.56 (s, 2H), 3.92-3.81 (m, 2H), 3.75 (t, 2H, J=6.3 Hz), 2.94 (t, 2H, J=6.3 Hz), 2.83 (t, 2H, J=5.9 Hz), 2.12-1.95 (m, 1H).

Reference Example 11-1

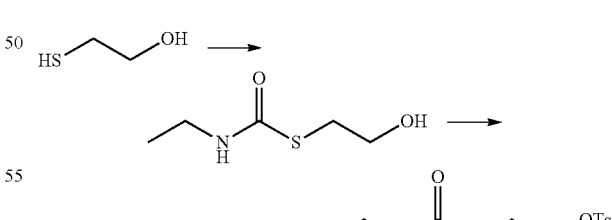

First Step

Ethyl isocyanate (1.1 mL) was added at −78° C. to a mixture of 2-mercaptoethanol (980 μL), triethylamine (3.9 mL) and toluene (14 mL) which was then stirred at room temperature for 1 hour. The solvent was distilled off under reduced pressure to give S-(2-hydroxyethyl) ethylcarbamothioate (2.10 g).

Second Step

Under ice-cooling, para-toluenesulfonyl chloride (2.00 g) was added to a mixture of S-(2-hydroxyethyl) ethylcarbamothioate (1.05 g), pyridine (1.1 mL) and methylene chloride (14 mL) which was then stirred at room temperature for 18 hours. An aqueous saturated sodium hydrogen carbonate solution was added to the reaction liquid which was then stirred for 30 minutes and extracted with ethyl acetate. The organic layer was washed with water and an aqueous saturated sodium chloride solution and dried over anhydrous sodium sulfate. The solvent was distilled off under reduced pressure to give 2-((ethylcarbamoyl)thio)ethyl 4-methylbenzene sulfonate (470 mg).

MS (ESI m/z): 304 (M+H)
RT (min): 1.35

Reference Example 11-2

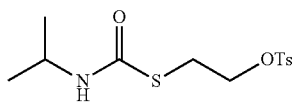 [SMILES: Cc1ccc(S(=O)(=O)OCCSC(=O)NC(C)C)cc1]

The following compound was obtained in the same manner as in Reference Example 11-1.

2-((isopropylcarbamoyl)thio)ethyl 4-methylbenzene sulfonate
MS (ESI m/z): 318 (M+H)
RT (min): 1.46

Reference Example 11-3

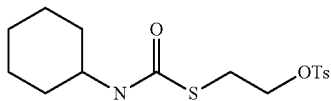

The following compound was obtained in the same manner as in Reference Example 11-1.

2-((cyclohexylcarbamoyl)thio)ethyl 4-methylbenzene sulfonate
MS (ESI m/z): 358 (M+H)
RT (min): 1.60

Reference Example 12-1

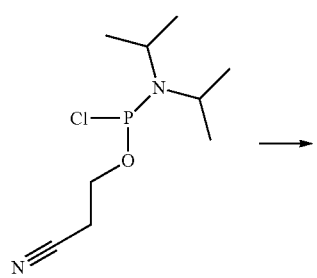

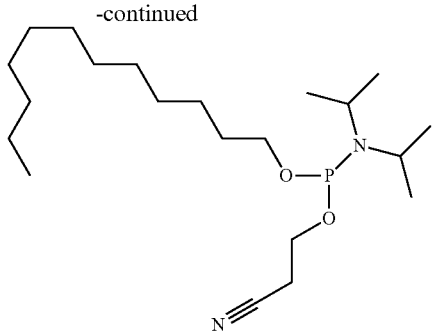

Under a nitrogen atmosphere, a mixture of N,N-diisopropylethylamine (172 µL), 1-dodecanol (224 µL) and diethyl ether (6.0 mL) was added dropwise under ice-cooling to a mixture of 2-cyanoethyl N,N-diisopropylchlorophosphoramidite (223 µL) and diethyl ether (4.0 mL). After stirring at room temperature for 2.5 hours, the insoluble matter was separated by filtration and the solvent was distilled off under reduced pressure to give 2-cyanoethyl dodecyl N,N-diisopropylphosphoramidite (298 mg) as a colorless oil.

Reference Example 12-2

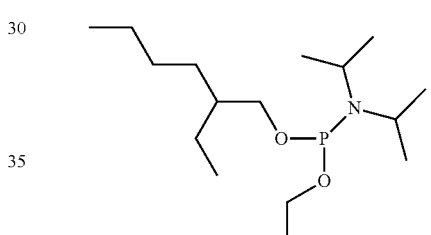

The following compound was obtained in the same manner as in Reference Example 12-1.

2-cyanoethyl 2-ethylhexyl diisopropyl phosphoramidite

Reference Example 12-3

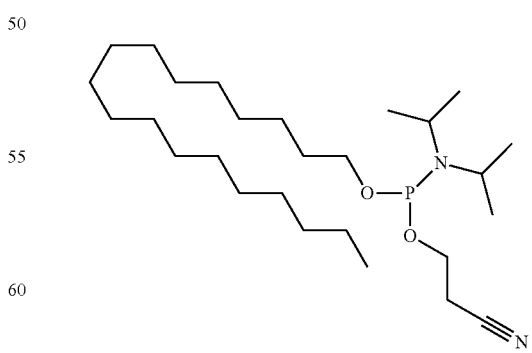

The following compound was obtained in the same manner as in Reference Example 12-1.

2-cyanoethyl octadecyl diisopropylphosphoramidite

Reference Example 13-1

Pyridine (4.8 mL) was added under ice-cooling to a mixture of 4-nitrophenyl phosphorodichloridate (5.12 g) and tetrahydrofuran (51 mL). After stirring for 30 minutes under ice-cooling, 1,3-propanediol (1.52 g) was added under ice-cooling, followed by stirring at room temperature for 1 hour. An aqueous saturated ammonium chloride solution was added thereto, followed by extraction with ethyl acetate. The organic layer was washed with an aqueous saturated sodium chloride solution and dried over anhydrous sodium sulfate, and then the solvent was distilled off under reduced pressure. The resulting residue was purified by silica gel column chromatography (hexane:ethyl acetate=80:20 to 20:80) to give 2-(4-nitrophenoxy)-1,3,2-dioxaphosphinane 2-oxide (2.74 g) as a white solid.

MS (ESI m/z): 260 (M+H)
RT (min): 0.98

Reference Example 13-2

The following compound was obtained in the same manner as in Reference Example 13-1.

(2RS,4R)-2-(4-nitrophenoxy)-4-phenyl-1,3,2-dioxaphosphinane 2-oxide

MS (ESI m/z): 336 (M+H)
RT (min): 1.39

Reference Example 13-3

The following compound was obtained in the same manner as in Reference Example 13-1.

(2RS,4RS)-4-(3-chlorophenyl)-2-(4-nitrophenoxy)-1,3,2-dioxaphosphinane 2-oxide

MS (ESI m/z): 370 (M+H)
RT (min): 1.51

Reference Example 13-4

The following compound was obtained in the same manner as in Reference Example 13-1.

(RS)-2-(4-nitrophenoxy)-4H-benzo[d][1,3,2]dioxaphosphinine 2-oxide

MS (ESI m/z): 308 (M+H)
RT (min): 1.36

Reference Example 13-5

The following compound was obtained in the same manner as in Reference Example 13-1.

(RS)-8-methoxy-2-(4-nitrophenoxy)-4H-benzo[d][1,3,2]dioxaphosphinine 2-oxide

MS (ESI m/z): 338 (M+H)
RT (min): 1.34

Reference Example 14-1

Imidazole (8.30 g) was added to a mixture of ethylene glycol (11.4 mL), tert-butyldiphenylchlorosilane (10.6 mL) and methylene chloride (80 mL) which was then stirred at room temperature for 25 minutes. Water was added to the reaction liquid which was then extracted with methylene chloride, the organic layer was dried over anhydrous magnesium sulfate, and then the solvent was distilled off under reduced pressure. The resulting residue was purified by silica gel column chromatography (hexane:ethyl acetate=95:5 to 60:40) to give 2-((tert-butyldiphenylsilyl)oxy)ethanol (3.87 g) as a colorless oil.

$^1$H-NMR (CDCl$_3$) δ: 7.74-7.33 (m, 10H), 3.80-3.73 (m, 2H), 3.72-3.64 (m, 2H), 1.07 (s, 9H).

Reference Example 14-2

The following compound was obtained in the same manner as in Reference Example 14-1.

2((2-((tert-butyldiphenylsilyl)oxy)ethyl)disulfanyl)ethanol

¹H-NMR (CDCl₃) δ: 7.70-7.36 (m, 10H), 3.90 (t, 2H, J=6.6 Hz), 3.87-3.79 (m, 2H), 2.85 (t, 2H, J=6.6 Hz), 2.75 (t, 2H, J=5.9 Hz), 1.90 (t, 1H, J=5.9 Hz), 1.06 (s, 9H).

Reference Example 15

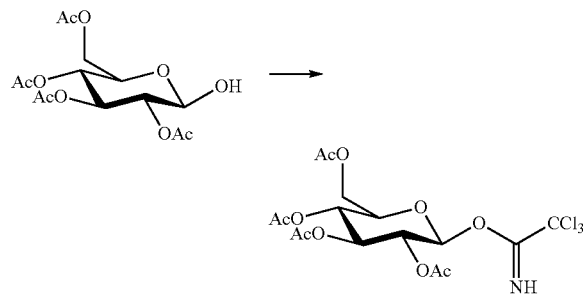

Trichloroacetonitrile (115 μL) was added under ice-cooling to a mixture of 2,3,4,6-tetra-O-acetyl-β-D-glucopyranose (100 mg) and methylene chloride (1.5 mL) which was then stirred for 5 minutes. Diazabicycloundecene (10 μL) was added to the reaction liquid which was then stirred at room temperature for 40 minutes, and the solvent was distilled off under reduced pressure. The resulting residue was purified by silica gel column chromatography (hexane:ethyl acetate=80:20 to 65:35) to give (2R,3R,4S,5R,6S)-2-(acetoxymethyl)-6-(2,2,2-trichloro-1-iminoethoxy)tetrahydro-2H-pyran-3,4,5-triyl triacetate (95.0 mg) as a colorless oil.

¹H-NMR (CDCl₃) δ: 8.70 (s, 1H), 6.56 (d, 1H, J=4.0 Hz), 5.62-5.51 (m, 1H), 5.22-5.07 (m, 2H), 4.33-4.06 (m, 3H), 2.12-1.96 (m, 12H).

Reference Example 16-1

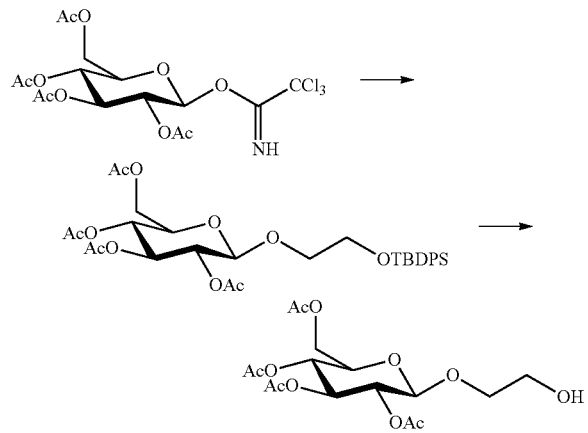

First Step

A boron trifluoride diethyl ether complex (54 μL) was added under ice-cooling to a mixture of (2R,3R,4S,5R,6S)-2-(acetoxymethyl)-6-(2,2,2-trichloro-1-iminoethoxy)tetrahydro-2H-pyran-3,4,5-triyl triacetate (525 mg), 2-((tert-butyldiphenylsilyl)oxy)ethanol (318 mg), a molecular sieve 4 A and methylene chloride (5.3 mL) which was then stirred at room temperature for 10 minutes. Water was added to the reaction liquid which was then extracted with methylene chloride. The organic layer was dried over anhydrous magnesium sulfate and the solvent was distilled off under reduced pressure. The resulting residue was purified by silica gel column chromatography (hexane:ethyl acetate=80:20 to 50:50) to give (2R,3R,4S,5R,6R)-2-(acetoxymethyl)-6-(2-((tert-butyldiphenylsilyl)oxy)ethoxy)tetrahydro-2H-pyran-3,4,5-triyl triacetate (170 mg) as a white solid.

¹H-NMR (CDCl₃) δ: 7.71-7.33 (m, 10H), 5.26-4.96 (m, 3H), 4.63 (d, 1H, J=7.9 Hz), 4.30-4.21 (m, 1H), 4.14-4.07 (m, 1H), 3.94-3.61 (m, 5H), 2.13-1.93 (m, 12H), 1.03 (s, 9H).

Second Step

A 1 mol/L tetrabutylammonium fluoride/tetrahydrofuran solution (540 μL) was added to a mixture of (2R,3R,4S,5R,6R)-2-(acetoxymethyl)-6-(2-((tert-butyldiphenylsilyl)oxy)ethoxy)tetrahydro-2H-pyran-3,4,5-triyl triacetate (170 mg), acetic acid (31 μL) and tetrahydrofuran (2.7 mL) which was then stirred at room temperature for 30 minutes. The solvent was distilled off under reduced pressure and the resulting residue was purified by silica gel column chromatography (hexane:ethyl acetate=50:50 to 0:100) to give (2R,3R,4S,5R,6R)-2-(acetoxymethyl)-6-(2-hydroxyethoxy)tetrahydro-2H-pyran-3,4,5-triyl triacetate (79.0 mg) as a colorless oil.

¹H-NMR (CDCl₃) δ: 5.30-5.16 (m, 1H), 5.11-4.97 (m, 2H), 4.56 (d, 1H, J=7.9 Hz), 4.20 (d, 2H, J=4.0 Hz), 3.88-3.66 (m, 5H), 2.13-1.97 (m, 12H).

Reference Example 16-2

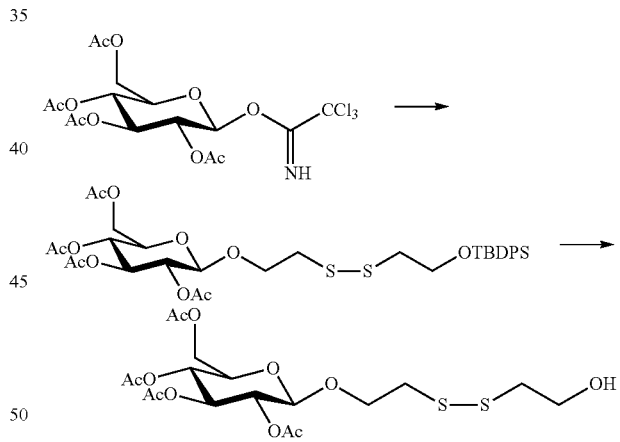

First Step

A boron trifluoride diethyl ether complex (54 μL) was added under ice-cooling to a mixture of (2R,3R,4S,5R,6S)-2-(acetoxymethyl)-6-(2,2,2-trichloro-1-iminoethoxy)tetrahydro-2H-pyran-3,4,5-triyl triacetate (525 mg), 2-((2-((tert-butyldiphenylsilyl)oxy)ethyl)disulfanyl)ethanol (417 mg), a molecular sieve 4 A and methylene chloride (5.3 mL) which was then stirred at room temperature for 10 minutes. Water was added to the reaction liquid which was then extracted with methylene chloride, the organic layer was dried over anhydrous magnesium sulfate, and then the solvent was distilled off under reduced pressure. The resulting residue was purified by silica gel column chromatography (hexane:ethyl acetate=80:20 to 50:50) to give (2R,3R,4S,5R,6R)-2-(acetoxymethyl)-6-(2-((2-((tert-butyldiphenylsilyl)oxy)

ethyl)disulfanyl)ethoxy)tetrahydro-2H-pyran-3,4,5-triyl triacetate (75.0 mg) as a colorless oil.

$^1$H-NMR (CDCl$_3$) δ: 7.70-7.34 (m, 10H), 5.24-4.94 (m, 3H), 4.51 (d, 1H, J=8.9 Hz), 4.31-3.99 (m, 3H), 3.92-3.64 (m, 4H), 2.86-2.71 (m, 4H), 2.15-1.98 (m, 12H), 1.06 (s, 9H).

Second Step

A 1 mol/L tetrabutylammonium fluoride/tetrahydrofuran solution (540 μL) was added to a mixture of (2R,3R,4S,5R,6R)-2-(acetoxymethyl)-6-(2-((2-((tert-butyldiphenylsilyl)oxy)ethyl)disulfanyl)ethoxy)tetrahydro-2H-pyran-3,4,5-triyl triacetate (75.0 mg), acetic acid (12 μL) and tetrahydrofuran (1.0 mL) which was then stirred at room temperature for 30 minutes. The solvent was distilled off under reduced pressure and the resulting residue was purified by silica gel column chromatography (hexane:ethyl acetate=50:50 to 0:100) to give (2R,3R,4S,5R,6R)-2-(acetoxymethyl)-6-(2-((2-hydroxyethyl)disulfanyl)ethoxy)tetrahydro-2H-pyran-3,4,5-triyl triacetate (33.0 mg) as a colorless oil.

$^1$H-NMR (CDCl$_3$) δ: 5.26-5.17 (m, 1H), 5.14-5.05 (m, 1H), 5.04-4.96 (m, 1H), 4.57-4.54 (m, 1H), 4.32-2.82 (m, 11H), 2.06-2.02 (m, 12H).

Example 1-1

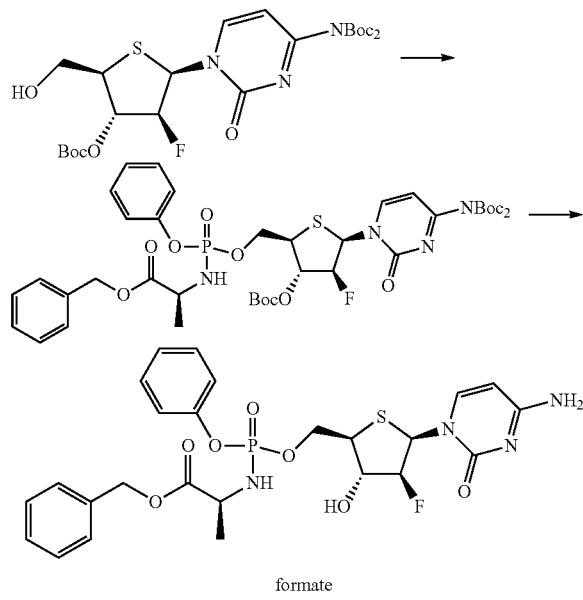

formate

First Step (1) Triethylamine (1.1 mL) was added at −78° C. to a mixture of phenyl dichlorophosphate (600 μL), L-alanine benzyl ester hydrochloride (864 mg) and methylene chloride (20 mL) which was then stirred at room temperature for 2 hours and 11 minutes. The solvent was distilled off under reduced pressure. Diethyl ether was added to the resulting residue, and the insoluble matter was separated by filtration. The solvent was distilled off under reduced pressure to give (2S)-benzyl 2-(((RS)-chloro(phenoxy)phosphoryl)amino)propanoate as a crude product.

(2) Under a nitrogen atmosphere, a 1.0 mol/L tert-butyl magnesium chloride/tetrahydrofuran solution (710 μL) was added dropwise at −78° C. to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (80.0 mg) and tetrahydrofuran (2.0 mL) which was then stirred at room temperature for 10 minutes. A mixture of (2S)-benzyl 2-(((RS)-chloro(phenoxy)phosphoryl)amino)propanoate (150 mg) obtained in (1) and tetrahydrofuran (900 μL) was added to the reaction liquid which was then stirred at room temperature for 40 minutes. An aqueous saturated ammonium chloride solution was added to the reaction liquid which was then extracted with ethyl acetate and dried over anhydrous magnesium sulfate. The solvent was distilled off under reduced pressure to give (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)propanoate.

MS (ESI m/z): 879 (M+H)

RT (min): 2.06

Second Step

Trifluoroacetic acid (1.4 mL) was added under ice-cooling to a mixture of (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)propanoate and methylene chloride (1.4 mL) which was then stirred at room temperature for 30 minutes. The solvent was distilled off under reduced pressure and the resulting residue was purified by silica gel column chromatography (ethyl acetate:methanol=100:0 to 85:15) to give a colorless oil. The resulting colorless oil was purified by reverse phase preparative HPLC (0.1% aqueous formic acid solution-0.1% formic acid acetonitrile solution) to give a formate (3.6 mg) of (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate as a colorless oil.

$^1$H-NMR (CD$_3$OD) δ: 8.14 (s, 1H), 8.16-7.99 (m, 1H), 7.42-7.13 (m, 10H), 6.69-6.58 (m, 1H), 5.92-5.85 (m, 1H), 5.15 (s, 2H), 5.09-4.86 (m, 1H), 4.45-4.17 (m, 3H), 4.09-3.94 (m, 1H), 3.61-3.48 (m, 1H), 1.41-1.30 (m, 3H).

MS (ESI m/z): 579 (M+H)

RT (min): 1.13

Example 1-2

Compounds of Table 1 and Table 2 were obtained in the same manner as in Example 1-1.

TABLE 1

| R | Compound name | MS (ESI m/z) (M + H) | RT (min) |
|---|---|---|---|
| (phenyl phosphoramidate with methyl 2-methylpropanoate) | Methyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)-2-methylpropanoate | 817 | 1.96 |
| (phenyl phosphoramidate with isopropyl propanoate) | (2S)-isopropyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)propanoate | 831 | 2.03 |
| (phenyl phosphoramidate with ethyl 3-methylbutanoate) | (2S)-ethyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)-3-methylbutanoate | 845 | 2.07 |
| (phenyl phosphoramidate with ethyl propanoate) | (2S)-ethyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)propanoate | 817 | 1.96 |
| (4-chlorophenyl phosphoramidate with methyl propanoate) | (2S)-methyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(4-chlorophenoxy)phosphoryl)amino)propanoate | 837 | 1.99 |

TABLE 1-continued

| R | Compound name | MS (ESI m/z) (M + H) | RT (min) |
|---|---|---|---|
| (naphthalen-1-yloxy phosphoryl group with ethyl alaninate) | (2S)-ethyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(naphthalen-1-yloxy)phosphoryl)amino)propanoate | 867 | 2.06 |
| (naphthalen-1-yloxy phosphoryl group with benzyl alaninate) | (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(naphthalen-1-yloxy)phosphoryl)amino)propanoate | 929 | 2.14 |

TABLE 2 formate

| Example No. | R | Compound name | $^1$H-NMR | MS (ESI m/z) (M + H) | RT (min) |
|---|---|---|---|---|---|
| 1-2-1 | (phenoxy phosphoryl group with methyl 2-methylalaninate) | Methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)-2-methylpropanoate | $^1$H-NMR (CD$_3$OD) δ: 8.20 (s, 1H), 8.13-8.03 (m, 1H), 7.42-7.13 (m, 6H), 6.72-6.59 (m, 1H), 5.93-5.85 (m, 1H), 5.10-4.88 (m, 1H), 4.49-4.26 (m, 3H), 3.70 (s, 3H), 3.66-3.56 (m, 1H), 1.54-1.43 (m, 6H). | 517 | 0.89 |

TABLE 2-continued

[Structure: tetrahydrothiophene ring with R-O-CH2- group, HO, F substituents, and 4-amino-2-oxopyrimidin-1(2H)-yl (cytosine) group, formate salt]

| Example No. | R | Compound name | $^1$H-NMR | MS (ESI m/z) (M + H) | RT (min) |
|---|---|---|---|---|---|
| 1-2-2 | [phenoxy phosphoramidate with isopropyl alaninate] | (2S)-isopropyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate | $^1$H-NMR (CD$_3$OD) δ: 8.14-8.01 (m, 1H), 7.43-7.30 (m, 2H), 7.30-7.13 (m, 3H), 6.74-6.57 (m, 1H), 5.92-5.84 (m, 1H), 5.11-4.88 (m, 2H), 4.49-3.51 (m, 5H), 1.38-1.29 (m, 3H), 1.27-1.19 (m, 6H). | 531 | 1.02 |
| 1-2-3 | [phenoxy phosphoramidate with ethyl valinate] | (2S)-ethyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)-3-methylbutanoate | $^1$H-NMR (CD$_3$OD) δ: 8.13-8.02 (m, 1H), 7.41-7.14 (m, 5H), 6.73-6.61 (m, 1H), 5.92-5.87 (m, 1H), 5.09-4.88 (m, 1H), 4.47-3.52 (m, 7H), 2.13-1.96 (m, 1H), 1.34-1.19 (m, 3H), 1.02-0.83 (m, 6H). | 545 | 1.07 |
| 1-2-4 | [phenoxy phosphoramidate with ethyl alaninate] | (2S)-ethyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate | $^1$H-NMR (CD$_3$OD) δ: 8.25-8.20 (m, 1H), 8.14-8.03 (m, 1H), 7.42-7.31 (m, 2H), 7.29-7.16 (m, 3H), 6.73-6.58 (m, 1H), 5.94-5.86 (m, 1H), 5.11-4.88 (m, 1H), 4.52-3.52 (m, 7H), 1.40-1.29 (m, 3H), 1.28-1.20 (m, 3H). | 517 | 0.92 |
| 1-2-5 | [4-chlorophenoxy phosphoramidate with methyl alaninate] | (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-chlorophenoxy)phosphoryl)amino)propanoate | $^1$H-NMR (CD$_3$OD) δ: 8.16-8.04 (m, 2H), 7.42-7.33 (m, 2H), 7.29-7.17 (m, 2H), 6.75-6.57 (m, 1H), 5.94-5.88 (m, 1H), 5.12-4.89 (m, 1H), 4.49-4.24 (m, 3H), 4.04-3.90 (m, 1H), 3.69 (s, 3H), 3.56-3.55 (m, 1H), 1.41-1.30 (m, 3H). | 537 | 0.96 |
| 1-2-6 | [naphthalen-1-yloxy phosphoramidate with ethyl alaninate] | (2S)-ethyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(naphthalen-1-yloxy)phosphoryl)amino)propanoate | $^1$H-NMR (CD$_3$OD) δ: 8.27-7.30 (m, 9H), 6.71-6.67 (m, 1H), 5.89-5.81 (m, 1H), 5.11-4.86 (m, 1H), 4.50-4.27 (m, 3H), 4.16-3.93 (m, 3H), 3.67-3.54 (m, 1H), 1.32 (t, 3H, J = 6.3 Hz), 1.24-1.11 (m, 3H). | 567 | 1.09 |

TABLE 2-continued

[Structure: formate with R-O-CH2- attached to tetrahydrothiophene ring bearing cytosine, with HO and F substituents]

formate

| Example No. | R | Compound name | $^1$H-NMR | MS (ESI m/z) (M + H) | RT (min) |
|---|---|---|---|---|---|
| 1-2-7 | [naphthalen-1-yloxy phosphoryl with L-alanine benzyl ester] | (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(naphthalen-1-yloxy)phosphoryl)amino) propanoate | $^1$H-NMR (CD$_3$OD) δ: 8.18-7.38 (m, 9H), 7.35-7.19 (m, 5H), 6.72-6.59 (m, 1H), 5.91-5.75 (m, 1H), 5.16-4.84 (m, 3H), 4.47-4.25 (m, 3H), 4.11-4.06 (m, 1H), 3.63-3.50 (m, 1H), 1.39-1.27 (m, 3H) | 629 | 1.25 |

Example 2-1

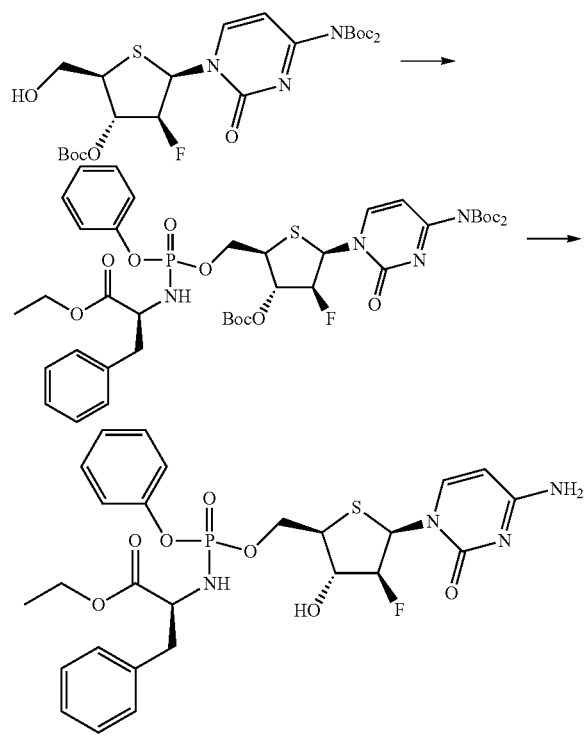

First Step (1) Triethylamine (553 μL) was added at −78° C. to a mixture of phenyl dichlorophosphate (300 μL), L-phenylalanine benzyl ester hydrochloride (460 mg) and methylene chloride (10 mL) which was then stirred for 15 minutes, followed by stirring at room temperature for 1 hour. The solvent was distilled off under reduced pressure. Diethyl ether was added to the resulting residue, and the insoluble matter was separated by filtration. The solvent was distilled off under reduced pressure to give (2S)-ethyl 2-(((RS)-chloro(phenoxy)phosphoryl)amino)-3-phenylpropanoate.

(2) Under a nitrogen atmosphere, a 1.0 mol/L tert-butyl magnesium chloride/tetrahydrofuran (710 μL) solution was added dropwise at −78° C. to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (80.0 mg) and tetrahydrofuran (2.0 mL) which was then stirred at room temperature for 10 minutes. A mixture of (2S)-ethyl 2-(((RS)-chloro(phenoxy)phosphoryl)amino)-3-phenylpropanoate (150 mg) obtained in (1) and tetrahydrofuran (900 μL) was added to the reaction liquid which was then stirred at room temperature for 4 hours and 45 minutes. An aqueous saturated ammonium chloride solution was added to the reaction liquid which was then extracted with ethyl acetate and dried over anhydrous magnesium sulfate. The solvent was distilled off under reduced pressure to give (2S)-ethyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)-3-phenylpropanoate.

MS (ESI m/z): 893 (M+H)
RT (min): 2.09

Second Step

Trifluoroacetic acid (1.4 mL) was added under ice-cooling to a mixture of (2S)-ethyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)-3-phenylpropanoate and methylene chloride (1.4 mL) which was then stirred at room temperature for 30 minutes. The solvent was distilled off under reduced pressure and the resulting residue was purified by reverse phase preparative HPLC (0.1% aqueous formic acid solution-0.1% formic acid acetonitrile solution) to give a colorless oil. The resulting colorless oil was purified by silica gel column chromatography (ethyl acetate:methanol=100:0 to 85:15) to give (2S)-ethyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)-3-phenylpropanoate (2.3 mg) as a colorless oil.

$^1$H-NMR (CD$_3$OD) δ: 8.05-7.97 (m, 1H), 7.36-7.05 (m, 10H), 6.70-6.58 (m, 1H), 5.91-5.83 (m, 1H), 5.07-4.86 (m, 1H), 4.39-3.40 (m, 7H), 3.15-3.01 (m, 1H), 2.93-2.80 (m, 1H), 1.22-1.13 (m, 3H).

MS (ESI m/z): 593 (M+H)

RT (min): 1.14

Example 2-2

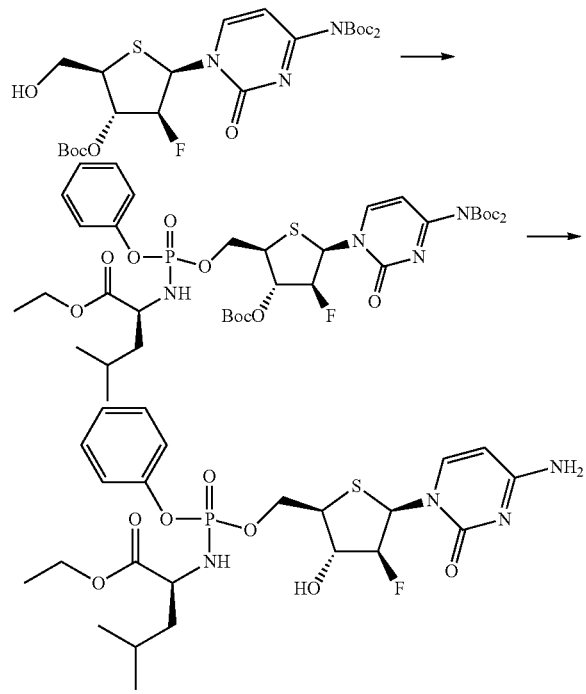

First Step

The following compound was obtained in the same manner as in the first step of Example 2-1.

(2S)-ethyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)-4-methylpentanoate MS (ESI m/z): 859 (M+H)

RT (min): 2.12

Second Step

The following compound was obtained in the same manner as in the second step of Example 2-1.

(2S)-ethyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)-4-methylpentanoate $^1$H-NMR (CD$_3$OD) δ: 8.18-8.01 (m, 1H), 7.41-7.14 (m, 5H), 6.74-6.59 (m, 1H), 5.93-5.86 (m, 1H), 5.10-4.88 (m, 1H), 4.50-3.52 (m, 7H), 1.81-1.68 (m, 1H), 1.59-1.45 (m, 2H), 1.27-1.19 (m, 3H), 0.96-0.77 (m, 6H).

MS (ESI m/z): 559 (M+H)

RT (min): 1.15

Example 3-1

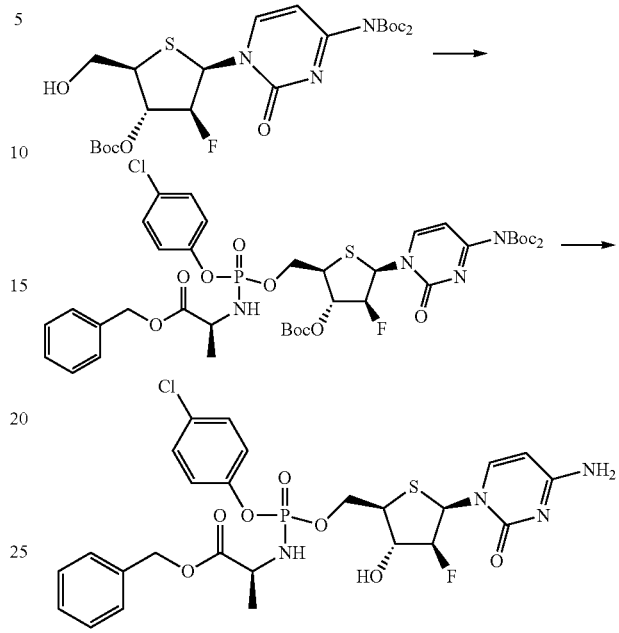

First Step (1) Triethylamine (827 μL) was added at −78° C. to a mixture of L-alanine benzyl ester hydrochloride (646 mg), (4-chlorophenyl)phosphoryl dichloride (500 μL) and methylene chloride (1.5 mL) which was then stirred for 5 minutes, followed by stirring at room temperature for 70 minutes. Hexane was added to the reaction liquid, and the insoluble matter was separated by filtration. The solvent was distilled off under reduced pressure to give (2S)-benzyl 2-(((RS)-chloro(4-chlorophenoxy)phosphoryl)amino)propanoate.

(2) Under a nitrogen atmosphere, a 1.0 mol/L tert-butyl magnesium chloride/tetrahydrofuran solution (2.0 mL) was added dropwise at −78° C. to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (448 mg) and tetrahydrofuran (10.6 mL) which was then stirred for 5 minutes. A mixture of (2S)-benzyl 2-(((RS)-chloro(4-chlorophenoxy)phosphoryl)amino)propanoate obtained in (1) and tetrahydrofuran (5.3 mL) was added at −78° C. to the reaction liquid which was then stirred at room temperature for 30 minutes. An aqueous saturated ammonium chloride solution was added to the reaction liquid which was then extracted with ethyl acetate and dried over anhydrous magnesium sulfate. The solvent was distilled off under reduced pressure and the resulting residue was purified by silica gel column chromatography (hexane:ethyl acetate=80:20 to 0:100) to give (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(4-chlorophenoxy)phosphoryl)amino)propanoate (539 mg) as a yellow solid.

MS (ESI m/z): 913 (M+H)

RT (min): 2.13

Second Step

Trifluoroacetic acid (1.5 mL) was added to a mixture of (2S)-benzyl 2-(((RS)-((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(4-chlorophenoxy)phosphoryl)amino)propanoate (514 mg) and methylene chloride (1.5 mL) which was then stirred at room temperature for 40 minutes. The solvent was distilled off under reduced pressure and the resulting residue was purified by basic silica gel column chromatography (ethyl acetate:methanol=100:0 to 50:50) to give (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-chlorophenoxy)phosphoryl)amino)propanoate (135 mg) as a white solid.

¹H-NMR (CD₃OD) δ: 8.08-8.00 (m, 1H), 7.38-7.13 (m, 9H), 6.71-6.59 (m, 1H), 5.91-5.83 (m, 1H), 5.16-4.84 (m, 3H), 4.45-4.16 (m, 3H), 4.09-3.93 (m, 1H), 3.62-3.47 (m, 1H), 1.40-1.34 (m, 3H).

MS (ESI m/z): 613 (M+H)

RT (min): 1.23

Example 3-2

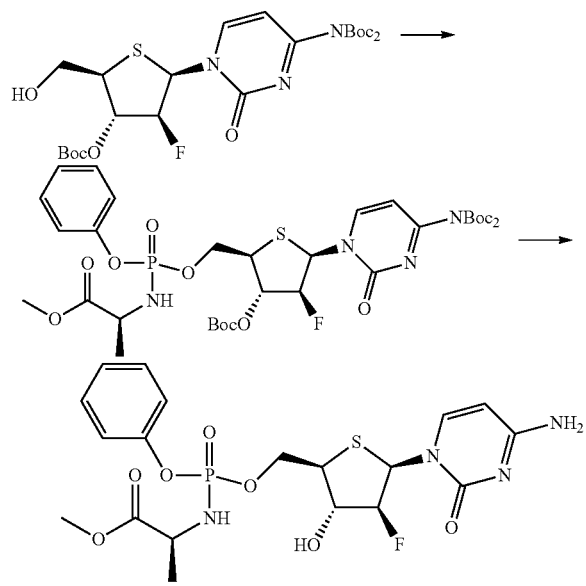

First Step

The following compound was obtained in the same manner as in the first step of Example 3-1.

(2S)-methyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)propanoate MS (ESI m/z): 803 (M+H)

RT (min): 1.89

Second Step

The following compound was obtained in the same manner as in the second step of Example 3-1.

(2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate ¹H-NMR (CD₃OD) δ: 8.15-8.05 (m, 1H), 7.42-7.16 (m, 5H), 6.73-6.61 (m, 1H), 5.95-5.87 (m, 1H), 5.12-4.83 (m, 1H), 4.50-4.23 (m, 3H), 4.05-3.91 (m, 1H), 3.72-3.53 (m, 4H), 1.40-1.29 (m, 3H).

MS (ESI m/z): 503 (M+H)

RT (min): 0.87

Example 4-1

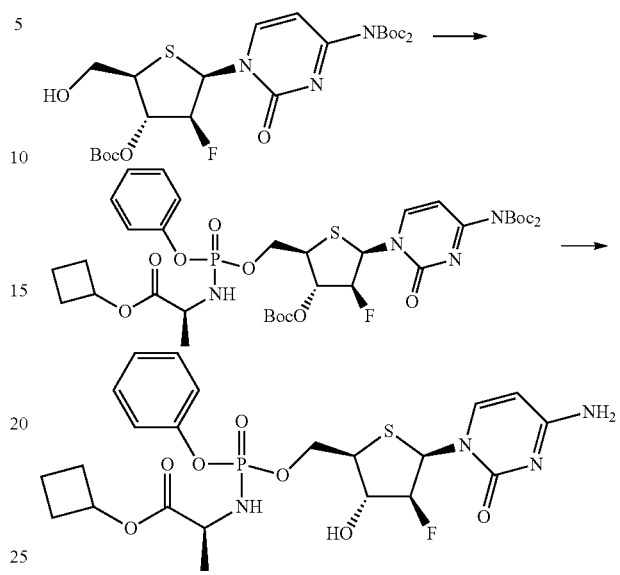

First Step (1) Phenyl dichlorophosphate (153 μL) and triethylamine (143 μL) were added at −78° C. to a mixture of L-alanine cyclobutyl ester (148 mg) and methylene chloride (1.5 mL) which was then stirred at room temperature for 1 hour. The solvent was distilled off under reduced pressure. Diethyl ether was added to the resulting residue and the insoluble matter was separated by filtration. The solvent was distilled off under reduced pressure to give (2S)-cyclobutyl 2-(((RS)-chloro(phenoxy)phosphoryl)amino)propanoate.

(2) Under a nitrogen atmosphere, a 1.0 mol/L tert-butyl magnesium chloride/tetrahydrofuran solution (500 μL) was added dropwise at −78° C. to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (100 mg) and tetrahydrofuran (2.0 mL) which was then stirred for 30 minutes. A mixture of (2S)-cyclobutyl 2-(((RS)-chloro(phenoxy)phosphoryl)amino)propanoate obtained in (1) and tetrahydrofuran (2.0 mL) was added at −78° C. to the reaction liquid which was then stirred at room temperature for 16 hours. Water was added to the reaction liquid which was then extracted with ethyl acetate and dried over anhydrous sodium sulfate. The solvent was distilled off under reduced pressure and the resulting residue was purified by silica gel column chromatography (hexane:ethyl acetate=100:0 to 70:30) to give (2S)-cyclobutyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)propanoate (33.7 mg) as a colorless oil.

MS (ESI m/z): 843 (M+H)

RT (min): 1.76

Second Step

Trifluoroacetic acid (1.0 mL) was added to a mixture of (2S)-cyclobutyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)propanoate (33.7 mg) and methylene chloride (1.0 mL) which was then stirred at room temperature for 2.5 hours. The solvent was distilled off under reduced pressure. Methylene chloride (2.0 mL) and triethylamine (1.0 mL) were added to the resulting residue, and the solvent was distilled off under reduced pressure. The resulting residue was purified by basic silica gel column chromatography (ethyl acetate:methanol=100:0 to 80:20) to give (2S)-cyclobutyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate (11.3 mg) as a white solid.

$^1$H-NMR (CD$_3$OD) δ: 8.13-8.00 (m, 1H), 7.42-7.32 (m, 2H), 7.29-7.15 (m, 3H), 6.72-6.60 (m, 1H), 5.93-5.84 (m, 1H), 5.11-4.89 (m, 2H), 4.49-4.21 (m, 3H), 3.99-3.86 (m, 1H), 3.66-3.51 (m, 1H), 2.39-2.24 (m, 2H), 2.15-1.97 (m, 2H), 1.86-1.71 (m, 1H), 1.70-1.58 (m, 1H), 1.39-1.27 (m, 3H).

MS (ESI m/z): 543 (M+H)
RT (min): 1.09

Example 4-2

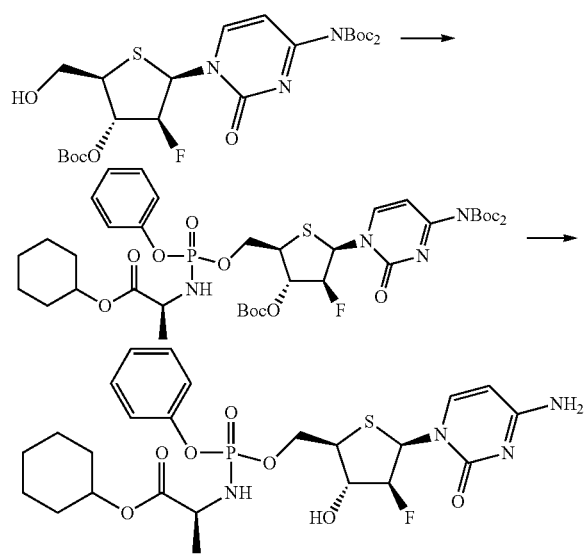

First Step

The following compound was obtained in the same manner as in the first step of Example 4-1.

(2S)-cyclohexyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)propanoate MS (ESI m/z): 871 (M+H)
RT (min): 1.72

Second Step

The following compound was obtained in the same manner as in the second step of Example 4-1.

(2S)-cyclohexyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate $^1$H-NMR (CD$_3$OD) δ: 8.12-8.02 (m, 1H), 7.41-7.32 (m, 2H), 7.28-7.15 (m, 3H), 6.72-6.60 (m, 1H), 5.92-5.85 (m, 1H), 5.10-4.90 (m, 1H), 4.81-4.66 (m, 1H), 4.49-4.23 (m, 3H), 3.99-3.86 (m, 1H), 3.65-3.50 (m, 1H), 1.88-1.66 (m, 4H), 1.58-1.23 (m, 9H).

MS (ESI m/z): 571 (M+H)
RT (min): 1.27

Example 5-1

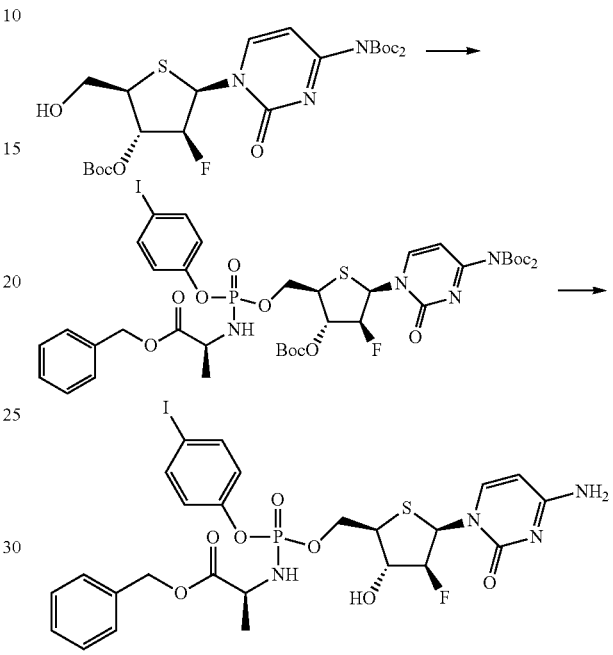

First Step (1) 4-iodophenol (330 mg) and triethylamine (207 μL) were added at −78° C. to a mixture of phosphorus oxychloride (139 μL) and methylene chloride (15 mL) which was then stirred for 5 minutes. The reaction liquid was stirred at room temperature for 10 minutes, and L-alanine benzyl ester hydrochloride (324 mg) and triethylamine (415 μL) were added thereto at −78° C., followed by stirring for 5 minutes. After stirring at room temperature for 30 minutes, hexane was added to the reaction liquid and the insoluble matter was separated by filtration. The solvent was distilled off under reduced pressure to give (2S)-benzyl 2-(((RS)-chloro(4-iodophenoxy)phosphoryl)amino)propanoate (2) Under a nitrogen atmosphere, a 1.0 mol/L tert-butyl magnesium chloride/tetrahydrofuran solution (833 μL) was added dropwise at −78° C. to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (185 mg) and tetrahydrofuran (4.5 mL) which was then stirred for 5 minutes. A mixture of (2S)-benzyl 2-(((RS)-chloro(4-iodophenoxy)phosphoryl)amino)propanoate obtained in (1) and tetrahydrofuran (2.2 mL) was added at −78° C. to the reaction liquid which was then stirred at room temperature for 30 minutes. An aqueous saturated ammonium chloride solution was added to the reaction liquid which was then extracted with ethyl acetate and dried over anhydrous magnesium sulfate. The solvent was distilled off under reduced pressure and the resulting residue was purified by silica gel column chromatography (hexane:ethyl acetate=80:20 to 0:100) to give (2S)-benzyl 2-(((RS)-(((2R,3S,4S,5R)-5-(4-(bis(tert-butoxycarbonyl)amino)-2-oxopyrimidin-1(2H)- yl)-3-((tert-butoxycarbonyl)oxy)-4-fluorotetrahydrothiophen-2-yl)methoxy)(4-iodophenoxy)phosphoryl)amino)propanoate (123 mg) as a colorless oil.

MS (ESI m/z): 1005 (M+H)
RT (min): 2.14

Second Step

Trifluoroacetic acid (1.0 mL) was added to a mixture of (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(4-iodophenoxy)phosphoryl)amino)propanoate (123 mg) and methylene chloride (1.0 mL) which was then stirred at room temperature for 30 minutes. The solvent was distilled off under reduced pressure and the resulting residue was purified by basic silica gel column chromatography (ethyl acetate:methanol=100:0 to 50:50) to give (2S)-benzyl 2-(((((2R,3S,4S,5R)-5-(4-amino-2-oxopyrimidin-1(2H)-yl)-4-fluoro-3-hydroxytetrahydrothiophen-2-yl)methoxy)(4-iodophenoxy)phosphoryl)amino)propanoate (68.0 mg) as a white solid.

$^1$H-NMR (CD$_3$OD) δ: 8.11-7.99 (m, 1H), 7.89-7.79 (m, 1H), 7.50-7.24 (m, 7H), 6.99-6.88 (m, 1H), 6.73-6.58 (m, 1H), 5.94-5.83 (m, 1H), 5.21-4.83 (m, 3H), 4.50-4.02 (m, 4H), 3.70-3.48 (m, 1H), 1.46-1.31 (m, 3H).

MS (ESI m/z): 705 (M+H)
RT (min): 1.26

Example 5-2

Compounds of Table 3, Table 4-1 and Table 4-2 were obtained in the same manner as in Example 5-1.

TABLE 3

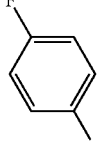

| R | Compound name | MS (ESI m/z) (M + H) | RT (min) |
|---|---|---|---|
| 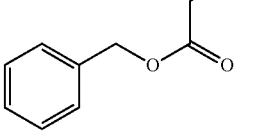 | (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(4-fluorophenoxy)phosphoryl)amino)propanoate | 897 | 2.06 |
| | (2S)-methyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(4-fluorophenoxy)phosphoryl)amino)propanoate | 821 | 1.91 |

TABLE 3-continued

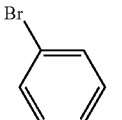

| R | Compound name | MS (ESI m/z) (M + H) | RT (min) |
|---|---|---|---|
| 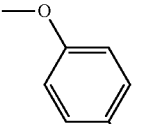 | (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy) (4-bromophenoxy)phosphoryl)amino) propanoate | 959 | 2.27 |
| 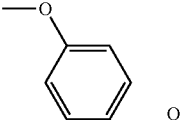 | (2S)-benzyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetra-hydrothiophen-2-yl)methoxy)(4-methoxy-phenoxy)phosphoryl)amino)propanoate | 909 | 2.04 |
| 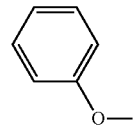 | (2S)-methyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetra-hydrothiophen-2-yl)methoxy)(4-methoxy-phenoxy)phosphoryl)amino)propanoate | 833 | 1.88 |
| | (2S)-benzyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetra-hydrothiophen-2-yl)methoxy)(phenoxy) phosphoryl)amino)-4-methylpentanoate | 921 | 2.19 |

TABLE 3-continued

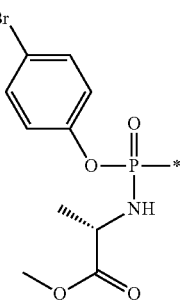 [SMILES: *P(=O)(N[C@@H](C)C(=O)OC)Oc1ccc(F)cc1]

| R | Compound name | MS (ESI m/z) (M + H) | RT (min) |
|---|---|---|---|
| 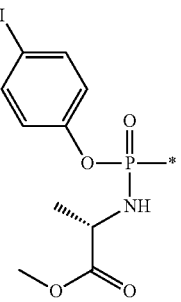 [SMILES: *P(=O)(N[C@@H](C)C(=O)OC)Oc1ccc(I)cc1] | (2S)-methyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetrahydro-thiophen-2-yl)methoxy)(4-bromo-phenoxy)phosphoryl)amino)propanoate | 883 | 2.00 |
| 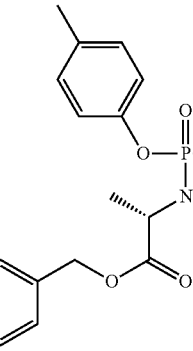 | (2S)-methyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetrahydro-thiophen-2-yl)methoxy)(4-iodo-phenoxy)phosphoryl)amino)propanoate | 929 | 1.99 |
| 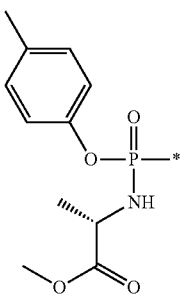 [SMILES: *P(=O)(N[C@@H](C)C(=O)OC)Oc1ccc(C)cc1] | (2S)-benzyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetrahydro-thiophen-2-yl)methoxy)(p-tolyloxy)phosphoryl)amino)propanoate | 893 | 2.11 |
|  | (2S)-methyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetrahydro-thiophen-2-yl)methoxy)(p-tolyloxy)phosphoryl)amino)propanoate | 817 | 1.95 |

TABLE 3-continued

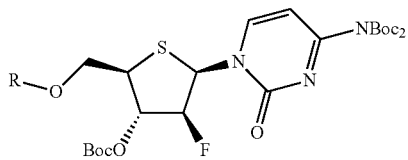

| R | Compound name | MS (ESI m/z) (M + H) | RT (min) |
|---|---|---|---|
| [phenyl phosphoramidate with leucine methyl ester] | (2S)-methyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)-4-methylpentanoate | 845 | 2.06 |
| [phenyl phosphoramidate with valine benzyl ester] | (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)-3-methylbutanoate | 907 | 2.15 |
| [phenyl phosphoramidate with valine methyl ester] | (2S)-methyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)amino)-3-methylbutanoate | 831 | 2.00 |

TABLE 4-1

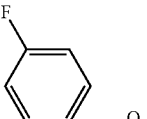

| Example No. | R | Compound name | ¹H-NMR | MS (ESI m/z) (M + H) | RT (min) |
|---|---|---|---|---|---|
| 5-2-1 | 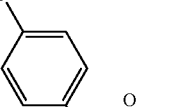 | (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-fluorophenoxy)phosphoryl)amino)propanoate | ¹H-NMR (CD$_3$OD) δ: 8.09-8.00 (m, 1H), 7.37-7.01 (m, 9H), 6.71-6.58 (m, 1H), 5.92-5.84 (m, 1H), 5.18-4.88 (m, 3H), 4.45-4.17 (m, 3H), 4.07-3.92 (m, 1H), 3.60-3.50 (m, 1H), 1.41-1.30 (m, 3H). | 597 | 1.16 |
| 5-2-2 | 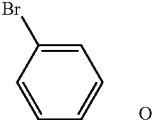 | (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-fluorophenoxy)phosphoryl)amino)propanoate | ¹H-NMR (CD$_3$OD) δ: 8.14-8.02 (m, 1H), 7.30-7.03 (m, 4H), 6.72-6.58 (m, 1H), 5.94-5.85 (m, 1H), 5.12-4.89 (m, 1H), 4.50-4.20 (m, 3H), 4.04-3.91 (m, 1H), 3.73-3.53 (m, 4H), 1.40-1.29 (m, 3H). | 521 | 0.88 |
| 5-2-3 |  | (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-bromophenoxy)phosphoryl)amino)propanoate | ¹H-NMR (CD$_3$OD) δ: 8.09-7.98 (m, 1H), 7.62-7.07 (m, 9H), 6.72-6.59 (m, 1H), 5.94-5.84 (m, 1H), 5.18-4.84 (m, 3H), 4.48-4.18 (m, 3H), 4.09-3.95 (m, 1H), 3.63-3.51 (m, 1H), 1.41-1.31 (m, 3H). | 659 | 1.23 |
| 5-2-4 | | (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-bromophenoxy)phosphoryl)amino)propanoate | ¹H-NMR (CD$_3$OD) δ: 8.12-8.04 (m, 1H), 7.56-7.49 (m, 2H), 7.22-7.14 (m, 2H), 6.73-6.61 (m, 1H), 5.94-5.87 (m, 1H), 6.11-4.89 (m, 1H), 4.50-4.22 (m, 3H), 4.14-3.90 (m, 1H), 3.71-3.52 (m, 4H), 1.39-1.31 (m, 3H). | 583 | 0.99 |

TABLE 4-1-continued

| Example No. | R | Compound name | ¹H-NMR | MS (ESI m/z) (M + H) | RT (min) |
|---|---|---|---|---|---|
| 5-2-5 | (4-iodophenyl phosphoramidate alaninate methyl ester) | (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-iodophenoxy)phosphoryl)amino)propanoate | ¹H-NMR (CD₃OD) δ: 8.16-8.04 (m, 1H), 7.91-7.81 (m, 1H), 7.68-7.11 (m, 2H), 7.00-6.91 (m, 1H), 6.72-6.59 (m, 1H), 6.10-5.90 (m, 1H), 5.12-4.89 (m, 1H), 4.64-4.29 (m, 3H), 4.18-3.98 (m, 1H), 3.73-3.56 (m, 4H), 1.44-1.31 (m, 3H). | 629 | 0.98 |
| 5-2-6 | (p-tolyl phosphoramidate alaninate benzyl ester) | (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(p-tolyloxy)phosphoryl)amino)propanoate | ¹H-NMR (CD₃OD)) δ: 8.31-8.19 (m, 1H), 7.42-7.03 (m, 9H), 6.63-6.51 (m, 1H), 6.04-5.96 (m, 1H), 5.17-4.89 (m, 3H), 4.45-3.93 (m, 4H), 3.61-3.50 (m, 1H), 2.30 (s, 3H), 1.55-1.29 (m, 3H). | 593 | 1.23 |

TABLE 4-2

| Example No. | R | Compound name | ¹H-NMR | MS (ESI m/z) (M + H) | RT (min) |
|---|---|---|---|---|---|
| 5-2-7 | (p-tolyl phosphoramidate alaninate methyl ester) | (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(p-tolyloxy)phosphoryl)amino)propanoate | ¹H-NMR (CD₃OD) δ: 8.14-8.04 (m, 1H), 7.21-7.06 (m, 4H), 6.72-6.60 (m, 1H), 5.92-5.86 (m, 1H), 5.11-4.89 (m, 1H), 4.49-4.22 (m, 3H), 4.02-3.90 (m, 1H), 3.69 (s, 3H), 3.66-3.51 (m, 1H), 2.31 (s, 3H), 1.39-1.28 (m, 3H). | 517 | 0.97 |

TABLE 4-2-continued

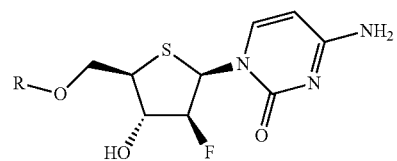

| Example No. | R | Compound name | $^1$H-NMR | MS (ESI m/z) (M + H) | RT (min) |
|---|---|---|---|---|---|
| 5-2-8 | (structure: 4-methoxyphenoxy-P(=O)(O-)-NH-CH(CH3)-C(=O)-O-benzyl) | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(4-methoxy-phenoxy)phosphoryl)amino) propanoate | $^1$H-NMR (CD$_3$OD) δ: 8.10-7.99 (m, 1H), 7.39-7.26 (m, 5H), 7.16-7.07 (m, 2H), 6.90-6.83 (m, 2H), 6.70-6.58 (m, 1H), 5.91-5.82 (m, 1H), 5.17-4.87 (m, 3H), 4.45-4.15 (m, 3H), 4.07-3.92 (m, 1H), 3.75 (s, 3H), 3.60-3.47 (m, 1H), 1.40-1.29 (m, 3H). | 609 | 1.18 |
| 5-2-9 | (structure: 4-methoxyphenoxy-P(=O)(O-)-NH-CH(CH3)-C(=O)-O-methyl) | (2S)-methyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(4-methoxy-phenoxy)phosphoryl)amino) propanoate | $^1$H-NMR (CD$_3$OD) δ: 8.16-8.04 (m, 1H), 7.21-7.08 (m, 2H), 6.94-6.84 (m, 2H), 6.72-6.59 (m, 1H), 5.93-5.86 (m, 1H), 5.11-4.89 (m, 1H), 4.50-4.19 (m, 3H), 4.03-3.87 (m, 1H), 3.77 (s, 3H), 3.71-3.67 (m, 3H), 3.65-3.52 (m, 1H), 1.39-1.29 (m, 3H). | 533 | 0.89 |
| 5-2-10 | (structure: phenoxy-P(=O)(O-)-NH-CH(iBu)-C(=O)-O-benzyl) | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(phenoxy) phosphoryl)amino)-4-methylpentanoate | $^1$H-NMR (CD$_3$OD) δ: 8.10-7.99 (m, 1H), 7.39-7.13 (m, 10H), 6.71-6.59 (m, 1H), 5.92-5.82 (m, 1H), 5.15-4.83 (m, 3H), 4.44-4.15 (m, 3H), 3.99-3.84 (m, 1H), 3.61-3.47 (m, 1H), 1.79-1.62 (m, 1H), 1.58-1.44 (m, 2H), 0.95-0.72 (m, 6H). | 621 | 1.33 |
| 5-2-11 | (structure: phenoxy-P(=O)(O-)-NH-CH(iBu)-C(=O)-O-methyl) | (2S)-methyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(phenoxy) phosphoryl)amino)-4-methylpentanoate | $^1$H-NMR (CD$_3$OD) δ: 8.15-8.02 (m, 1H), 7.42-7.14 (m, 6H), 6.73-6.59 (m, 1H), 5.94-5.85 (m, 1H), 5.08-4.86 (m, 1H), 4.49-4.21 (m, 3H), 3.95-3.83 (m, 1H), 3.70-3.51 (m, 4H), 1.80-1.44 (m, 3H), 1.02-0.75 (m, 6H). | 545 | 1.10 |

TABLE 4-2-continued

| Example No. | R | Compound name | ¹H-NMR | MS (ESI m/z) (M + H) | RT (min) |
|---|---|---|---|---|---|
| 5-2-12 | | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(phenoxy)phosphoryl)amino)-3-methylbutanoate | ¹H-NMR (CD₃OD) δ: 8.07-8.02 (m, 1H), 7.40-7.12 (m, 10H), 6.71-6.58 (m, 1H), 5.90-5.83 (m, 1H), 5.16-4.82 (m, 3H), 4.44-4.16 (m, 3H), 3.78-3.64 (m, 1H), 3.60-3.48 (m, 1H), 2.12-1.95 (m, 1H), 0.96-0.78 (m, 6H). | 607 | 1.28 |
| 5-2-13 | | (2S)-methyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(phenoxy)phosphoryl)amino)-3-methylbutanoate | ¹H-NMR (CD₃OD) δ: 8.11-8.03 (m, 1H), 7.41-7.15 (m, 5H), 6.73-6.60 (m, 1H), 5.93-5.83 (m, 1H), 5.09-4.82 (m, 1H), 4.48-4.21 (m, 2H), 4.37-4.01 (m, 3H), 3.75-3.51 (m, 3H), 2.11-1.94 (m, 1H), 1.00-0.82 (m, 6H). | 531 | 1.02 |

Example 6-1

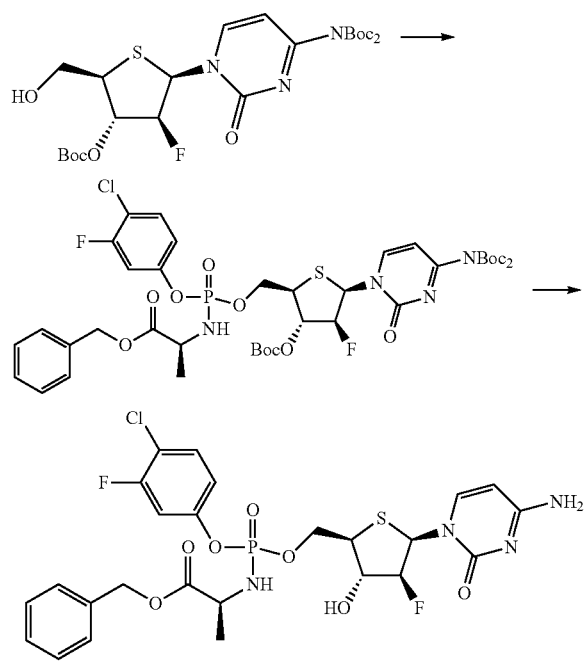

First Step (1) Under a nitrogen atmosphere, 4-chloro-3-fluorophenol (146 mg) and triethylamine (150 μL) were added at −78° C. to a mixture of phosphorus oxychloride (96 μL) and methylene chloride (2.0 mL) which was then stirred for 1 hour. L-alanine benzyl ester hydrochloride (226 mg) and triethylamine (300 μL) were added at −78° C. to the reaction liquid which was then stirred at room temperature for 1.5 hours. The solvent was distilled off under reduced pressure. Diethyl ether was added to the resulting residue and the insoluble matter was separated by filtration. The solvent was distilled off under reduced pressure to give (2S)-benzyl 2-(((RS)-chloro(4-chloro-3-fluorophenoxy)phosphoryl)amino)propanoate.

(2) Under a nitrogen atmosphere, a 1.0 mol/L tert-butyl magnesium chloride/tetrahydrofuran solution (500 μL) was added dropwise at −78° C. to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (100 mg) and tetrahydrofuran (2.0 mL) which was then stirred for 30 minutes. A mixture of (2S)-benzyl 2-(((RS)-chloro(4-chloro-3-fluorophenoxy)phosphoryl)amino)propanoate obtained in (1) and tetrahydrofuran (2.0 mL) was added at −78° C. to the reaction liquid which was then stirred at room temperature for 12 hours. Water was added to the reaction liquid which was then extracted with ethyl acetate, washed with an aqueous saturated sodium chloride solution and then dried over anhydrous sodium sulfate. The solvent was distilled off under reduced pressure and the resulting residue was purified by silica gel column chromatography (hexane:ethyl acetate=100:0 to 70:30) to give (2S)-benzyl 2-(((RS)-

(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(4-chloro-3-fluorophenoxy)phosphoryl)amino)propanoate (79.7 mg) as a colorless oil.

MS (ESI m/z): 931 (M+H)
RT (min): 2.14

Second Step

Trifluoroacetic acid (1.0 mL) was added to a mixture of (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(4-chloro-3-fluorophenoxy)phosphoryl)amino)propanoate (79.7 mg) and methylene chloride (1.0 mL) which was then stirred at room temperature for 2.5 hours. The solvent was distilled off under reduced pressure. Methylene chloride (2.0 mL) and triethylamine (1.0 mL) were added to the resulting residue, and the solvent was distilled off under reduced pressure. The resulting residue was purified by basic silica gel column chromatography (ethyl acetate:methanol=100:0 to 80:20) to give (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-chloro-3-fluorophenoxy)phosphoryl)amino)propanoate (23.2 mg) as a white solid.

$^1$H-NMR (CD$_3$OD) δ: 8.09-7.99 (m, 1H), 7.48-7.40 (m, 1¼H), 7.39-7.29 (m, 5H), 7.23-7.12 (m, 1H), 7.10-7.01 (m, 1H), 6.71-6.61 (m, 1H), 5.92-5.86 (m, 1H), 5.19-5.04 (m, 3H), 4.45-4.19 (m, 3H), 4.14-3.97 (m, 1H), 3.63-3.51 (m, 1H), 1.43-1.34 (m, 3H).

MS (ESI m/z): 631 (M+H)
RT (min): 1.32, 1.33

Example 6-2

Compounds of Table 5 and Table 6 were obtained in the same manner as in Example 6-1.

TABLE 5

| R | Compound name | MS (ESI m/z) (M + H) | RT (min) |
|---|---|---|---|
| 3,4-dichlorophenyl group | (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(3,4-dichlorophenoxy)phosphoryl)amino)propanoate | 947 | 2.20 |
| 2,4-difluorophenyl group | (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(2,4-difluorophenoxy)phosphoryl)amino)propanoate | 915 | 2.07 |

TABLE 5-continued

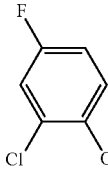

| R | Compound name | MS (ESI m/z) (M + H) | RT (min) |
|---|---|---|---|
| 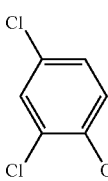 | (2S)-benzyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetrahydro-thiophen-2-yl)methoxy)(2-chloro-4-fluorophenoxy)phosphoryl)amino)propanoate | 931 | 2.12 |
|  | (2S)-benzyl 2-(((RS)-(((2R,3S,4S,5R)-5-(4-(bis(tert-butoxy-carbonyl)amino)-2-oxopyrimidin-1(2H)-yl)-3-((tert-butoxycarbonyl)oxy)-4-fluorotetrahydro-thiophen-2-yl)methoxy)(2,4-dichloro-phenoxy)phosphoryl)amino)propanoate | 947 | 2.20 |

TABLE 6

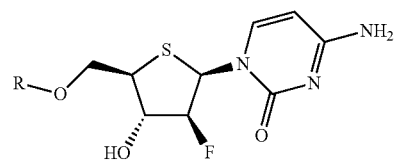

| Example No. | R | Compound name | ¹H-NMR | MS (ESI m/z) (M + H) | RT (min) |
|---|---|---|---|---|---|
| 6-2-1 | (3,4-dichlorophenoxy structure with phosphoryl benzyl alaninate) | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(3,4-dichlorophenoxy)phosphoryl)amino)propanoate | ¹H-NMR (CD₃OD) δ: 8.09-7.99 (m, 1H), 7.52-7.41 (m, 2H), 7.39-7.29 (m, 5H), 7.21-7.12 (m, 1H), 6.72-6.61 (m, 1H), 5.92-5.86 (m, 1H), 5.20-5.02 (m, 3H), 4.45-4.19 (m, 3H), 4.10-3.96 (m, 1H), 3.62-3.53 (m, 1H), 1.43-1.34 (m, 3H). | 647 | 1.38 1.39 |
| 6-2-2 | (2,4-difluorophenoxy structure with phosphoryl benzyl alaninate) | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(2,4-difluorophenoxy)phosphoryl)amino)propanoate | ¹H-NMR (CD₃OD) δ: 8.09-8.00 (m, 1H), 7.46-7.27 (m, 6H), 7.14-7.04 (m, 1H), 6.97-6.85 (m, 1H), 6.71-6.60 (m, 1H), 5.93-5.85 (m, 1H), 5.19-5.01 (m, 3H), 4.45-4.19 (m, 3H), 4.10-3.97 (m, 1H), 3.73-3.51 (m, 1H), 1.44-1.35 (m, 3H). | 615 | 1.23 1.25 |
| 6-2-3 | (2-chloro-4-fluorophenoxy structure with phosphoryl benzyl alaninate) | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(2-chloro-4-fluorophenoxy)phosphoryl)amino)propanoate | ¹H-NMR (CD₃OD) δ: 8.12-7.99 (m, 1H), 7.51-7.42 (m, 1H), 7.40-7.23 (m, 6H), 7.12-6.97 (m, 1H), 6.72-6.59 (m, 1H), 5.94-5.85 (m, 1H), 5.20-5.00 (m, 3H), 4.49-4.19 (m, 3H), 4.15-4.01 (m, 1H), 3.74-3.51 (m, 1H), 1.43-1.36 (m, 3H). | 631 | 1.28 1.31 |

TABLE 6-continued

[Structure: tetrahydrothiophene with cytosine, HO, F, and R-O-CH2- substituents]

| Example No. | R | Compound name | $^1$H-NMR | MS (ESI m/z) (M + H) | RT (min) |
|---|---|---|---|---|---|
| 6-2-4 | [2,4-dichlorophenoxy phosphoryl benzyl alaninate group] | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(2,4-dichlorophenoxy)phosphoryl)amino)propanoate | $^1$H-NMR (CD$_3$OD) δ: 8.06-7.98 (m, 1H), 7.55-7.42 (m, 2H), 7.39-7.24 (m, 6H), 6.72-6.50 (m, 1H), 5.91-5.85 (m, 1H), 5.19-5.00 (m, 3H), 4.46-4.18 (m, 3H), 4.14-4.03 (m, 1H), 3.73-3.53 (m, 1H), 1.43-1.37 (m, 9H). | 647 | 1.37 1.40 |

Example 6-3

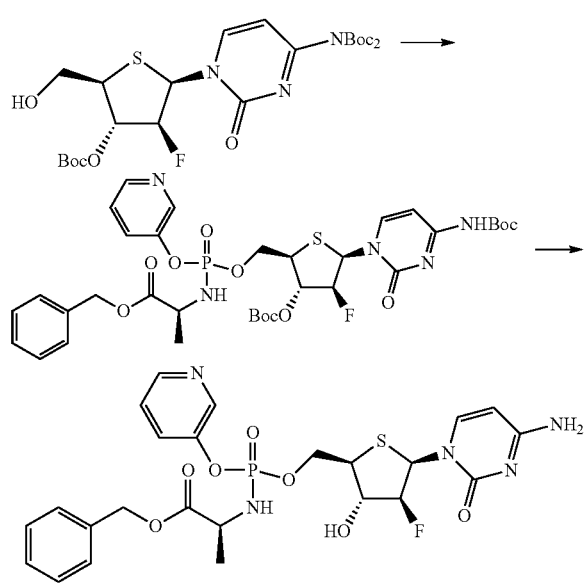

First Step

The following compound was obtained in the same manner as in the first step of Example 6-1.

(2S)-benzyl 2-(((RS)-(((2R,3S,4S,5R)-5-(4-(tert-butoxycarbonylamino)-2-oxopyrimidin-1(2H)-yl)-3-((tert-butoxycarbonyl)oxy)-4-fluorotetrahydrothiophen-2-yl)methoxy)(pyridin-3-yloxy)phosphoryl) amino)propanoate MS (ESI m/z): 780 (M+H)

RT (min): 1.59

Second Step

The following compound was obtained in the same manner as in the second step of Example 6-1.

(2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(pyridin-3-yloxy)phosphoryl)amino) propanoate MS (ESI m/z): 580 (M+H)

RT (min): 0.93

Example 7-1

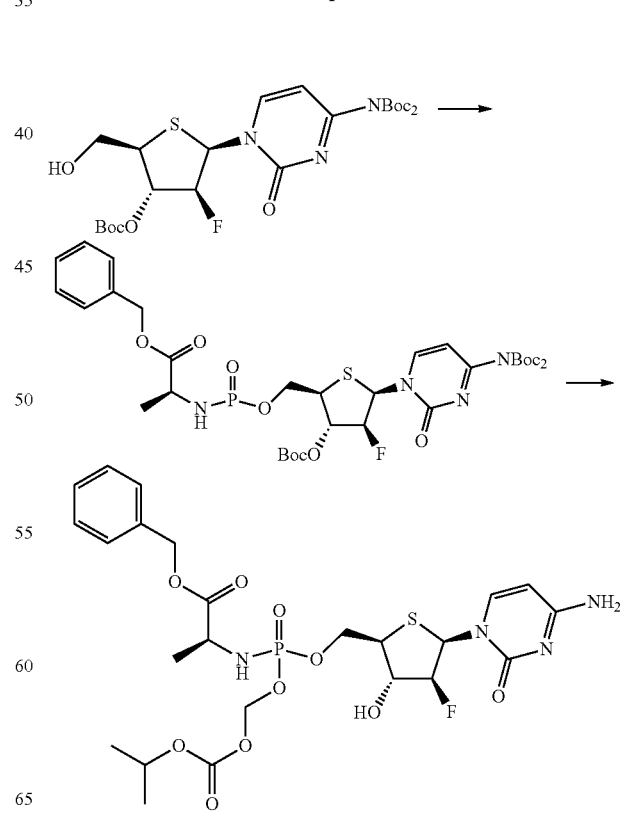

First Step

Under a nitrogen atmosphere, triethylamine (620 µL) was added at −78° C. to a mixture of phosphorus oxychloride (84 µL) and methylene chloride (2.2 mL), and then a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (500 mg) and methylene chloride (2.2 mL) was added thereto, followed by stirring for 1 hour. A mixture of L-alanine benzyl ester hydrochloride (192 mg) and methylene chloride (0.9 mL) was added to the reaction liquid which was then stirred at room temperature for 30 minutes. Water (0.5 mL) was added thereto, followed by stirring for 1.5 hours and extraction with ethyl acetate. The organic layer was washed with an aqueous saturated sodium chloride solution and dried over anhydrous sodium sulfate, and then the solvent was distilled off under reduced pressure. The resulting residue was purified by silica gel column chromatography (chloroform:methanol=95:5 to 70:30) to give (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(hydroxy)phosphoryl)amino)propanoate (308 mg) as a yellow solid.

MS (ESI m/z): 803 (M+H)

RT (min): 1.70

Second Step

Chloromethyl isopropyl carbonate (10 µL) was added to a mixture of (2S)-benzyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(hydroxy)phosphoryl)amino)propanoate (20.0 mg), N,N-diisopropylethylamine (17 µL) and N,N-dimethylformamide (1.0 mL) which was then stirred at 80° C. for 5 hours. Water was added at room temperature to the reaction liquid which was then extracted with isopropyl acetate. The organic layer was washed with water and an aqueous saturated sodium chloride solution and dried over anhydrous sodium sulfate, and then the solvent was distilled off under reduced pressure. Methylene chloride (0.5 mL) and trifluoroacetic acid (0.5 mL) were added to the resulting residue which was then stirred at room temperature for 1.5 hours. The solvent was distilled off under reduced pressure. Triethylamine (2.0 mL) was added to the resulting residue, and the solvent was distilled off under reduced pressure. The resulting residue was purified by silica gel column chromatography (chloroform:methanol=95:5 to 88:12) to give (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(((isopropoxycarbonyl)oxy)methoxy)phosphoryl)amino)propanoate (6.0 mg) as a white solid.

$^1$H-NMR (CD$_3$OD) δ: 8.11-8.02 (m, 1H), 7.41-7.27 (m, 5H), 6.72-6.58 (m, 1H), 5.92 (d, 1H, J=7.9 Hz), 5.64-5.51 (m, 2H), 5.18 (s, 2H), 5.10-4.88 (m, 1H), 4.47-4.36 (m, 1H), 4.34-4.11 (m, 2H), 4.05-3.89 (m, 1H), 3.70-3.42 (m, 2H), 1.41 (d, 3H, J=7.3 Hz), 1.28 (d, 6H, J=6.6 Hz).

MS (ESI m/z): 619 (M+H)

RT (min): 1.17

Example 7-2

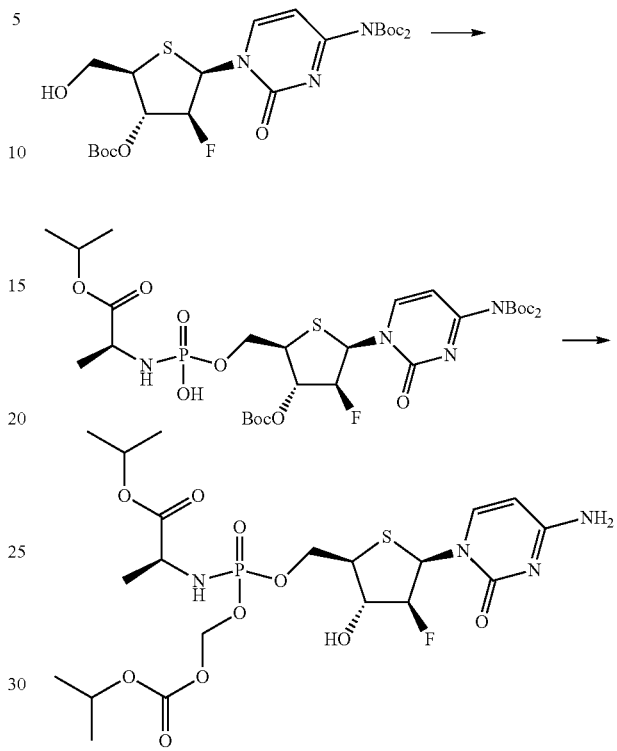

First Step

The following compound was obtained in the same manner as in the first step of Example 7-1.

(2S)-isopropyl 2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(hydroxy)phosphoryl)amino)propanoate MS (ESI m/z): 755 (M+H)

RT (min): 1.61

Second Step

The following compound was obtained in the same manner as in the second step of Example 7-1.

(2S)-isopropyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(((isopropoxycarbonyl)oxy)methoxy)phosphoryl)amino)propanoate $^1$H-NMR (CD$_3$OD) δ: 8.14-8.01 (m, 1H), 6.74-6.58 (m, 1H), 5.97-5.88 (m, 1H), 5.69-5.54 (m, 2H), 5.11-4.78 (m, 3H), 4.50-4.40 (m, 1H), 4.38-4.15 (m, 2H), 3.94-3.77 (m, 1H), 3.65-3.50 (m, 1H), 1.44-1.34 (m, 3H), 1.33-1.16 (m, 12H).

MS (ESI m/z): 571 (M+H)

RT (min): 1.05

Example 7-3

Compounds of Table 7 were obtained in the same manner as in the second step of Example 7-1.

TABLE 7

| Example No. | R | Compound name | $^1$H-NMR | MS (ESI m/z) (M + H) | RT (min) |
|---|---|---|---|---|---|
| 7-3-1 | | (((RS)-(((2R,3S,4S,5R)-5-(4-amino-2-oxopyrimidin-1(2H)-yl)-4-fluoro-3-hydroxytetrahydro-thiophen-2-yl)methoxy)(((S)-1-isopropoxy-1-oxopropan-2-yl)amino)phosphoryl)oxy) methyl pivalate | $^1$H-NMR (CD$_3$OD) δ: 8.12-8.03 (m, 1H), 6.74-6.60 (m, 1H), 5.97-5.88 (m, 1H), 5.70-5.55 (m, 2H), 5.10-4.85 (m, 2H), 4.50-4.39 (m, 1H), 4.38-4.13 (m, 2H), 3.93-3.78 (m, 1H), 3.66-3.49 (m, 1H), 1.39 (d, 3H, J = 7.3 Hz), 1.34-1.14 (m, 15H). | 569 | 1.10 |
| 7-3-2 | | (((RS)-(((2R,3S,4S,5R)-5-(4-amino-2-oxopyrimidin-1(2H)-yl)-4-fluoro-3-hydroxytetrahydro-thiophen-2-yl)methoxy)(((S)-1-(benzyloxy)-1-oxopropan-2-yl)amino)phosphoryl)oxy) methyl pivalate | $^1$H-NMR (CD$_3$OD) δ: 8.10-7.99 (m, 1H), 7.42-7.22 (m, 5H), 6.66 (dd, 1H, J = 18.8, 3.6 Hz), 5.92 (dd, 1H, J = 7.3, 2.0 Hz), 5.65-5.52 (m, 2H), 6.19 (s, 2H), 5.00-4.87 (m, 1H), 4.46-4.38 (m, 1H), 4.34-4.09 (m, 2H), 4.04-3.89 (m, 1H), 3.61-3.49 (m, 1H), 1.42 (d, 3H, J = 7.3 Hz), 1.22 (s, 3H). | 617 | 1.24 |
| 7-3-3 | | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(2-(pivaloylthio)ethoxy)phosphoryl) amino)propanoate | $^1$H-NMR (CD$_3$OD) δ: 8.11-8.02 (m, 1H), 7.41-7.27 (m, 5H), 6.71-6.08 (m, 1H), 5.92 (d, 1H, J = 7.3 Hz), 5.21-5.11 (m, 2H), 5.09-4.89 (m, 1H), 4.49-4.36 (m, 1H), 4.31-3.87 (m, 5H), 3.61-3.48 (m, 1H), 3.17-3.05 (m, 2H), 1.41 (d, 3H, J = 7.9 Hz), 1.25-1.19 (m, 9H). | 647 | 1.34 |
| 7-3-4 | | (2S)-benzyl 2-(((RS)-(((2R,3S,4S,5R)-5-(4-amino-2-oxopyrimidin-1(2H)-yl)-4-fluoro-3-hydroxytetrahydro-thiophen-2-yl)methoxy)(4-(pivaloylthio)butoxy)phosphoryl) amino)propanoate | $^1$H-NMR (CD$_3$OD) δ: 8.11-8.02 (m, 1H), 7.41-7.27 (m, 5H), 6.65 (dd, 1H, J = 18.5, 4.6 Hz), 5.91 (d, 1H, J = 7.3 Hz), 5.18 (s, 2H), 5.10-4.94 (m, 1H), 4.45-4.35 (m, 1H), 4.30-3.88 (m, 5H), 3.60-3.49 (m, 1H), 2.91-2.79 (m, 2H), 1.79-1.53 (m, 4H), 1.41 (d, 3H, J = 6.6 Hz), 1.20 (s, 9H). | 675 | 1.45 |

Example 8

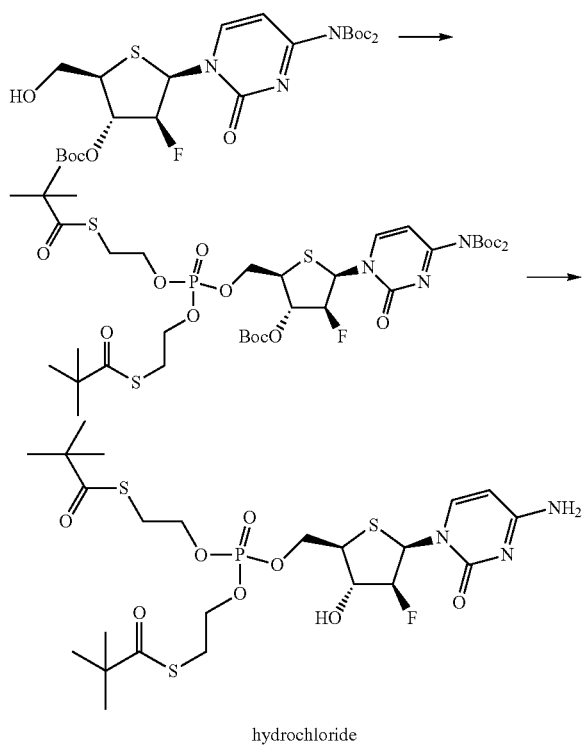

hydrochloride

First Step

A mixture of S,S'-(((((diisopropylamino)phosphinediyl)bis(oxy))bis(ethane-2,1-diyl)) bis(2,2-dimethylpropanethioate) (161 mg) and acetonitrile (0.5 mL) was added to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (100 mg), 1H-tetrazole (49.9 mg) and acetonitrile (0.5 mL) which was then stirred at room temperature for 21.5 hours. meta-Chloroperbenzoic acid (88.0 mg) was added to the reaction liquid which was then stirred at room temperature for 30 minutes. An aqueous saturated sodium hydrogen carbonate solution (1.0 mL) and sodium sulfite (10.0 mg) were added to the reaction liquid which was then stirred at room temperature for 0.5 hours and extracted with ethyl acetate. The organic layer was washed with an aqueous saturated sodium chloride solution and dried over anhydrous sodium sulfate. The solvent was distilled off under reduced pressure and the resulting residue was purified by silica gel column chromatography (hexane:ethyl acetate=71:29 to 50:50) to give ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(S-pivaloyl-2-mercaptoethan-1-yl) phosphate (54.0 mg) as a colorless oil.

MS (ESI m/z): 930 (M+H)
RT (min): 2.26

Second Step

Trifluoroacetic acid (0.5 mL) was added to a mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(S-pivaloyl-2-mercaptoethan-1-yl) phosphate (25.0 mg) and methylene chloride (0.5 mL) which was then allowed to stand at room temperature for 1 hour. The solvent was distilled off under reduced pressure. Ethyl acetate (1.0 mL) was added to the resulting residue which was then stirred, and a 4.0 mol/L hydrogen chloride/1,4-dioxane solution (10 μL) was added thereto. Hexane (0.5 mL) was added to the reaction liquid which was then stirred for 1 hour. Thereafter, the precipitated solid was collected by filtration to give a hydrochloride (12.0 mg) of ((2R,3S,4S,5R)-5-(4-amino-2-oxopyrimidin-1(2H)-yl)-4-fluoro-3-hydroxytetrahydrothiophen-2-yl)methyl bis(S-pivaloyl-2-mercaptoethan-1-yl) phosphate as a white solid.

$^1$H-NMR (DMSO-d$_6$) δ: 9.36-9.15 (m, 1H), 8.39-8.25 (m, 1H), 8.19 (d, 1H, J=7.6 Hz), 6.42 (dd, 1H, J=16.2, 5.0 Hz), 6.32-6.17 (m, 1H), 6.09 (d, 1H, J=7.6 Hz), 5.20-4.96 (m, 1H), 4.55-4.42 (m, 1H), 4.39-4.21 (m, 6H), 3.68-2.96 (m, 5H), 1.16 (s, 18H).

MS (ESI m/z): 630 (M+H)
RT (min): 1.32

Example 9-1

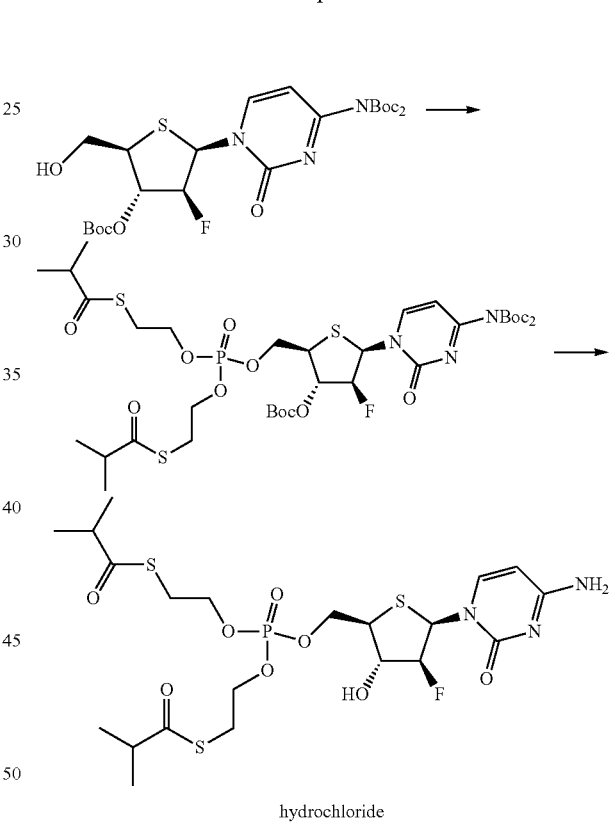

hydrochloride

First Step

A mixture of S,S'-(((((diisopropylamino)phosphinediyl)bis(oxy))bis(ethane-2,1-diyl)) bis(2-methylpropanethioate) (75.8 mg) and acetonitrile (0.4 mL) was added to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (50.0 mg), 1H-tetrazole (24.9 mg) and acetonitrile (0.5 mL) which was then stirred at room temperature for 18 hours. A mixture of iodine (57.4 mg), water (90 μL) and pyridine (0.9 mL) was added to the reaction liquid which was then stirred at room temperature for 1 hour. Sodium sulfite (10.0 mg) was added to the reaction liquid which was then stirred at room temperature for 0.5 hours and extracted with ethyl acetate. The organic layer was washed with an aqueous saturated sodium chloride solution and dried over anhydrous sodium sulfate. The solvent was distilled off under reduced pressure and the resulting residue was purified by silica gel column chromatography (hexane:ethyl acetate=70:30 to 50:50) to give ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(S-isobutyryl-2-mercaptoethan-1-yl) phosphate (63.3 mg) as a colorless oil.

MS (ESI m/z): 902 (M+H)
RT (min): 2.14
Second Step

Trifluoroacetic acid (0.5 mL) was added to a mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(S-isobutyryl-2-mercaptoethan-1-yl) phosphate (61.3 mg) and methylene chloride (0.5 mL) which was then stirred at room temperature for 1 hour. The solvent was distilled off under reduced pressure. A 4.0 mol/L hydrogen chloride/1,4-dioxane solution (26 µL) was added to a mixture of the resulting residue and ethyl acetate (1.0 mL) which was then stirred at room temperature for 30 minutes. Hexane (1.5 mL) was added to the reaction liquid which was then stirred for 1 hour, and the solvent was distilled off under reduced pressure. Ethyl acetate (1.0 mL) was added to the resulting residue which was then stirred for 30 minutes. Thereafter, the precipitated solid was collected by filtration to give a hydrochloride (13.7 mg) of ((2R,3S,4S,5R)-5-(4-amino-2-oxopyrimidin-1(2H)-yl)-4-fluoro-3-hydroxytetrahydrothiophen-2-yl)methyl bis(S-isobutyryl-2-mercaptoethan-1-yl) phosphate as a white solid.

MS (ESI m/z): 602 (M+H)
RT (min): 1.21

Example 9-2

Compounds of Table 8 and Table 9 were obtained in the same manner as in Example 9-1.

TABLE 8

| R | Compound name | MS (ESI m/z) (M + H) | RT (min) |
|---|---|---|---|
| 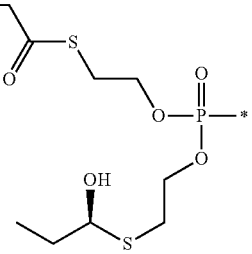 | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(S-propionyl-2-mercaptoethan-1-yl) phosphate | 874 | 2.01 |
| 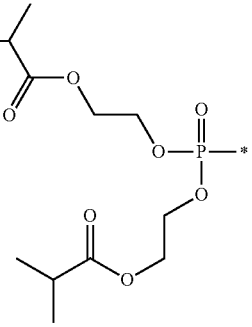 | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(isobutyryloxyethyl) phosphate | 870 | 1.99 |

TABLE 9

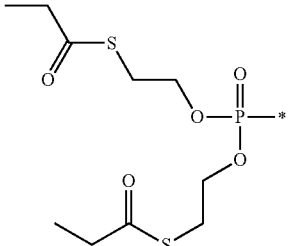

·hydrochloride

| Example No. | | Compound name | ¹H-NMR | MS (ESI m/z) (M + H) | RT (min) |
|---|---|---|---|---|---|
| 9-2-1 | 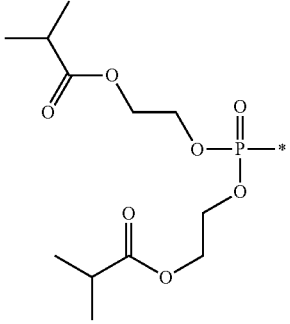 | ((2R,3S,4S,5R)-5-(4-amino-2-oxopyrimidin-1(2H)-yl)-4-fluoro-3-hydroxytetra-hydrothiophen-2-yl)methyl bis(S-propionyl-2-mercaptoethan-1-yl) phosphate | — | 574 | 1.03 |
| 9-2-2 | 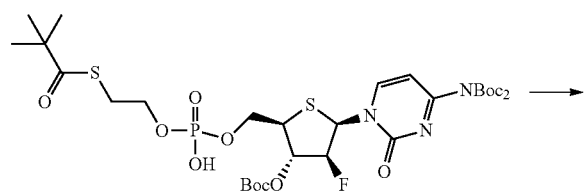 | ((2R,3S,4S,5R)-5-(4-amino-2-oxopyrimidin-1(2H)-yl)-4-fluoro-3-hydroxytetra-hydrothiophen-2-yl)methyl bis(isobutyryloxyethyl) phosphate | ¹H-NMR (CD$_3$OD) δ: 8.30 (dd, 1H, J = 7.6, 1.7 Hz), 6.61 (dd, 1H, J = 18.5, 4.6 Hz), 6.10 (d, 1H, J = 7.9 Hz), 5.17-4.94 (m, 1H), 4.51-4.01 (m, 11H), 3.69-3.61 (m, 1H), 2.69-2.54 (m, 2H), 1.17 (d, 12H, J = 7.3 Hz). | 570 | 1.04 |

Example 10-1

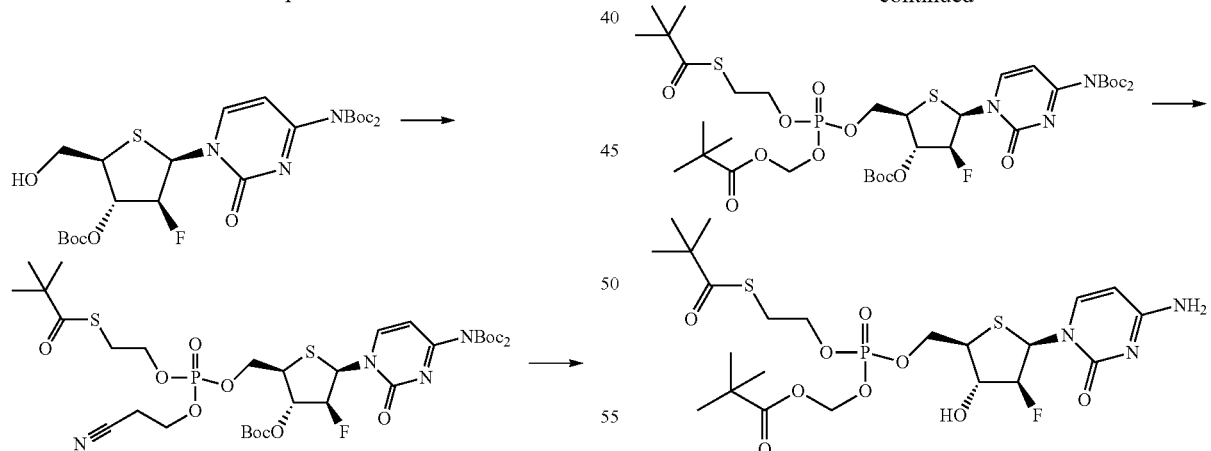

First Step (1) Under a nitrogen atmosphere, a mixture of S-(2-hydroxyethyl) 2,2-dimethylpropanethioate (137 mg) and tetrahydrofuran (0.5 mL) was added under ice-cooling to a mixture of 2-cyanoethyl N,N-diisopropylchlorophosphoramidite (200 mg), triethylamine (1.5 mL) and tetrahydrofuran (2.0 mL) which was then stirred at room temperature for 1.5 hours. The insoluble matter was separated by filtration, and the solvent was distilled off under reduced pressure to give S-(2-(((2-cyanoethoxy)(diisopropylamino)phosphino)oxy)ethyl) 2,2-dimethylpropanethioate.

(2) 1H-tetrazole (118 mg) was added to a mixture of S-(2-(((2-cyanoethoxy)(diisopropylamino)phosphino)oxy)ethyl) 2,2-dimethylpropanethioate obtained in (1), tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (316 mg) and tetrahydrofuran (3.0 mL) which was then stirred at room temperature for 2 hours. A mixture of iodine (214 mg), water (0.1 mL) and pyridine (1.0 mL) was added to the reaction liquid which was then stirred for 30 minutes. Sodium sulfite (213 mg) was added to the reaction liquid which was then extracted with ethyl acetate. The organic layer was washed with an aqueous saturated sodium chloride solution and dried over anhydrous sodium sulfate. The solvent was distilled off under reduced pressure to give S-(2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(2-cyanoethoxy)phosphoryl)oxy)ethyl) 2,2-dimethylpropanethioate (593 mg).

MS (ESI m/z): 839 (M+H)
RT (min): 2.05
Second Step
A mixture of S-(2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(2-cyanoethoxy)phosphoryl)oxy)ethyl) 2,2-dimethylpropanethioate (593 mg) and a 7.0 mol/L ammonia/methanol solution (3.0 mL) was stirred at room temperature for 1 hour. The solvent was distilled off under reduced pressure to give an ammonium salt (459 mg) of S-(2-(((((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(hydroxy)phosphoryl)oxy)ethyl) 2,2-dimethylpropanethioate.

MS (ESI m/z): 786 (M+H)
RT (min): 1.59
Third Step
A mixture of the ammonium salt (50.0 mg) of S-(2-(((((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(hydroxy)phosphoryl)oxy)ethyl) 2,2-dimethylpropanethioate, chloromethyl isopropyl carbonate (27 μL), N,N-diisopropylethylamine (43 μL) and N,N-dimethylformamide (0.5 mL) was stirred at 80° C. for 2 hours. Water was added at room temperature to the reaction liquid which was then extracted with ethyl acetate. The organic layer was washed with water and an aqueous saturated sodium chloride solution and dried over anhydrous sodium sulfate. The solvent was distilled off under reduced pressure to give (((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(2-(pivaloylthio)ethoxy)phosphoryl)oxy)methyl pivalate.

MS (ESI m/z): 900 (M+H)
RT (min): 2.21
Fourth Step
Trifluoroacetic acid (0.5 mL) was added to a mixture of (((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(2-(pivaloylthio)ethoxy)phosphoryl)oxy)methyl pivalate and methylene chloride (0.5 mL) which was then stirred at room temperature for 30 minutes. The solvent was distilled off under reduced pressure. Triethylamine (2.0 mL) was added to the resulting residue, and the solvent was distilled off under reduced pressure. The resulting residue was purified by silica gel column chromatography (chloroform:methanol=95:5 to 88:12) to give (((RS)-(((2R,3S,4S,5R)-5-(4-amino-2-oxopyrimidin-1(2H)-yl)-4-fluoro-3-hydroxytetrahydrothiophen-2-yl)methoxy)(2-(pivaloylthio)ethoxy)phosphoryl)oxy)methyl pivalate (12.8 mg) as a colorless oil.

$^1$H-NMR (CDCl$_3$) δ: 8.06-7.95 (m, 1H), 6.76-6.60 (m, 1H), 6.10-5.98 (m, 1H), 5.73-5.58 (m, 2H), 5.27-5.01 (m, 1H), 4.63-4.51 (m, 1H), 4.42-4.05 (m, 4H), 3.75-3.64 (m, 1H), 3.21-3.03 (m, 3H), 1.23 (s, 18H).

MS (ESI m/z): 600 (M+H)
RT (min): 1.35

Example 10-2

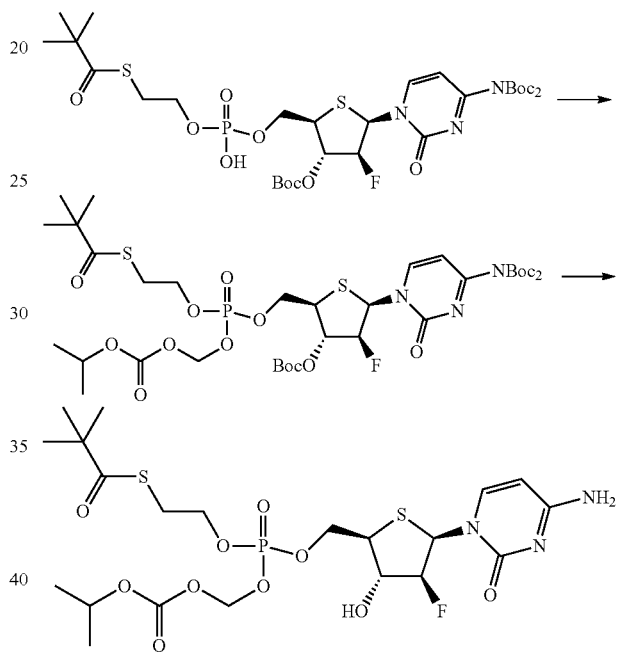

First Step
The following compound was obtained in the same manner as in the third step of Example 10-1.
S-(2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(((isopropoxy carbonyl)oxy)methoxy)phosphoryl)oxy)ethyl) 2,2-dimethylpropanethioate MS (ESI m/z): 902 (M+H)
RT (min): 2.14
Second Step
The following compound was obtained in the same manner as in the fourth step of Example 10-1.
S-(2-(((RS)-(((2R,3S,4S,5R)-5-(4-amino-2-oxopyrimidin-1(2H)-yl)-4-fluoro-3-hydroxytetrahydrothiophen-2-yl)methoxy)(((isopropoxycarbonyl)oxy)methoxy)phosphoryl)oxy)ethyl) 2,2-dimethylpropanethioate $^1$H-NMR (CDCl$_3$) δ: 8.03-7.92 (m, 1H), 6.85-6.72 (m, 1H), 5.99-5.89 (m, 1H), 5.72-5.60 (m, 2H), 5.27-5.03 (m, 1H), 5.01-4.86 (m, 1H), 4.66-4.52 (m, 1H), 4.42-4.07 (m, 4H), 3.75-3.64 (m, 1H), 3.21-3.08 (m, 2H), 1.32 (d, 6H, J=6.6 Hz), 1.24 (s, 9H).

MS (ESI m/z): 602 (M+H)
RT (min): 1.22

Example 11-1

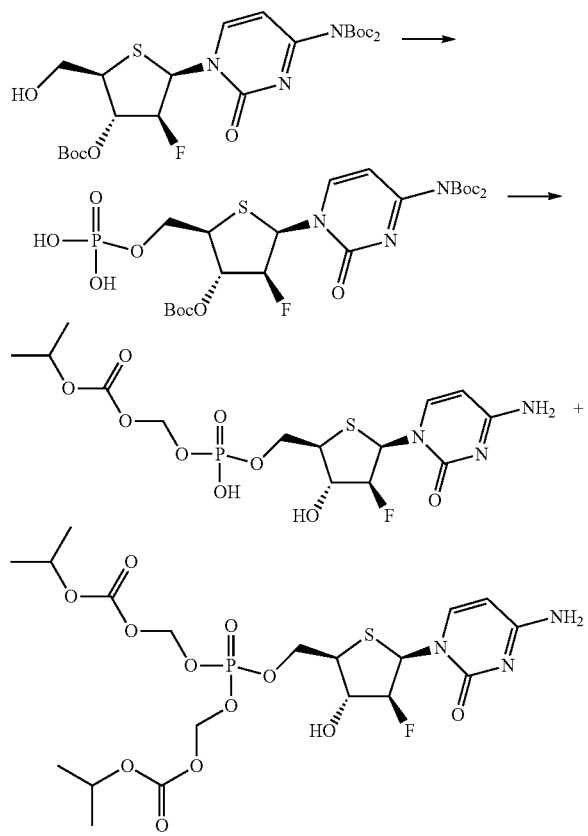

First Step

Under a nitrogen atmosphere, triethylamine (620 µL) was added at −78° C. to a mixture of phosphorus oxychloride (84 µL) and methylene chloride (2.2 mL), and then a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (500 mg) and methylene chloride (2.2 mL) was added thereto, followed by stirring for 1 hour. Water (0.5 mL) was added to the reaction liquid which was then stirred at room temperature for 1 hour and extracted with ethyl acetate. The organic layer was dried over anhydrous sodium sulfate and then the solvent was distilled off under reduced pressure. The resulting residue was purified by silica gel column chromatography (chloroform:methanol=95:5 to 70:30) to give ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl dihydrogen phosphate (306 mg).

MS (ESI m/z): 642 (M+H)
RT (min): 1.33

Second Step

A mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl dihydrogen phosphate (100 mg), chloromethyl isopropyl carbonate (124 µL), N,N-diisopropylethylamine (221 µL) and N,N-dimethylformamide (1.0 mL) was stirred at 60° C. for 4.5 hours, followed by stirring at 80° C. for 3 hours. Water was added at room temperature to the reaction liquid which was then extracted with ethyl acetate. The organic layer was washed with water and an aqueous saturated sodium chloride solution and dried over anhydrous sodium sulfate. The solvent was distilled off under reduced pressure. Trifluoroacetic acid (0.5 mL) was added to a mixture of the resulting residue and methylene chloride (0.5 mL) which was then stirred at room temperature for 1 hour. The solvent was distilled off under reduced pressure. Triethylamine (2.0 mL) was added to the resulting residue, and the solvent was distilled off under reduced pressure. The resulting residue was purified by silica gel column chromatography (chloroform:methanol=100:0 to 70:30) to give (((((2R,3S,4S,5R)-5-(4-amino-2-oxopyrimidin-1(2H)-yl)-4-fluoro-3-hydroxytetrahydrothiophen-2-yl)methoxy)(hydroxy)phosphoryl)oxy)methyl isopropyl carbonate (2.8 mg) and ((2R,3S,4S,5R)-5-(4-amino-2-oxopyrimidin-1(2H)-yl)-4-fluoro-3-hydroxytetrahydrothiophen-2-yl)methyl bis(isopropyloxycarbonyloxymethyl) phosphate (1.8 mg) as a colorless oil.

Example 11-1-1

(((((2R,3S,4S,5R)-5-(4-amino-2-oxopyrimidin-1(2H)-yl)-4-fluoro-3-hydroxytetrahydrothiophen-2-yl)methoxy)(hydroxy)phosphoryl)oxy)methyl isopropyl carbonate $^1$H-NMR (CD$_3$OD) δ: 8.31-8.23 (m, 1H), 6.62-6.52 (m, 1H), 5.99-5.92 (m, 1H), 5.57-5.47 (m, 2H), 5.09-4.89 (m, 1H), 4.51-4.38 (m, 1H), 4.15-4.05 (m, 2H), 3.55-3.26 (m, 2H), 1.27 (d, 6H, J=5.9 Hz).

MS (ESI m/z): 458 (M+H)
RT (min): 0.63

Example 11-1-2

((2R,3S,4S,5R)-5-(4-amino-2-oxopyrimidin-1(2H)-yl)-4-fluoro-3-hydroxytetrahydrothiophen-2-yl)methyl bis(isopropyloxycarbonyloxymethyl) phosphate $^1$H-NMR (CDCl$_3$) δ: 8.00 (dd, 1H, J=7.6, 1.7 Hz), 6.84 (dd, 1H, J=21.8, 4.0 Hz), 5.78 (d, 1H, J=7.6 Hz), 5.74-5.61 (m, 5H), 5.24-5.02 (m, 1H), 5.01-4.87 (m, 2H), 4.66-4.58 (m, 1H), 4.39-4.28 (m, 2H), 3.72-3.59 (m, 1H), 1.33 (d, 12H).

MS (ESI m/z): 574 (M+H)
RT (min): 1.08

Example 11-2

Compounds of Table 10 were obtained in the same manner as in the second step of Example 11-1.

TABLE 10

| Example No. | R | Compound name | ¹H-NMR | MS (ESI m/z) (M + H) | RT (min) |
|---|---|---|---|---|---|
| 11-2-1 | | (((((2R,3S,4S,5R)-5-(4-amino-2-oxopyrimidin-1(2H)-yl)-4-fluoro-3-hydroxytetrahydrothiophen-2-yl)methoxy)(hydroxy) phosphoryl)oxy)methyl pivalate | ¹H-NMR (CD₃OD) δ: 8.25 (dd, 1H, J = 7.3, 1.3 Hz), 6.59 (dd, 1H, J = 14.5, 5.3 Hz), 5.97 (d, 1H, J = 7.3 Hz), 5.61-5.48 (m, 2H), 5.10-4.88 (m, 1H), 4.50-4.38 (m, 1H), 4.18-4.07 (m, 2H), 3.56-3.44 (m, 1H), 1.22 (s, 9H). | 456 | 0.71 |
| 11-2-2 | | ((2R,3S,4S,5R)-5-(4-amino-2-oxopyrimidin-1(2H)-yl)-4-fluoro-3-hydroxytetrahydrothiophen-2-yl)methyl bis(pivaloyloxymethyl) phosphate | ¹H-NMR (CDCl₂) δ: 8.00 (dd, 1H, J = 7.3, 2.0 Hz), 6.85 (dd, 1H, J = 21.8, 4.0 Hz), 5.75-6.48 (m, 1H), 5.77 (d, 1H, J = 7.3 Hz), 5.74-5.59 (m, 4H), 5.25-5.02 (m, 1H), 4.75 (d, 2H, J = 5.9 Hz), 4.65-4.56 (m, 1H), 4.35-4.25 (m, 2H), 3.69-3.60 (m, 1H), 1.24 (s, 18H). | 570 | 1.17 |
| 11-2-3 | | ((2R,3S,4S,5R)-5-(4-amino-2-oxopyrimidin-1(2H)-yl)-4-fluoro-3-hydroxytetrahydrothiophen-2-yl)methyl bis(1-isopropyloxy-carbonyloxyethan-1-yl) phosphate | ¹H-NMR (CD₃OD) δ: 8.15-8.08 (m, 1H), 6.75-6.62 (m, 1H), 6.50-6.37 (m, 2H), 5.99 (d, 1H, J = 7.9 Hz), 5.13-5.00 (m, 1H), 4.53-4.26 (m, 3H), 3.76-3.56 (m, 3H), 1.62-1.55 (m, 6H), 1.41-1.27 (m, 12H). | 602 | 1.20 |

Example 12-1

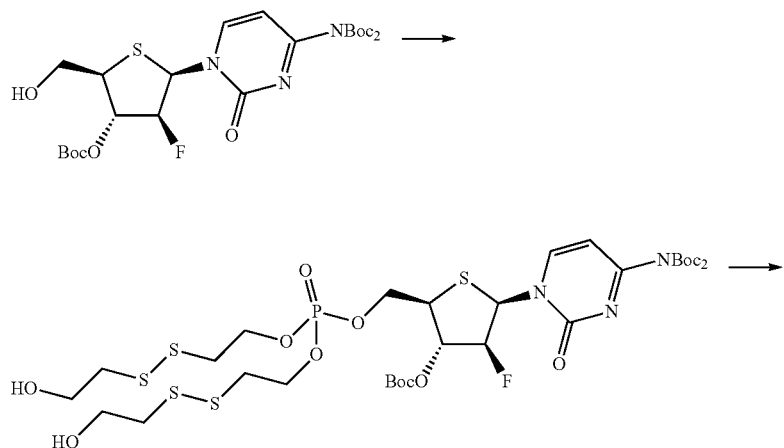

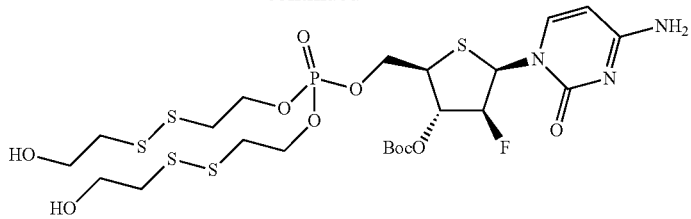

First Step

Under a nitrogen atmosphere, triethylamine (620 μL) was added at −78° C. to a mixture of phosphorus oxychloride (84 μL) and methylene chloride (2.2 mL), and then a mixture of tert-butyl tert-butoxycarbonyl(1-((2R,3S,4S,5R)-4-((tert-butoxycarbonyl)oxy)-3-fluoro-5-(hydroxymethyl)-tetrahydrothiophen-2-yl)-2-oxo-1,2-dihydropyrimidin-4-yl)carbamate (500 mg) and methylene chloride (2.2 mL) was added thereto, followed by stirring for 1 hour. A mixture of 2,2'-disulfanediyldiethanol (685 mg) and methylene chloride (2.2 mL) was added at −78° C. to the reaction liquid which was then stirred for 1.5 hours, followed by stirring at room temperature for 3 hours. Water was added to the reaction liquid which was then stirred for 2 hours and extracted with ethyl acetate. The organic layer was washed with an aqueous saturated sodium chloride solution and dried over anhydrous sodium sulfate, and then the solvent was distilled off under reduced pressure. The resulting residue was purified by silica gel column chromatography (chloroform:methanol=100:0 to 70:30) to give ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-hydroxyethyl)disulfanyl)ethyl) phosphate (218 mg) as a yellow solid.

MS (ESI m/z): 914 (M+H)
RT (min): 1.71

Second Step

Trifluoroacetic acid (0.5 mL) was added to a mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-hydroxyethyl)disulfanyl)ethyl) phosphate (50.0 mg) and methylene chloride (0.5 mL) which was then stirred at room temperature for 1 hour. The solvent was distilled off under reduced pressure. Triethylamine (2.0 mL) was added to the resulting residue, and the solvent was distilled off under reduced pressure. The resulting residue was purified by silica gel column chromatography (chloroform:methanol=90:10 to 70:30) to give ((2R,3S,4S,5R)-5-(4-amino-2-oxopyrimidin-1(2H)-yl)-4-fluoro-3-hydroxytetrahydrothiophen-2-yl) methyl bis(2-((2-hydroxyethyl)disulfanyl)ethyl) phosphate (2.6 mg) as a colorless oil.

$^1$H-NMR (CD$_3$OD) δ: 8.08 (dd, 1H, J=7.3, 2.0 Hz), 6.69 (dd, 1H, J=19.5, 4.3 Hz), 5.94 (d, 1H, J=7.3 Hz), 5.12-4.89 (m, 1H), 4.51-4.26 (m, 7H), 3.79 (t, 4H, J=6.3 Hz), 3.68-3.59 (m, 1H), 3.04 (t, 4H, J=6.3 Hz), 2.87 (t, 4H, J=6.3 Hz).

MS (ESI m/z): 614 (M+H)
RT (min): 0.80

Example 12-2

Compounds of Table 11 and Table 12 were obtained in the same manner as in Example 12-1.

TABLE 11

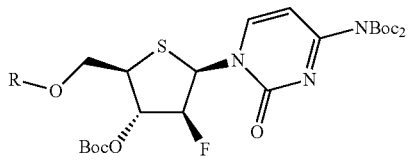

| R | Compound name | MS (ESI m/z) (M + H) | RT (min) |
|---|---|---|---|
| HO~S-S~O-P(=O)(OH)-* | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl (2-((2-hydroxyethyl)disulfanyl)ethyl) hydrogen phosphate | 778 | 1.33 |

TABLE 11-continued

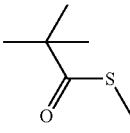

| R | Compound name | MS (ESI m/z) (M + H) | RT (min) |
|---|---|---|---|
| 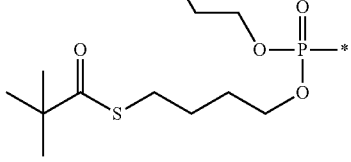 | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(S-pivaloyl-4-mercaptobutan-1-yl) phosphate | 986 | 2.37 |
|  | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-methoxyethyl)disulfanyl)ethyl) phosphate | 942 | 2.03 |
|  | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-(benzyloxy)ethyl)disulfanyl)ethyl) phosphate | 1094 | 2.29 |

TABLE 12

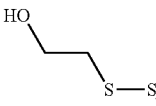

| Example No. | R | Compound name | ¹H-NMR | MS (ESI m/z) (M + H) | RT (min) |
|---|---|---|---|---|---|
| 12-2-1 | 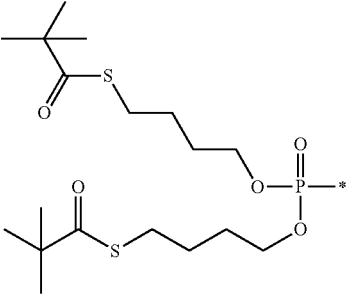 | ((2R,3S,4S,5R)-5-(4-amino-2-oxopyrimidin-1(2H)-yl)-4-fluoro-3-hydroxytetrahydrothiophen-2-yl)methyl (2-((2-hydroxyethyl)disulfanyl)ethyl) hydrogen phosphate | ¹H-NMR (MeOD) δ: 8.33-8.26 (m, 1H), 6.57 (dd, 1H, J = 13.2, 5.3 Hz), 5.99 (d, 1H, J = 7.3 Hz), 5.12-4.90 (m, 1H), 4.49-4.38 (m, 1H), 4.21-4.04 (m, 4H), 3.79 (t, 2H, J = 6.6 Hz), 3.52-3.44 (m, 1H), 2.98 (t, 2H), J = 6.6 Hz), 2.85 (t, 2H), J = 6.3 Hz). | 478 | 0.55 |
| 12-2-2 | 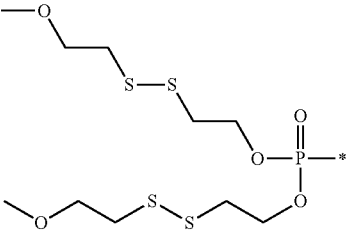 | ((2R,3S,4S,5R)-5-(4-amino-2-oxopyrimidin-1(2H)-yl)-4-fluoro-3-hydroxytetrahydrothiophen-2-yl)methyl bis(S-pivaloyl-4-mercaptobutan-1-yl) phosphate | ¹H-NMR (MeOD) δ: 9.08 (dd, 1H, J = 7.6, 2.0 Hz), 5.68 (dd, 1H, J = 19.2, 4.6 Hz), 5.93 (d, 1H, J = 7.6 Hz), 5.11-4.89 (m, 1H), 4.40-4.41 (m, 1H), 4.41-4.21 (m, 2H), 4.19-4.08 (m, 4H), 3.68-3.56 (m, 1H), 2.89 (t, 4H, J = 7.3 Hz), 1.85-1.62 (m, 8H), 1.21 (m, 18H). | 686 | 1.58 |
| 12-2-3 | | ((2R,3S,4S,5R)-5-(4-amino-2-oxopyrimidin-1(2H)-yl)-4-fluoro-3-hydroxytetrahydrothiophen-2-yl)methyl bis(2-((2-methoxyethyl)disulfanyl)ethyl) phosphate | ¹H-NMR (MeOD) δ: 8.08 (dd, 1H, J = 7.9, 2.0 Hz), 6.59 (dd, 1H, J = 19.8, 4.6 Hz), 5.93 (d, 1H, J = 7.9 Hz), 5.12-4.90 (m, 1H), 4.51-4.25 (m, 1H), 3.78 (t, 4H, J = 6.6 Hz), 3.17-3.60 (m, 1H), 3.35 (s, 6H), 3.03 (t, 4H, J = 6.3 Hz), 2.93 (t, 1H), J = 6.3 Hz). | 642 | 1.10 |
| 12-2-4 | 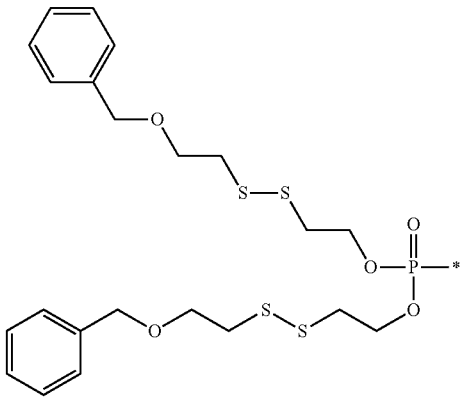 | ((2R,3S,4S,5R)-5-(4-amino-2-oxopyrimidin-1(2H)-yl)-4-fluoro-3-hydroxytetrahydrothiophen-2-yl)methyl bis(2-((2-benzyloxy)ethyl)disulfanyl)ethyl) phosphate | ¹H-NMR (MeOD) δ: 8.05 (dd, 1H, J = 7.0, 1.3 Hz), 7.38-7.21 (m, 10H), 5.08 (dd, 1H, J = 18.2, 4.6 Hz), 6.91 (d, 1H, J = 7.9 Hz), 5.09-4.69 (m, 1H), 4.53 (m, 1H), 4.48-4.23 (m, 7H), 3.73 (t, 4H, J = 5.9 Hz), 3.70-3.50 (m, 1H), 3.01-2.92 (m, 8H). | 794 | 1.60 |

Example 13-1

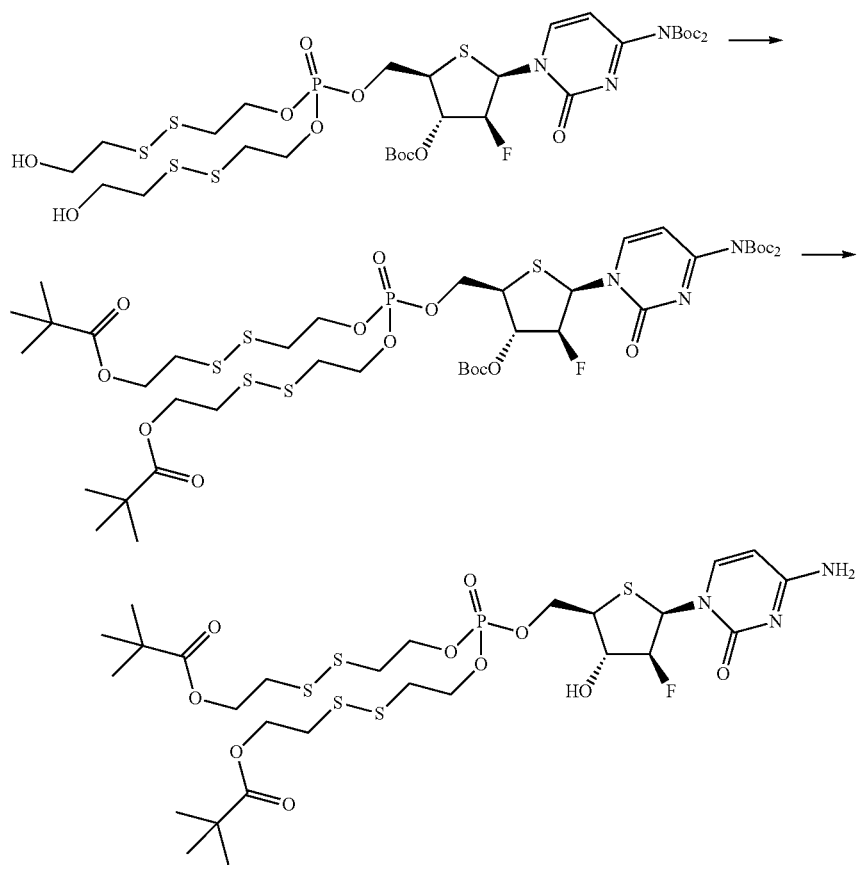

First Step

Pivaloyl chloride (36 μL) was added under ice-cooling to a mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-hydroxyethyl)disulfanyl)ethyl) phosphate (100 mg), triethylamine (68.7 μL) and tetrahydrofuran (1.0 mL) which was then stirred at room temperature for 2.5 hours. Triethylamine (137 μL) and pivaloyl chloride (73 μL) were added under ice-cooling to the reaction liquid which was then stirred at room temperature for 5 hours, and an aqueous saturated sodium hydrogen carbonate solution was added thereto, followed by stirring for 30 minutes and extraction with ethyl acetate. The organic layer was washed with an aqueous saturated sodium chloride solution and dried over anhydrous sodium sulfate, and then the solvent was distilled off under reduced pressure to give ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-pivaloyloxyethyl)disulfanyl)ethyl) phosphate.

MS (ESI m/z): 1082 (M+H)
RT (min): 2.33

Second Step

Trifluoroacetic acid (1.0 mL) was added to a mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-pivaloyloxyethyl)disulfanyl)ethyl) phosphate obtained in the first step and methylene chloride (1.0 mL) which was then stirred at room temperature for 1 hour. The solvent was distilled off under reduced pressure. Triethylamine (2.0 mL) was added to the resulting residue, and the solvent was distilled off under reduced pressure. The resulting residue was purified by silica gel column chromatography (chloroform:methanol=94:6 to 70:30) to give ((2R,3S,4S,5R)-5-(4-amino-2-oxopyrimidin-1(2H)-yl)-4-fluoro-3-hydroxytetrahydrothiophen-2-yl)methyl bis(2-((2-pivaloyloxyethyl)disulfanyl)ethyl) phosphate (1.7 mg) as a colorless oil.

$^1$H-NMR (CD$_3$OD) δ: 8.07 (dd, 1H, J=7.3, 2.0 Hz), 6.69 (dd, 1H, J=19.5, 4.3 Hz), 5.93 (d, 1H, J=7.3 Hz), 5.11-4.90 (m, 1H), 4.51-4.26 (m, 11H), 3.70-3.59 (m, 1H), 3.05 (t, 4H, J=5.9 Hz), 2.99 (t, 4H, J=6.3 Hz), 1.20 (s, 18H).

MS (ESI m/z): 782 (M+H)
RT (min): 1.67

Example 13-2

Compounds of Table 13 and Table 14 were obtained in the same manner as in Example 13-1.

TABLE 13

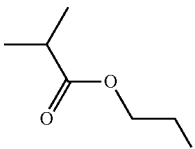

| R | Compound name | MS (ESI m/z) (M + H) | RT (min) |
|---|---|---|---|
| 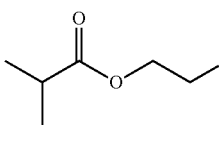 | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-isobutyroyloxyethyl)disulfanyl)ethyl) phosphate | 1054 | 2.22 |
| 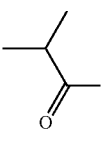 | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl bis(2-((2-acetoxyethyl)disulfanyl)ethyl) phosphate | 998 | 1.99 |

TABLE 14

| Example No. | R | Compound name | $^1$H-NMR | MS (ESI m/z) (M + H) | RT (min) |
|---|---|---|---|---|---|
| 13-2-1 | | ((2R,3S,4S,5R)-5-(4-amino-2-oxopyrimidin-1(2H)-yl)-4-fluoro-3-hydroxytetrahydrothiophen-2-yl)methyl bis(2-((2-isobutyroyloxyethyl)disulfanyl)ethyl) phosphate | $^1$H-NMR (MeOD) δ: 8.07 (dd, 1H, J = 7.9, 2.0 Hz), 6.59 (dd, 1H, J = 19.5, 4.3 Hz), 5.93 (d, 1H, J = 7.9 Hz), 5.11-4.88 (m, 1H), 4.51-4.28 (m, 11H), 3.68-3.60 (m, 1H), 3.06 (t, 4H, J = 6.3 Hz), 2.99 (t, 4H, J = 6.6 Hz), 2.56-2.49 (m, 2H), 1.16 (d, 12H, J = 7.3 Hz). | 754 | 1.50 |

TABLE 14-continued

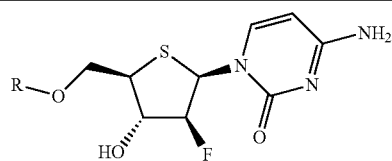

| Example No. | R | Compound name | ¹H-NMR | MS (ESI m/z) (M + H) | RT (min) |
|---|---|---|---|---|---|
| 13-2-2 | ![structure] | ((2R,3S,4S,5R)-5-(4-amino-2-oxopyrimidin-1(2H)-yl)-4-fluoro-3-hydroxytetrahydro-thiophen-2-yl)methyl bis (2-((2-acetoxyethyl) disulfanyl)ethyl) phosphate | ¹H-NMR (MeOD) δ: 8.09 (dd, 1H, J = 7.9, 2.0 Hz), 6.69 (dd, 1H, J = 19.2, 4.6 Hz), 5.93 (d, 1H, J = 7.3 Hz), 5.13-4.87 (m, 1H), 4.53-4.25 (m, 11H), 3.69-3.59 (m, 1H), 3.05 (t, 4H, J = 6.3 Hz), 2.98 (t, 1H, J = 6.6 Hz), 2.05 (s, 6H). | 698 | 1.15 |

Example 14-1

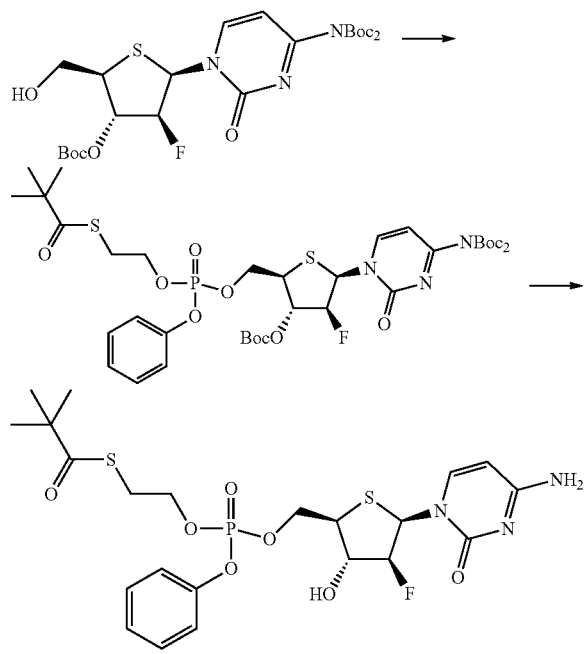

First Step (1) Under a nitrogen atmosphere, a mixture of S-(2-hydroxyethyl) 2,2-dimethylpropanethioate (57.8 mg) and methylene chloride (1.0 mL) was added under ice-cooling to a mixture of phenyl dichlorophosphate (58 μL), triethylamine (99 μL) and methylene chloride (1.0 mL) which was then stirred for 2 hours under ice-cooling. The solvent was distilled off under reduced pressure, methyl tert-butyl ether (5.0 mL) was added, and the insoluble matter was separated by filtration. The solvent was distilled off under reduced pressure to give S-(2-(((RS)-chloro(phenoxy)phosphoryl)oxy)ethyl) 2,2-dimethylpropanethioate.

(2) Under a nitrogen atmosphere, a 1.0 mol/L tert-butyl magnesium chloride/tetrahydrofuran solution (214 μL) was added at −78° C. to a mixture of tert-butyl tert-butoxycarbonyl(1-((2R,3S,4S,5R)-4-((tert-butoxycarbonyl)oxy)-3-fluoro-5-(hydroxymethyl)-tetrahydrothiophen-2-yl)-2-oxo-1,2-dihydropyrimidin-4-yl)carbamate (100 mg) and tetrahydrofuran (1.0 mL) which was then stirred for 30 minutes. A mixture of S-(2-((chloro(phenoxy)phosphoryl)oxy)ethyl)2,2-dimethylpropanethioate obtained in (1) and tetrahydrofuran (1.0 mL) was added to the reaction liquid which was then stirred at room temperature for 42 hours. Water was added to the reaction liquid which was then extracted with ethyl acetate, and the organic layer was washed with an aqueous saturated sodium chloride solution and dried over anhydrous sodium sulfate. The solvent was distilled off under reduced pressure to give S-(2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl) oxy)ethyl) 2,2-dimethylpropanethioate as a crude product.

MS (ESI m/z): 862 (M+H)

RT (min): 2.18

Second Step

Trifluoroacetic acid (0.5 mL) was added to a mixture of S-(2-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl) oxy)ethyl) 2,2-dimethylpropanethioate obtained in the first step and methylene chloride (0.5 mL) which was then stirred at room temperature for 1 hour. The solvent was distilled off under reduced pressure. An aqueous saturated sodium hydrogen carbonate solution was added to the resulting residue which was then extracted with ethyl acetate. The organic layer was washed with an aqueous saturated sodium chloride solution and dried over anhydrous sodium sulfate, and the solvent was distilled off under reduced pressure. The resulting residue was purified by silica gel column chromatography (chloroform:methanol=100:0 to 70:30) to give S-(2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)oxy)ethyl) 2,2-dimethylpropanethioate (1.7 mg) as a colorless oil.

¹H-NMR (CD₃OD) δ: 8.08-7.99 (m, 1H), 7.46-7.21 (m, 5H), 6.73-6.62 (m, 1H), 5.89 (d, 1H, J=7.3 Hz), 5.37-5.04 (m, 1H), 4.55-4.32 (m, 3H), 4.31-4.20 (m, 2H), 3.68-3.58 (m, 1H), 3.19 (t, 2H, J=6.3 Hz), 1.24-1.15 (m, 9H).

MS (ESI m/z): 562 (M+H)

RT (min): 1.28

Example 14-2

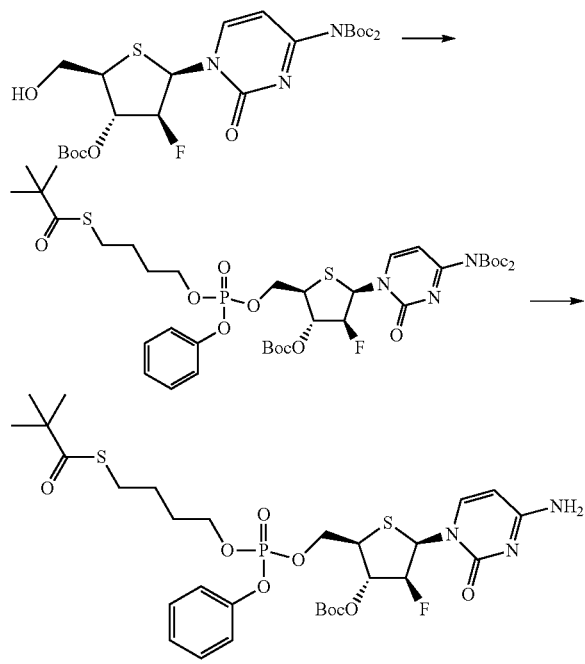

First Step

The following compound was obtained in the same manner as in the first step of Example 14-1.

S-(4-(((RS)-(((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methoxy)(phenoxy)phosphoryl)oxy)butyl) 2,2-dimethylpropanethioate MS (ESI m/z): 890 (M+H)

RT (min): 2.24

Second Step

The following compound was obtained in the same manner as in the second step of Example 14-1.

S-(4-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)oxy)butyl) 2,2-dimethylpropanethioate ¹H-NMR (CD₃OD) δ: 8.08-7.99 (m, 1H), 7.46-7.19 (m, 5H), 6.73-6.61 (m, 1H), 5.89 (d, 1H, J=7.9 Hz), 5.10-4.96 (m, 1H), 4.53-4.31 (m, 3H), 4.29-4.19 (m, 2H), 3.68-3.58 (m, 1H), 2.86 (t, 2H, J=6.9 Hz), 1.84-1.55 (m, 4H), 1.21 (s, 9H).

MS (ESI m/z): 590 (M+H)

RT (min): 1.38

Example 15-1

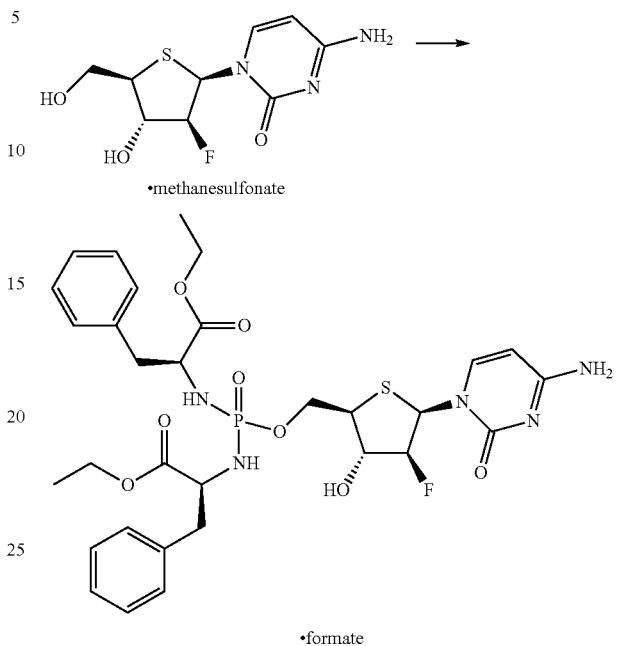

Triethylamine (775 μL) was added at −78° C. to a mixture of L-phenylalanine ethyl ester hydrochloride (644 mg), phosphorus oxychloride (130 μL) and methylene chloride (5.6 mL) which was then stirred at room temperature for 25 minutes. Methanesulfonate (100 mg) of 4-amino-1-((2R,3S,4S,5R)-3-fluoro-4-hydroxy-5-(hydroxymethyl)tetrahydrothiophen-2-yl)pyrimidin-2(1H)-one and triethylamine (775 μL) were added to the reaction liquid which was then stirred at room temperature for 3 hours, and an aqueous saturated ammonium chloride solution was added thereto, followed by extraction with chloroform and drying over magnesium sulfate. The solvent was distilled off under reduced pressure and the resulting residue was purified by silica gel column chromatography (ethyl acetate:methanol=100:0 to 85:15) to give a colorless oil. The resulting colorless oil was purified by reverse phase preparative HPLC (0.1% aqueous formic acid solution-0.1% formic acid acetonitrile solution) to give a formate (3.2 mg) of ((2R,3S,4S,5R)-5-(4-amino-2-oxopyrimidin-1(2H)-yl)-4-fluoro-3-hydroxytetrahydrothiophen-2-yl)methyl N,N'-bis((1S)-1-ethoxycarbonyl-2-phenylethan-1-yl)phosphorodiamidate as a colorless oil.

¹H-NMR (CD₃OD) δ: 8.32 (d, 1H, J=7.6 Hz), 8.12 (s, 1H), 7.28-7.04 (m, 10H), 6.62-6.49 (m, 1H), 5.92 (d, 1H, J=7.6 Hz), 5.19-4.93 (m, 1H), 4.50-4.37 (m, 1H), 4.22-4.07 (m, 4H), 4.01-3.90 (m, 2H), 3.87-3.80 (m, 2H), 3.44-3.33 (m, 1H), 3.27-3.13 (m, 4H), 1.39-1.18 (m, 3H), 1.14-1.02 (m, 3H).

MS (ESI m/z): 692 (M+H)

RT (min): 1.27

Example 15-2

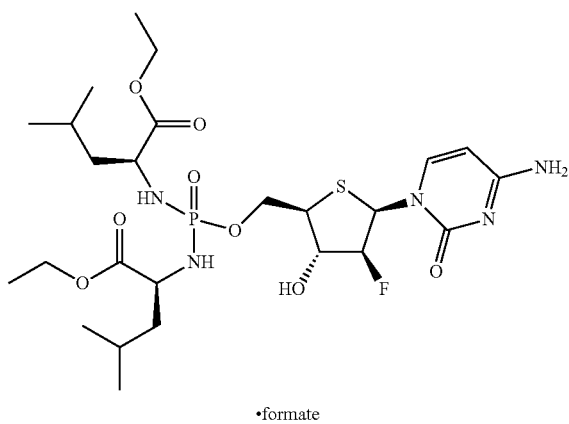 [SMILES: CCOC(=O)[C@H](CC(C)C)NP(=O)(N[C@@H](CC(C)C)C(=O)OCC)OC[C@H]1S[C@@H](n2ccc(N)nc2=O)[C@@H](F)[C@@H]1O]

·formate

The following compound was obtained in the same manner as in Example 15-1.

A formate of ((2R,3S,4S,5R)-5-(4-amino-2-oxopyrimidin-1(2H)-yl)-4-fluoro-3-hydroxytetrahydrothiophen-2-yl)methyl N,N'-bis((1S)-1-ethoxycarbonyl-3-methylbutan-1-yl)phosphorodiamidate $^1$H-NMR (CD$_3$OD) δ: 8.55-8.42 (m, 1H), 6.61-6.48 (m, 1H), 6.24-6.11 (m, 1H), 5.13-4.90 (m, 1H), 4.45-4.31 (m, 1H), 4.17 (q, 2H, J=7.0 Hz), 4.02 (q, 2H, J=7.3 Hz), 3.96-3.76 (m, 4H), 3.42-3.32 (m, 1H), 1.92-1.75 (m, 1H), 1.75-1.60 (m, 1H), 1.60-1.45 (m, 4H), 1.35-1.09 (m, 6H), 1.01-0.91 (m, 6H), 0.91-0.76 (m, 6H).

MS (ESI m/z): 624 (M+H)

RT (min): 1.27

Example 16-1

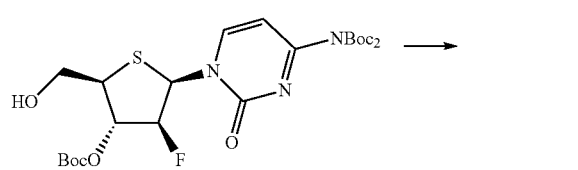

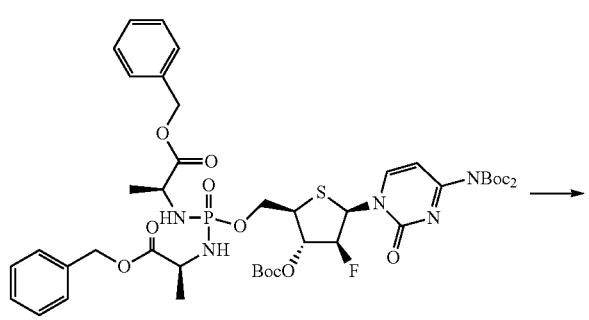

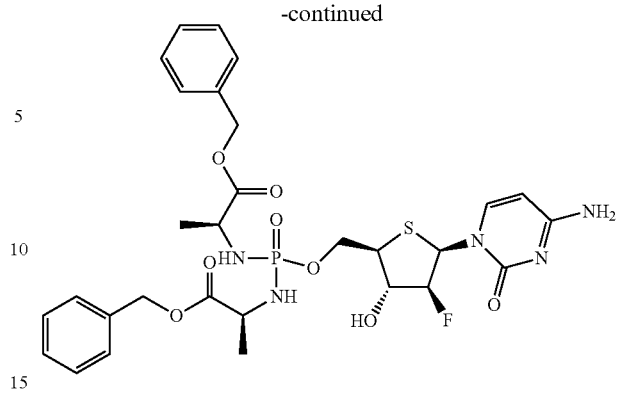

First Step

Under a nitrogen atmosphere, triethylamine (248 μL) was added at −78° C. to a mixture of phosphorus oxychloride (17 μL) and methylene chloride (0.9 mL), and then a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (50.0 mg) and methylene chloride (0.9 mL) was added thereto, followed by stirring for 30 minutes. A mixture of L-alanine benzyl ester hydrochloride (76.8 mg) and methylene chloride (1.7 mL) was added at −78° C. to the reaction liquid which was then stirred for 20 minutes, followed by stirring at room temperature for 30 minutes. Water was added to the reaction liquid which was then extracted with ethyl acetate, and the organic layer was washed with an aqueous saturated sodium chloride solution and dried over anhydrous sodium sulfate. The solvent was distilled off under reduced pressure to give ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl N,N'-bis((1S)-1-benzyloxycarbonylethan-1-yl)phosphorodiamidate.

MS (ESI m/z): 964 (M+H)

RT (min): 2.05

Second Step

Trifluoroacetic acid (0.5 mL) was added to a mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl N,N'-bis((1S)-1-benzyloxycarbonylethan-1-yl)phosphorodiamidate and methylene chloride (0.5 mL) which was then stirred at room temperature for 1.5 hours. The solvent was distilled off under reduced pressure. An aqueous saturated sodium hydrogen carbonate solution was added to the resulting residue which was then extracted with ethyl acetate. The organic layer was washed with an aqueous saturated sodium chloride solution and dried over anhydrous sodium sulfate. The solvent was distilled off under reduced pressure and the resulting residue was purified by basic silica gel column chromatography (chloroform:methanol=94:6 to 86:14) to give ((2R,3S,4S,5R)-5-(4-amino-2-oxopyrimidin-1(2H)-yl)-4-fluoro-3-hydroxytetrahydrothiophen-2-yl)methyl N,N'-bis((1S)-1-benzyloxycarbonylethan-1-yl)phosphorodiamidate (6.0 mg) as a white solid.

$^1$H-NMR (DMSO-d$_6$) δ: 7.88-7.82 (m, 1H), 7.39-7.18 (m, 12H), 6.53 (dd, 1H, J=17.8, 4.6 Hz), 6.01 (d, 1H, J=4.6 Hz), 5.79 (d, 1H, J=7.3 Hz), 5.16-4.81 (m, 7H), 4.36-4.25 (m, 1H), 4.18-4.05 (m, 1H), 3.99-3.76 (m, 3H), 3.52-3.24 (m, 1H), 1.33-1.21 (m, 6H).

MS (ESI m/z): 664 (M+H)

RT (min): 1.21

Example 16-2

Compounds of Table 15 and Table 16 were obtained in the same manner as in Example 16-1.

TABLE 15

| R | Compound name | MS (ESI m/z) (M + H) | RT (min) |
|---|---|---|---|
| (methyl ester, alanine) | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl N,N'-bis((1S)-1-methoxycarbonylethan-1-yl) phosphorodiamidate | 812 | 1.72 |
| (isopropyl ester, alanine) | ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl N,N'-bis((1S)-1-isopropoxycarbonylethan-1-yl) phosphorodiamidate | 868 | 1.97 |
| (tert-butyl ester, alanine) | ((2R,3S,4S,5R)-5-(4-(bis(tert-butoxycarbonyl)amino-2-oxopyrimidin-1(2H)-yl)-3-((tert-butoxycarbonyl)oxy)-4-fluorotetrahydrothiophen-2-yl)methyl N,N'-bis((1S)-1-tert-butoxycarbonylethan-1-yl)phosphorodiamidate | 896 | 2.10 |
| (dibenzyl) | ((2R,3S,4S,5R)-5-(4-bis(tert-butoxycarbonyl)amino)-2-oxopyrimidin-1(2H)-yl)-3-((tert-butoxycarbonyl)oxy)-4-fluorotetrahydrothiophen-2-yl)methyl N,N'-dibenzylphosphorodiamidate | 820 | 1.95 |

TABLE 16

| Example No. | R | Compound name | ¹H-NMR | MS (ESI m/z) (M + H) | RT (min) |
|---|---|---|---|---|---|
| 16-2-1 | | ((2R,3S,4S,5R)-5-(4-amino-2-oxopyrimidin-1(2H)-yl)-4-fluoro-3-hydroxytetrahydrothiophen-2-yl)methyl N,N'-bis((1S)-1-methoxycarbonylethan-1-yl)phosphorodiamidate | ¹H-NMR (DMSO-d₆) δ: 7.88 (dd, 1H, J = 7.6, 1.7 Hz), 7.37-7.17 (m, 2H), 6.53 (dd, 1H, J = 17.8, 4.6 Hz), 5.79 (d, 1H, J = 7.3 Hz), 5.06-4.83 (m, 3H), 4.36-4.25 (m, 1H), 4.18-4.05 (m, 1H), 4.01-3.89 (m, 1H), 3.87-3.70 (m, 2H), 3.65-3.58 (m, 6H), 3.50-3.22 (m, 1H), 1.32-1.20 (m, 5H). | 512 | 0.66 |
| 16-2-2 | | ((2R,3S,4S,5R)-5-(4-amino-2-oxopyrimidin-1(2H)-yl)-4-fluoro-3-hydroxytetrahydrothiophen-2-yl)methyl N,N'-bis((1S)-1-isopropoxycarbonylethan-1-yl)phosphorodiamidate | ¹H-NMR (DMSO-d₆) δ: 7.87 (dd, 1H, J = 7.6, 1.7 Hz), 7.37-7.21 (m, 2H), 6.54 (dd, 1H, J = 18.2, 5.0 Hz), 6.00 (d, 1H, J = 4.6 Hz), 5.78 (d, 1H, J = 7.9 Hz), 5.06-4.77 (m, 5H), 4.37-4.26 (m, 1H), 4.19-4.04 (m, 1H), 4.02-3.89 (m, 1H), 3.82-3.64 (m, 2H), 3.48-3.35 (m, 1H), 1.26 (d, 6H, J = 7.3 Hz), 1.23-1.14 (m, 12H). | 568 | 1.00 |
| 16-2-3 | | ((2R,3S,4S,5R)-5-(4-amino-2-oxopyrimidin-1(2H)-yl)-4-fluoro-3-hydroxytetrahydrothiophen-2-yl)methyl N,N'-bis((1S)-1-tert-butoxycarbonylethan-1-yl)phosphorodiamidate | ¹H-NMR (CD₃OD) δ: 8.09 (dd, 1H, J = 7.3, 2.0 Hz), 6.67 (dd, 1H, J = 19.2, 4.6 Hz), 5.93 (d, 1H, J = 7.3 Hz), 5.10-4.84 (m, 1H), 4.49-4.39 (m, 1H), 4.28-4.05 (m, 2H), 3.88-3.70 (m, 2H), 3.60-3.49 (m, 1H), 1.48 (s, 18H), 1.40-1.32 (m, 6H). | 596 | 1.19 |
| 16-2-4 | | ((2R,3S,4S,5R)-5-(4-amino-2-oxopyrimidin-1(2H)-yl)-4-fluoro-3-hydroxytetrahydrothiophen-2-yl)methyl N,N'-dibenzylphosphorodiamidate | ¹H-NMR (CD₃OD) δ: 8.01 (dd, 1H, J = 7.6, 1.7 Hz), 7.39-7.17 (m, 10H), 6.62 (dd, 1H, J = 18.5, 4.6 Hz), 5.86 (d, 1H, J = 7.6 Hz), 5.07-4.85 (m, 1H), 4.41-4.31 (m, 1H), 4.16-3.95 (m, 6H), 3.49-3.39 (m, 1H). | 520 | 1.02 |

Example 17

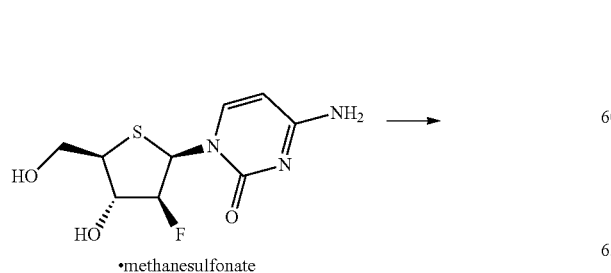

·methanesulfonate

-continued

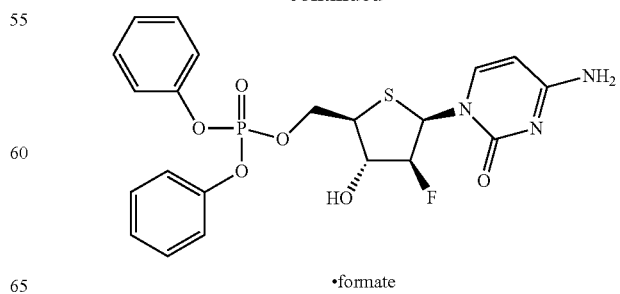

·formate

N,N-dimethylaminopyridine (1.7 mg) was added to a mixture of methanesulfonate (50.0 mg) of 4-amino-1-((2R,3S,4S,5R)-3-fluoro-4-hydroxy-5-(hydroxymethyl)tetrahydrothiophen-2-yl)pyrimidin-2(1H)-one, diphenyl chlorophosphate (35 μL) and pyridine (1.0 mL). After stirring at room temperature for 1 hour, diphenyl chlorophosphate (35 μL) was added to the reaction liquid which was then stirred at room temperature for 2 hours. Methanol (35 μL) was added to the reaction liquid which was then purified by silica gel column chromatography (ethyl acetate:methanol=90:10 to 81:19) to give a white solid. The resulting white solid was purified by reverse phase preparative HPLC (0.1% aqueous formic acid solution-0.1% formic acid acetonitrile solution) to give a formate (2.0 mg) of ((2R,3S,4S,5R)-5-(4-amino-2-oxopyrimidin-1(2H)-yl)-4-fluoro-3-hydroxytetrahydrothiophen-2-yl)methyl diphenyl phosphate as a white solid.

¹H-NMR (CDCl₃) δ: 8.12 (s, 1H), 7.89-7.71 (m, 1H), 7.39-7.10 (m, 12H), 7.06-6.93 (m, 1H), 6.68-6.49 (m, 1H), 5.94-5.77 (m, 1H), 5.19-4.88 (m, 1H), 4.50-4.22 (m, 3H), 3.72-3.59 (m, 1H).

MS (ESI m/z): 494 (M+H)
RT (min): 1.08

Example 18

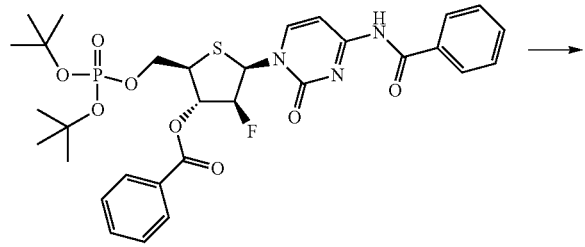

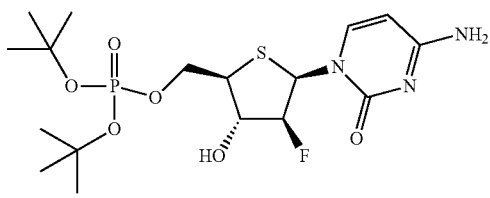

A 28% sodium methoxide/methanol solution (15.0 mL) was added to a suspension of (2R,3S,4S,5R)-5-(4-benzamido-2-oxopyrimidin-1(2H)-yl)-2-(((di-tert-butoxyphosphoryl)oxy) methyl)-4-fluorotetrahydrothiophen-3-yl benzoate (50.0 mg) in methanol (1.0 mL) which was then stirred at room temperature for 1.5 hours. Acetic acid (30 μL) was added to the reaction liquid, and the solvent was distilled off under reduced pressure. The resulting residue was purified by silica gel column chromatography (ethyl acetate:methanol=100:0 to 70:30) to give ((2R,3S,4S,5R)-5-(4-amino-2-oxopyrimidin-1(2H)-yl)-4-fluoro-3-hydroxytetrahydrothiophen-2-yl)methyl di-tert-butyl phosphate (28.8 mg) as a white solid.

¹H-NMR (DMSO-d₆) δ: 7.92-7.87 (m, 1H), 7.33-7.21 (m, 2H), 6.53 (dd, 1H, J=17.1, 5.1 Hz), 6.06 (d, 1H, J=4.8 Hz), 5.78 (d, 1H, J=7.2 Hz), 5.08-4.86 (m, 1H), 4.36-4.25 (m, 1H), 4.25-4.14 (m, 1H), 4.10-3.98 (m, 1H), 3.48-3.38 (m, 1H), 1.43 (s, 18H).

MS (ESI m/z): 454 (M+H)
RT (min): 0.93

Example 19-1

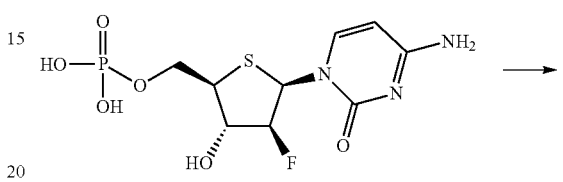

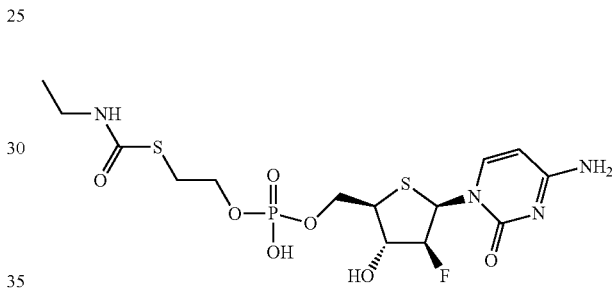

A mixture of ((2R,3S,4S,5R)-5-(4-amino-2-oxopyrimidin-1(2H)-yl)-4-fluoro-3-hydroxytetrahydrothiophen-2-yl) methyl dihydrogen phosphate (100 mg), 2-((ethylcarbamoyl)thio)ethyl 4-methylbenzene sulfonate (445 mg), N,N-diisopropylethylamine (250 μL) and N,N-dimethylformamide (1.0 mL) was stirred at 80° C. for 6 hours. The solvent was distilled off under reduced pressure and the resulting residue was purified by silica gel column chromatography (chloroform:methanol=86:14 to 39:61) to give S-(2-(((((2R,3S,4S,5R)-5-(4-amino-2-oxopyrimidin-1(2H)-yl)-4-fluoro-3-hydroxytetrahydrothiophen-2-yl)methoxy)(hydroxy)phosphoryl)oxy)ethyl) ethylcarbamothioate (2.9 mg) as a colorless oil.

¹H-NMR (CD₃OD) δ: 8.30 (d, 1H, J=7.3 Hz), 6.56 (dd, 1H, J=13.2, 5.3 Hz), 5.98 (d, 1H, J=7.9 Hz), 5.11-4.87 (m, 1H), 4.49-4.38 (m, 1H), 4.19-4.07 (m, 2H), 4.04-3.91 (m, 2H), 3.57-3.41 (m, 1H), 3.27-3.07 (m, 4H), 1.10 (t, 3H, J=7.3 Hz).

MS (ESI m/z): 473 (M+H)
RT (min): 0.56

Example 19-2

Compounds of Table 17 were obtained in the same manner as in Example 19-1.

TABLE 17

| Example No. | R | Compound name | ¹H-NMR | MS (ESI m/z) (M + H) | RT (min) |
|---|---|---|---|---|---|
| 19-2-1 | (isopropylcarbamothioate group) | S-(2-(((((2R,3S,4S,5R)-5-(4-amino-2-oxo-pyrimidin-1(2H)-yl)-4-fluoro-3-hydroxytetra-hydrothiophen-2-yl) methoxy)(hydroxy) phosphoryl)oxy)ethyl) isopropylcarbamothioate | ¹H-NMR (CD₃OD) δ: 8.31 (dd, 1H, J = 7.9, 1.3 Hz), 6.55 (dd, 1H, J = 12.6, 5.3 Hz), 5.98 (d, 1H, J = 7.9 Hz), 5.10-4.88 (m, 1H), 4.48-4.33 (m, 1H), 4.18-4.06 (m, 2H), 4.03-3.88 (m, 3H), 3.51-3.41 (m, 1H), 3.11 (t, 2H, J = 6.9 Hz), 1.12 (d, 6H, J = 6.0 Hz). | 487 | 0.63 |
| 19-2-2 | (cyclohexylcarbamothioate group) | S-(2-(((((2R,3S,4S,5R)-5-(4-amino-2-oxo-pyrimidin-1(2H)-yl)-4-fluoro-3-hydroxytetra-hydrothiophen-2-yl) methoxy)(hydroxy) phosphoryl)oxy)ethyl) cyclohexyl-carbamothioate | ¹H-NMR (CD₃OD) δ: 8.31 (dd, 1H, (J = 7.3, 1.3 Hz), 6.55 (dd, 1H, J = 13.2, 5.3 Hz), 5.98 (d, 1H, J = 7.3 Hz), 5.11-4.90 (m, 1H), 4.49-4.37 (m, 1H), 4.17-4.05 (m, 2H), 4.03-3.91 (m, 2H), 3.78-3.51 (m, 1H), 3.50-3.40 (m, 1H), 3.11 (t, 2H, J = 6.9 Hz), 1.94-1.52 (m, 4H), 1.44-1.06 (m, 6H). | 527 | 0.83 |

Example 20-1

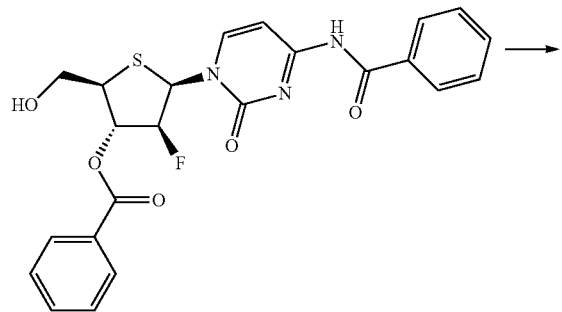

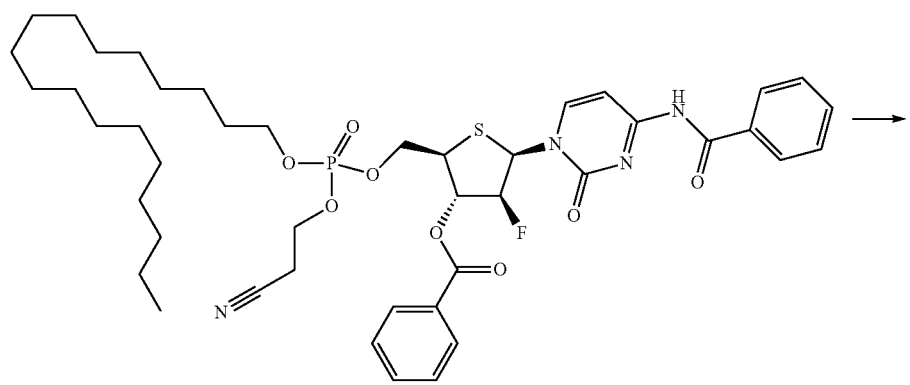

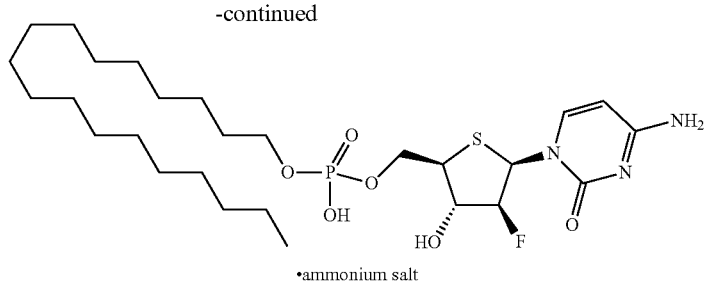

·ammonium salt

First Step

A mixture of (2R,3S,4S,5R)-5-(4-benzamido-2-oxopyrimidin-1(2H)-yl)-4-fluoro-2-(hydroxymethyl)tetrahydrothiophen-3-yl benzoate (100 mg), 2-cyanoethyl octadecyl diisopropylphosphoramidite (314 mg), 1H-tetrazole (100 mg) and methylene chloride (4.0 mL) was stirred at room temperature for 5 hours. After standing for 14.5 hours, meta-chloroperbenzoic acid (60.0 mg) was added thereto at −78° C., followed by elevation of the temperature to −10° C. over 1.5 hours and stirring for 1 hour. Water was added to the reaction liquid which was then extracted with methylene chloride, and the organic layer was washed with an aqueous saturated sodium hydrogen carbonate solution, a 10% aqueous sodium bisulfite solution and water and then dried over anhydrous sodium sulfate. The solvent was distilled off under reduced pressure and the resulting residue was purified by silica gel column chromatography (hexane:ethyl acetate=57:43 to 0:100) to give (2R,3S,4S,5R)-5-(4-benzamido-2-oxopyrimidin-1(2H)-yl)-2-((((RS)-(2-cyanoethoxy)(octadecyloxy)phosphoryl)oxy)methyl)-4-fluorotetrahydrothiophen-3-yl benzoate (41.0 mg) as a colorless oil.

MS (ESI m/z): 855 (M+H)
RT (min): 2.64

Second Step

A mixture of (2R,3S,4S,5R)-5-(4-benzamido-2-oxopyrimidin-1(2H)-yl)-2-((((RS)-(2-cyanoethoxy)(octadecyloxy)phosphoryl)oxy)methyl)-4-fluorotetrahydrothiophen-3-yl benzoate (41.0 mg) and a 7.0 mol/L ammonia/methanol solution (4.0 mL) was stirred at room temperature for 10 hours. After standing for 12 hours, the solvent was distilled off under reduced pressure. Acetone was added to the resulting residue, and the precipitated solid was collected by filtration to give an ammonium salt (13.8 mg) of ((2R,3S,4S,5R)-5-(4-amino-2-oxopyrimidin-1(2H)-yl)-4-fluoro-3-hydroxytetrahydrothiophen-2-yl)methyl octadecyl hydrogen phosphate as a white solid.

$^1$H-NMR (DMSO-$d_6$) δ: 7.99 (d, 1H, J=7.3 Hz), 7.43-6.89 (m, 4H), 6.44 (dd, 1H, J=12.9, 5.6 Hz), 5.79 (d, 1H, J=7.3 Hz), 5.06-4.78 (m, 1H), 4.32-4.20 (m, 1H), 4.01-3.78 (m, 2H), 3.71-3.57 (m, 2H), 3.50-3.17 (m, 1H), 1.56-1.37 (m, 2H), 1.37-1.12 (m, 30H), 0.92-0.78 (m, 3H).

MS (ESI m/z): 594 (M+H)
RT (min): 2.12

Example 20-2

Compounds of Table 18 and Table 19 were obtained in the same manner as in Example 20-1.

TABLE 18

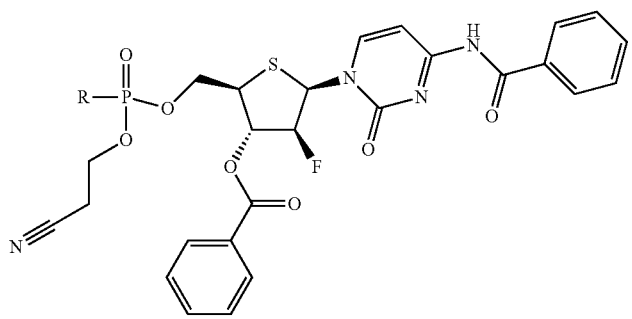

| R | Compound name | MS (ESI m/z) (M + H) | RT (min) |
|---|---|---|---|
| | (2R,3S,4S,5R)-5-(4-benzamido-2-oxopyrimidin-1(2H)-yl)-2-((((RS)-(2-cyanoethoxy)(((RS)-2-ethylhexyl)oxy)phosphoryl)oxy)methyl)-4-fluorotetrahydrothiophen-3-yl benzoate | 715 | 1.83 |

TABLE 18-continued

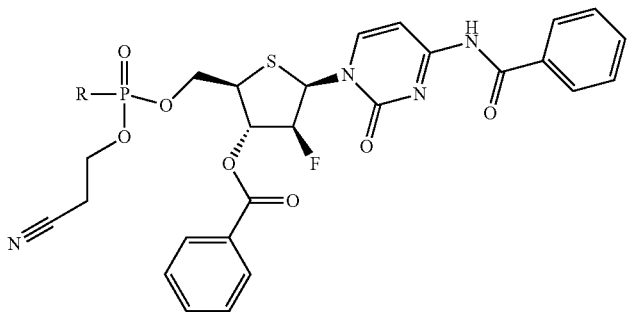

| R | Compound name | MS (ESI m/z) (M + H) | RT (min) |
|---|---|---|---|
| ![structure] dodecyloxy chain O—* | (2R,3S,4S,5R)-5-(4-benzamido-2-oxopyrimidin-1(2H)-yl)-2-((((RS)-(2-cyanoethoxy)(((RS)-2-cyanoethoxy)(dodecyloxy)phosphoryl)oxy)methyl)-4-fluorotetrahydrothiophen-3-yl benzoate | 771 | 2.20 |

TABLE 19

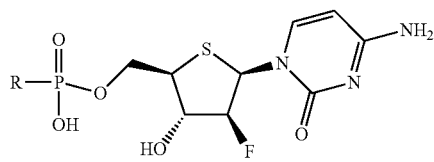

·ammonium salt

| Example No. | R | Compound name | $^1$H-NMR | MS (ESI m/z) (M + H) | RT (min) |
|---|---|---|---|---|---|
| 20-2-1 | 2-ethylhexyl O—* | ((2R,3S,4S,5R)-5-(4-amino-2-oxopyrimidin-1(2H)-yl)-4-fluoro-3-hydroxytetrahydro-thiophen-2-yl)methyl ((RS)-2-ethylhexyl) hydrogen phosphate | $^1$H-NMR (DMSO-$d_6$) δ: 7.98-7.73 (m, 1H), 7.98 (d, 1H, J = 7.3 Hz), 7.61-6.88 (m, 3H), 6.46 (dd, 1H, J = 13.9, 5.3 Hz), 5.79 (d, 1H, J = 7.3 Hz), 5.09-4.80 (m, 1H), 4.35-4.19 (m, 1H), 4.11-3.82 (m, 2H), 3.71-3.59 (m, 2H), 3.59-3.11 (m, 1H), 1.54-1.12 (m, 9H), 0.95-0.77 (m, 6H). | 454 | 0.98 |
| 20-2-2 | dodecyl O—* | ((2R,3S,4S,5R)-5-(4-amino-2-oxopyrimidin-(2H)-yl)-4-fluoro-3-hydroxytetrahydro-thiophen-2-yl)methyl dodecyl hydrogen phosphate | $^1$H-NMR (DMSO-$d_6$) δ: 7.98 (d, 1H, J = 7.6 Hz), 7.52-6.90 (m, 4H), 6.48 (dd, 1H, J = 14.5, 4.5 Hz), 5.80 (d, 1H, J = 7.6 Hz), 5.10-4.79 (m, 1H), 4.36-4.22 (m, 1H), 4.13-3.89 (m, 2H), 3.62-2.71 (m, 2H), 3.08-3.20 (m, 1H), 1.60-1.47 (m, 2H), 1.35-1.17 (m, 18H), 0.90-0.81 (m, 3H). | 510 | 1.42 |

Example 21-1

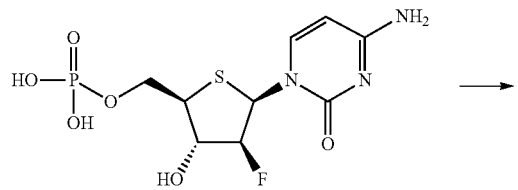

5R)-5-(4-amino-2-oxopyrimidin-1(2H)-yl)-4-fluoro-3-hydroxytetrahydrothiophen-2-yl)methoxy)(hydroxy)phosphoryl)amino)propanoate (62.3 mg) as a white solid.

$^1$H-NMR (CD$_3$OD) δ: 8.30 (d, 1H, J=7.3 Hz), 7.46-7.22 (m, 5H), 6.60-6.43 (m, 1H), 5.97 (d, 1H, J=7.3 Hz), 5.34-4.99 (m, 3H), 4.51-4.31 (m, 1H), 4.18-3.87 (m, 3H), 3.66-3.50 (m, 1H), 1.46 (d, 3H, J=6.6 Hz).

MS (ESI m/z): 503 (M+H)

RT (min): 0.79

Example 21-2

Compounds of Table 20 were obtained in the same manner as in Example 21-1.

TABLE 20

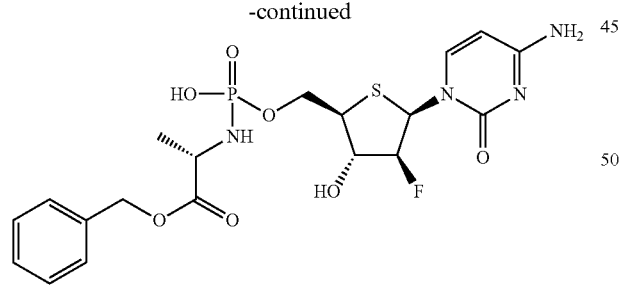

| Example No. | R | Compound name | $^1$H-NMR | MS (ESI m/z) (M + H) | RT (min) |
|---|---|---|---|---|---|
| 21-2-1 | (structure: tert-butyl alaninate) | (2S)-tert-butyl 2-(((((2R,3S,4S)5R)-5-(4-amino-2-oxopyrimidin-1(2H)-yl)-4-fluoro-3-hydroxytetrahydrothiophen-2-yl)methoxy)(hydroxy)phosphoryl)amino)propanoate | $^1$H-NMR (CD$_3$OD) δ: 8.29 (dd, 1H, J = 7.3, 1.3 Hz), 6.55 (dd, 1H, J = 13.2, 5.3 Hz), 6.98 (d, 1H, J = 7.3 Hz), 5.08-4.83 (m, 1H), 4.47-4.38 (m, 1H), 4.07-3.97 (m, 2H), 3.84-3.72 (m, 1H), 3.48-3.37 (m, 1H), 1.49-1.43 (m, 12H). | 469 | 0.74 |
| 21-2-2 | (structure: methyl alaninate) | (2S)-methyl 2-(((((2R,3S,4S,5R)-5-(4-amino-2-oxopyrimidin-1(2H)-yl)-4-fluoro-3-hydroxytetrahydrothiophen-2-yl)methoxy)(hydroxy)phosphoryl)amino)propanoate | $^1$H-NMR (CD$_3$OD) δ: 8.34-8.29 (m, 1H), 6.59-6.53 (m, 1H), 6.03 (d, 1H, J = 7.3 Hz), 5.11-4.82 (m, 1H), 4.56-4.46 (m, 1H), 4.05-3.98 (m, 2H), 3.94-3.86 (m, 1H), 3.69 (s, 3H), 3.50-3.38 (m, 1H), 1.48 (d, 3H, J = 7.3 Hz). | 427 | 0.51 |

A mixture of N,N'-dicyclohexylcarbodiimide (90.0 mg) and tert-butyl alcohol (1.0 mL) was added to a mixture of ((2R,3S,4S,5R)-5-(4-amino-2-oxopyrimidin-1(2H)-yl)-4-fluoro-3-hydroxytetrahydrothiophen-2-yl)methyl dihydrogen phosphate (100 mg), L-alanine benzyl ester hydrochloride (126 mg), triethylamine (82 μL), tert-butyl alcohol (4.0 mL) and water (1.0 mL) which was then stirred for 4 hours under heating to reflux. The solvent was distilled off under reduced pressure and the resulting residue was purified by silica gel column chromatography (ethyl acetate:methanol=50:50 to 25:75) to give (2S)-benzyl 2-(((((2R,3S,4S,

Example 22

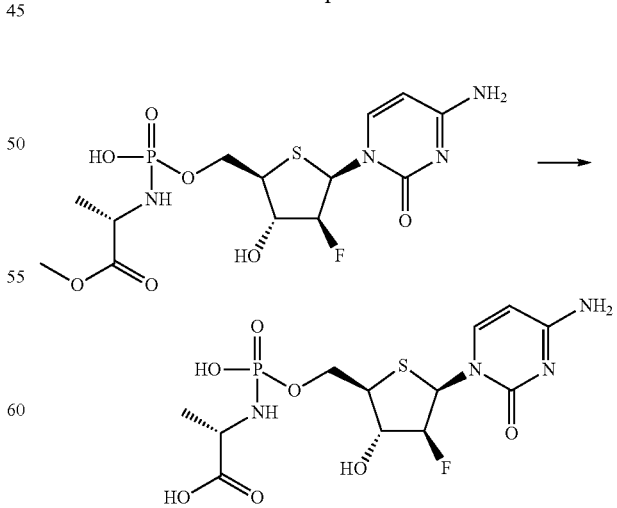

A mixture of (2S)-methyl 2-(((((2R,3S,4S,5R)-5-(4-amino-2-oxopyrimidin-1(2H)-yl)-4-fluoro-3-hydroxytetrahydrothiophen-2-yl)methoxy)(hydroxy)phosphoryl)amino)propanoate (10.0 mg), water (100 μL) and triethylamine (100 μL) was stirred at room temperature for 11.5 hours. The solvent was distilled off under reduced pressure. Acetone was added to the resulting residue, and the precipitated solid was collected by filtration to give a triethylamine salt (4.3 mg) of (2S)-2-(((((2R,3S,4S,5R)-5-(4-amino-2-oxopyrimidin-1(2H)-yl)-4-fluoro-3-hydroxytetrahydro thiophen-2-yl)methoxy)(hydroxy)phosphoryl)amino)propanoic acid as a white solid.

MS (ESI m/z): 413 (M+H)
RT (min): 0.39

Example 23-1

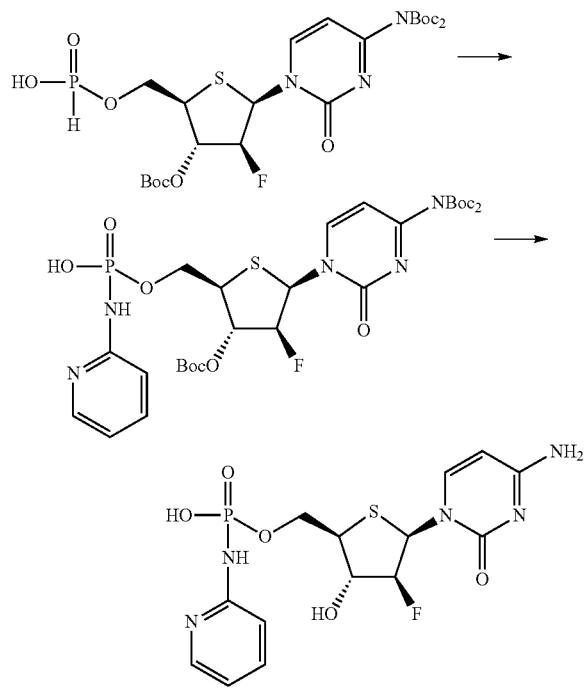

First Step

Diphenyl chlorophosphate (142 μL) was added to a mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl hydrogen phosphonate (214 mg), 2-aminopyridine (64.0 mg), pyridine (340 μL) and methylene chloride (3.4 mL) which was then stirred at room temperature for 10 minutes. A mixture of iodine (96.0 mg), pyridine (3.4 mL) and water (308 μL) was added thereto, followed by stirring at room temperature for 30 minutes. An aqueous sodium bisulfite solution was added thereto, and then the solvent was distilled off under reduced pressure. The resulting residue was purified by silica gel column chromatography (0.5% triethylaminechloroform solution:methanol=100:0 to 50:50) to give a colorless oil. The resulting colorless oil was purified by silica gel column chromatography (0.5% triethylamine/chloroform:methanol=100:0 to 70:30) to give a triethylamine salt (213 mg) of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl hydrogen (pyridin-2-yl)phosphoramidate as a colorless oil.

MS (ESI m/z): 718 (M+H)
RT (min): 1.40

Second Step

Trifluoroacetic acid (2.0 mL) was added to a mixture of ((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-2-yl)methyl hydrogen (pyridin-2-yl)phosphoramidate (213 mg) and methylene chloride (2.0 mL) which was then stirred at room temperature for 30 minutes. The solvent was distilled off under reduced pressure and the resulting residue was purified by silica gel column chromatography (0.5% triethylamine/chloroform:methanol=100:0 to 0:100) to give a triethylamine salt (29.5 mg) of ((2R,3S,4S,5R)-5-(4-amino-2-oxopyrimidin-1(2H)-yl)-4-fluoro-3-hydroxytetrahydrothiophen-2-yl)methyl hydrogen pyridin-2-ylphosphoramidate as a white solid.

$^1$H-NMR (DMSO-d$_6$) δ: 8.05-7.96 (m, 1H), 7.92-7.84 (m, 1H), 7.54-7.44 (m, 1H), 7.39-7.14 (m, 3H), 6.96-6.79 (m, 1H), 6.72-6.61 (m, 1H), 6.49-6.36 (m, 1H), 6.33-6.15 (m, 1H), 5.79-5.70 (m, 1H), 5.01-4.73 (m, 1H), 4.31-4.16 (m, 1H), 4.04-3.75 (m, 2H), 3.38-3.25 (m, 1H), 3.07-2.93 (m, 6H), 1.22-1.12 (m, 9H).

MS (ESI m/z): 418 (M+H)
RT (min): 0.31

Example 23-2

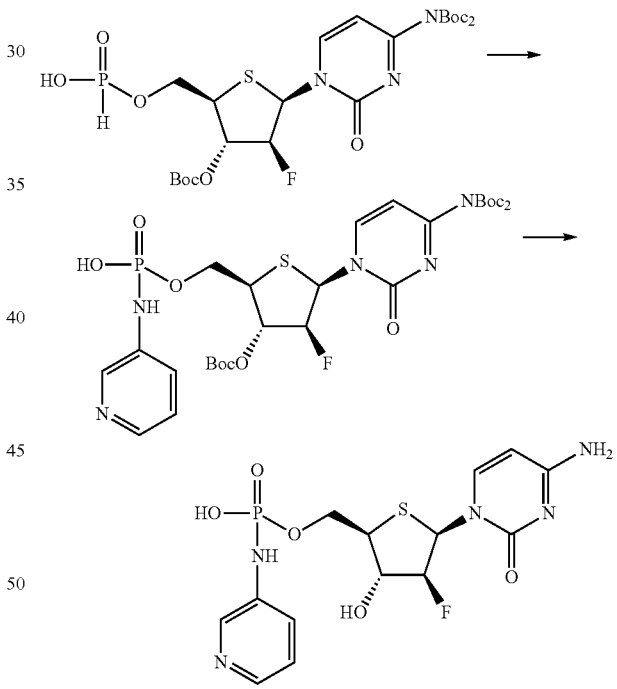

First Step

The following compound was obtained in the same manner as in the first step of Example 23-1.

((2R,3S,4S,5R)-5-(4-(bis(tert-butoxycarbonyl)amino)-2-oxopyrimidin-1(2H)-yl)-3-((tert-butoxycarbonyl)oxy)-4-fluorotetrahydrothiophen-3-yl)methyl hydrogen (pyridin-2-yl)phosphoramidate MS (ESI m/z): 718 (M+H)
RT (min): 1.29

Second Step

The following compound was obtained in the same manner as in the second step of Example 23-1.

((2R,3S,4S,5R)-5-(4-amino-2-oxopyrimidin-1(2H)-yl)-4-fluoro-3-hydroxytetrahydrothiophen-2-yl)methyl hydrogen (pyridin-3-yl)phosphoramidate ¹H-NMR (DMSO-d₆) δ: 8.29-8.22 (m, 1H), 7.90-7.84 (m, 1H), 7.82-7.78 (m, 1H), 7.47-7.40 (m, 1H), 7.34-7.14 (m, 2H), 7.05-6.99 (m, 1H), 6.79-6.71 (m, 1H), 6.48-6.35 (m, 1H), 6.34-6.23 (m, 1H), 5.80-5.71 (m, 1H), 5.05-4.75 (m, 1H), 4.29-4.15 (m, 1H), 3.96-3.73 (m, 2H), 3.31-3.24 (m, 1H), 3.12-2.91 (m, 6H), 1.24-1.09 (m, 9H).

MS (ESI m/z): 418 (M+H)

RT (min): 0.26

Example 24-1 for 10 minutes. An aqueous sodium bisulfite solution was added to the reaction liquid, and the solvent was distilled off under reduced pressure. The resulting residue was purified by silica gel column chromatography (ethyl acetate:methanol=100:0 to 90:10) to give (2R,3R,4S,5R,6R)-2-(acetoxymethyl)-6-(2-(((((2R,3S,4S,5R)-5-(4-benzamido-2-oxopyrimidin-1(2H)-yl)-3-(benzoyloxy)-4-fluorotetrahydrothiophen-2-yl)methoxy)(2-cyanoethoxy)phosphoryl)oxy)ethoxy)tetrahydro-2H-pyran-3,4,5-triyl triacetate (49.0 mg) as a colorless oil.

MS (ESI m/z): 977 (M+H)

RT (min): 1.45

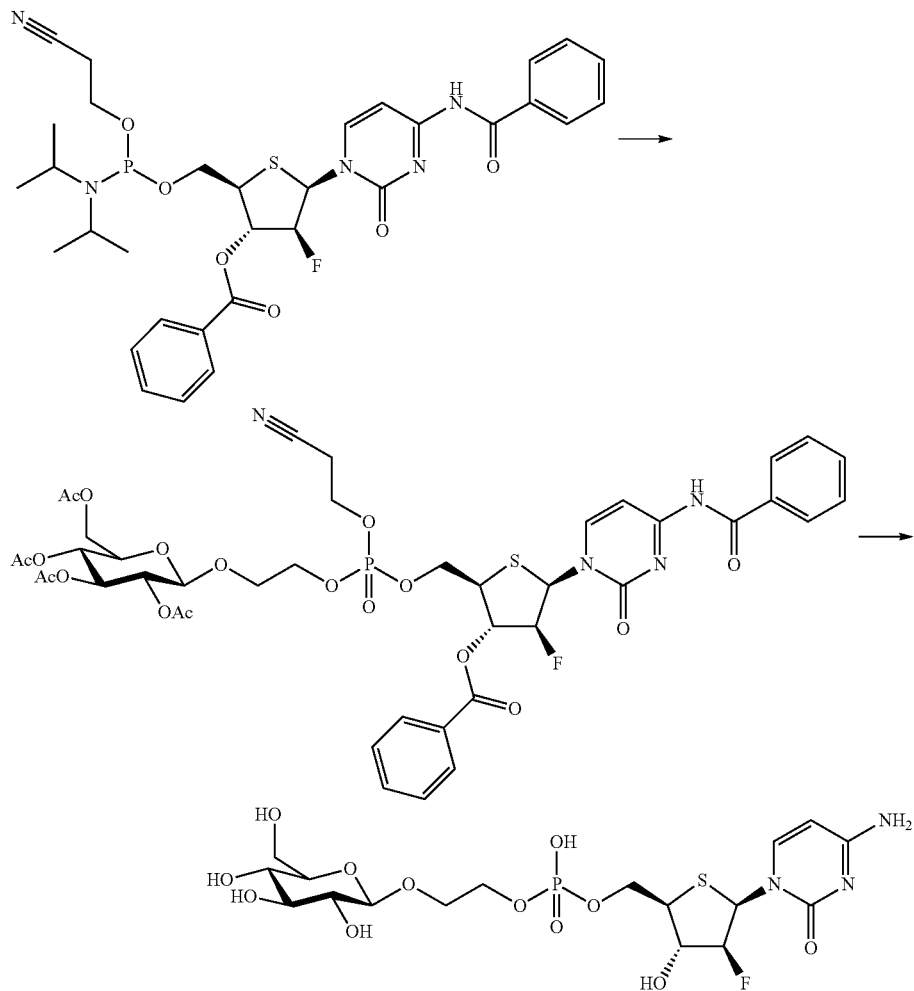

First Step 1H-tetrazole (28.0 mg) was added to a mixture of (2R,3S,4S,5R)-5-(4-benzamido-2-oxopyrimidin-1(2H)-yl)-2-((((2-cyanoethoxy)(diisopropylamino)phosphino)oxy)methyl)-4-fluorotetrahydrothiophen-3-yl benzoate (203 mg), (2R,3R,4S,5R,6R)-2-(acetoxymethyl)-6-(2-hydroxyethoxy)tetrahydro-2H-pyran-3,4,5-triyl triacetate (79.0 mg) and acetonitrile (4.0 mL) which was then stirred at room temperature for 35 minutes. 1H-tetrazole (28.0 mg) was added to the reaction liquid which was then stirred at room temperature for 5 minutes. A mixture of iodine (103 mg), pyridine (2.0 mL) and water (200 μL) was added to the reaction liquid which was then stirred at room temperature Second Step A mixture of (2R,3R,4S,5R,6R)-2-(acetoxymethyl)-6-(2-(((((2R,3S,4S,5R)-5-(4-benzamido-2-oxopyrimidin-1(2H)-yl)-3-(benzoyloxy)-4-fluorotetrahydrothiophen-2-yl)methoxy)(2-cyanoethoxy)phosphoryl)oxy)ethoxy)tetrahydro-2H-pyran-3,4,5-triyl triacetate (49.0 mg) and a 7.0 mol/L ammonia/methanol solution (3.0 mL) was stirred at room temperature for 8 hours and 40 minutes. The solvent was distilled off under reduced pressure. Water was added to the resulting residue, and the water layer was washed three times with ethyl acetate. The solvent was distilled off under reduced pressure to give an ammonium salt of ((2R,3S,4S,5R)-5-(4-amino-2-oxopyrimidin-1(2H)-yl)-4-fluoro-3-hydroxytetrahydrothiophen-2-yl)methyl (2-(((2R,3R,4S,5S,6R)-3,4,5-trihydroxy-6-(hydroxymethyl)tetrahydro-2H-pyran-2-yl)oxy) ethylhydrogen phosphate as a white solid (27.3 mg).

$^1$H-NMR (D$_2$O) δ: 8.29 (d, 1H, J=7.9 Hz), 6.34-6.28 (m, 1H), 6.01 (d, 1H, J=7.9 Hz), 5.18-4.93 (m, 1H), 4.41-4.30 (m, 2H), 4.09-3.95 (m, 5H), 3.81-3.76 (m, 2H), 3.62-3.54 (m, 1H), 3.44-3.16 (m, 5H).

MS (ESI m/z): 548 (M+H)
RT (min): 0.26

Example 24-2

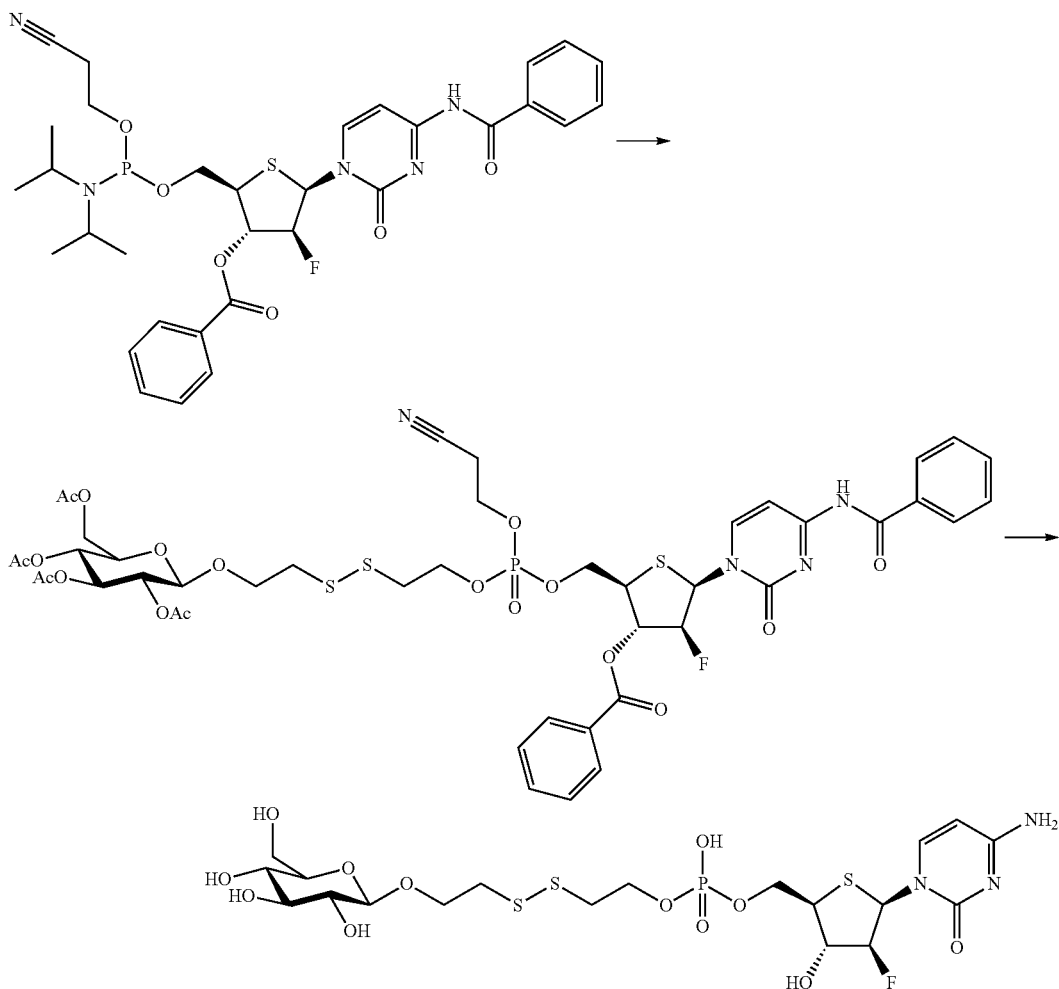

First Step 1H-tetrazole (9.5 mg) was added to a mixture of (2R,3S,4S,5R)-5-(4-benzamido-2-oxopyrimidin-1(2H)-yl)-2-((((2-cyanoethoxy)(diisopropylamino)phosphino)oxy)methyl)-4-fluorotetrahydrothiophen-3-yl benzoate (68.0 mg), (2R,3R,4S,5R,6R)-2-(acetoxymethyl)-6-(2-((2-hydroxyethyl)disulfanyl)ethoxy)tetrahydro-2H-pyran-3,4,5-triyl triacetate (33.0 mg) and acetonitrile (1.4 mL) which was then stirred at room temperature for 15 minutes. A mixture of iodine (35.0 mg), pyridine (680 μL) and water (68 μL) was added to the reaction liquid which was then stirred at room temperature for 10 minutes. The solvent was distilled off under reduced pressure and the resulting residue was purified by silica gel column chromatography (ethyl acetate:methanol=100:0 to 90:10) to give (2R,3R,4S,5R,6R)-2-(acetoxymethyl)-6-(2-((2-(((((2R,3S,4S,5R)-5-(4-benzamido-2-oxopyrimidin-1(2H)-yl)-3-(benzoyloxy)-4-fluorotetrahydrothiophen-2-yl)methoxy)(2-cyanoethoxy)phosphoryl)oxy)ethyl)disulfanyl)ethoxy)tetrahydro-2H-pyran-3,4,5-triyl triacetate (36.0 mg) as a colorless oil.

MS (ESI m/z): 1069 (M+H)
RT (min): 1.56

Second Step

A mixture of (2R,3R,4S,5R,6R)-2-(acetoxymethyl)-6-(2-((2-(((((2R,3S,4S,5R)-5-(4-benzamido-2-oxopyrimidin-1(2H)-yl)-3-(benzoyloxy)-4-fluorotetrahydrothiophen-2-yl)methoxy)(2-cyanoethoxy)phosphoryl)oxy)ethyl)disulfanyl)ethoxy)tetrahydro-2H-pyran-3,4,5-triyl triacetate (36.0 mg) and a 7.0 mol/L ammonia/methanol solution (3.0 mL) was stirred at room temperature for 8 hours and 40 minutes. The solvent was distilled off under reduced pressure. Water was added to the resulting residue, and the water layer was washed three times with ethyl acetate. The solvent was distilled off under reduced pressure and the resulting residue was purified by reverse phase preparative HPLC (0.1% aqueous formic acid solution-0.1% formic acid acetonitrile solution) to give a formate (7.6 mg) of ((2R,3S,4S,5R)-5-(4-amino-2-oxopyrimidin-1(2H)-yl)-4-fluoro-3-hydroxytetrahydrothiophen-2-yl)methyl (2-((2-(((2R,3R,4S,5S,6R)-3, 4,5-trihydroxy-6-(hydroxymethyl)tetrahydro-2H-pyran-2-yl)oxy) ethyl)disulfanyl)ethyl) hydrogen phosphate as a white solid.

$^{1}$H-NMR (D$_2$O) δ: 8.52 (d, 1H, J=7.9 Hz), 6.31-6.25 (m, 1H), 6.16 (d, 1H, J=7.9 Hz), 5.23-4.99 (m, 1H), 4.41-4.29 (m, 2H), 4.13-4.00 (m, 5H), 3.91-3.76 (m, 2H), 3.65-3.56 (m, 1H), 3.47-3.12 (m, 5H), 2.95-2.84 (m, 4H).

MS (ESI m/z): 640 (M+H)

RT (min): 0.51

Example 25

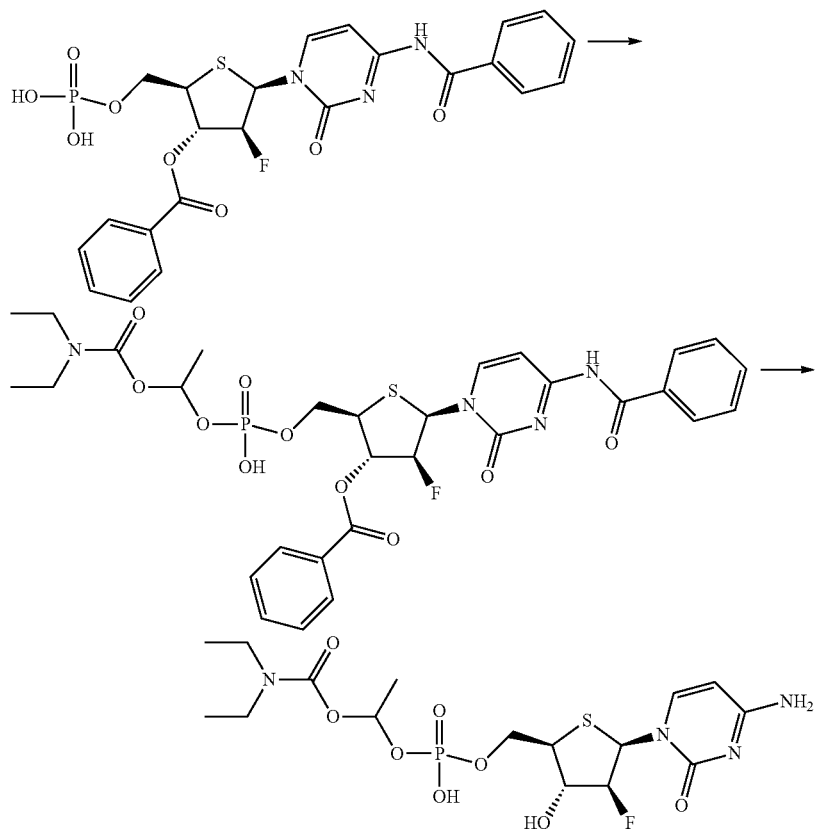

First Step

A mixture of (2R,3S,4S,5R)-5-(4-benzamido-2-oxopyrimidin-1(2H)-yl)-4-fluoro-2-((phosphonooxy)methyl) tetrahydrothiophen-3-yl benzoate (43.3 mg), 1-chloroethyl diethylcarbamate (280 mg), N,N-diisopropylethylamine (0.60 mL) and N,N-dimethylformamide (0.9 mL) was stirred at 50° C. for 3 hours. Water was added at room temperature to the reaction liquid which was then extracted with ethyl acetate. The organic layer was washed with water and an aqueous saturated sodium chloride solution, and dried over anhydrous sodium sulfate. The solvent was distilled off under reduced pressure to give (2R,3S,4S,5R)-5-(4-benzamido-2-oxopyrimidin-1(2H)-yl)-2-(((1-((diethylcarbamoyl)oxy)ethoxy)(hydroxy)phosphoryl)oxy)methyl)-4-fluorotetrahydrothiophen-3-yl benzoate.

MS (ESI m/z): 693 (M+H)

RT (min): 1.24

Second Step

A mixture of (2R,3S,4S,5R)-5-(4-benzamido-2-oxopyrimidin-1(2H)-yl)-2-((1-((diethylcarbamoyl)oxy)ethoxy)(hydroxy)phosphoryl)oxy)methyl)-4-fluorotetrahydrothiophen-3-yl benzoate obtained in the first step and a 7.0 mol/L ammonia/methanol solution (1.5 mL) was stirred at room temperature for 16.5 hours. The solvent was distilled off under reduced pressure and the resulting residue was purified by silica gel column chromatography (ethyl acetate:methanol=100:0 to 20:80) to give 1-(((((2R,3S,4S,5R)-5-(4-amino-2-oxopyrimidin-1(2H)-yl)-4-fluoro-3-hydroxytetrahydrothiophen-2-yl)methoxy)(hydroxy)phosphoryl)oxy)ethyl diethylcarbamate (21.7 mg) as a yellow solid.

$^{1}$H-NMR (CD$_3$OD) δ: 8.40-8.19 (m, 1H), 6.63-6.46 (m, 1H), 6.46-6.32 (m, 1H), 6.14-5.99 (m, 1H), 5.13-4.88 (m, 1H), 4.48-4.34 (m, 1H), 4.22-4.05 (m, 2H), 3.56-3.43 (m, 1H), 3.43-3.23 (m, 4H), 1.53 (d, 3H, J=5.3 Hz), 1.36-1.27 (m, 6H)

MS (ESI m/z): 485 (M+H)

RT (min): 0.72

Example 26-1

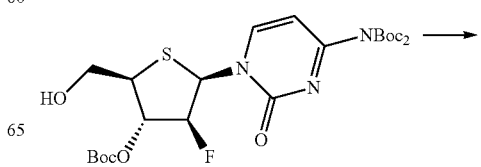

-continued

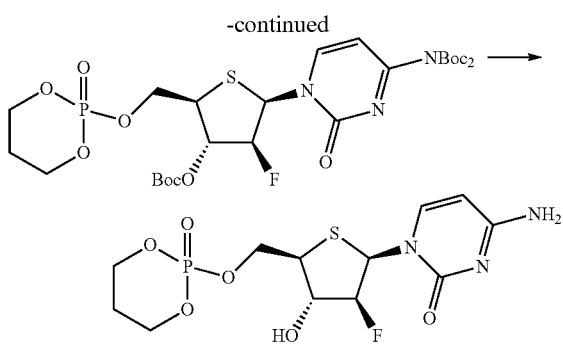

First Step

Under a nitrogen atmosphere, a 2.0 mol/L tert-butyl magnesium chloride/tetrahydrofuran solution (450 μL) was added dropwise at −78° C. to a mixture of tert-butyl tert-butoxycarbonyl(1-((2R,3S,4S,5R)-4-((tert-butoxycarbonyl)oxy)-3-fluoro-5-(hydroxymethyl)tetrahydrothiophen-2-yl)-2-oxo-1,2-dihydropyrimidin-4-yl)carbamate (168 mg) and tetrahydrofuran (17 mL) which was then stirred for 15 minutes. A mixture of 2-(4-nitrophenoxy)-1,3,2-dioxaphosphinane 2-oxide (389 mg) and tetrahydrofuran (3.0 mL) was added at −78° C. to the reaction liquid which was then stirred at room temperature for 1.5 hours. An aqueous saturated ammonium chloride solution was added to the reaction liquid which was then extracted with ethyl acetate, washed with an aqueous saturated sodium chloride solution and dried over anhydrous magnesium sulfate. The solvent was distilled off under reduced pressure and the resulting residue was purified by silica gel column chromatography (hexane:ethyl acetate=20:80 to 80:20) to give 4-(bis(tert-butoxycarbonyl)amino)-1-((2R,3S,4S,5R)-4-((tert-butoxycarbonyl)oxy)-3-fluoro-5-(((2-oxido-1,3,2-dioxaphosphinan-2-yl)oxy)methyl)tetrahydrothiophen-2-yl)pyrimidin-2(1H)-one (204 mg) as a brown oil.

MS (ESI m/z): 682 (M+H)
RT (min): 1.70

Second Step

A mixture of 4-(bis(tert-butoxycarbonyl)amino)-1-((2R,3S,4S,5R)-4-((tert-butoxycarbonyl)oxy)-3-fluoro-5-(((2-oxido-1,3,2-dioxaphosphinan-2-yl)oxy)methyl)tetrahydrothiophen-2-yl)pyrimidin-2(1H)-one (204 mg) and trifluoroacetic acid (1.0 mL) was stirred at room temperature for 1.5 hours. The solvent was distilled off under reduced pressure and the resulting residue was purified by silica gel column chromatography (ethyl acetate:methanol=100:0 to 80:20) to give 4-amino-1-((2R,3S,4S,5R)-3-fluoro-4-hydroxy-5-(((2-oxido-1,3,2-dioxaphosphinan-2-yl)oxy)methyl)tetrahydrothiophen-2-yl)pyrimidin-2(1H)-one (47.0 mg) as a white solid.

$^1$H-NMR (DMSO-$d_6$) δ: 7.90-7.88 (m, 1H), 7.34 (s, 1H), 7.28 (s, 1H), 6.59-6.53 (m, 1H), 6.12 (d, 1H, J=4.6 Hz), 5.81-5.78 (m, 1H), 5.10-4.85 (m, 1H), 4.45-4.31 (m, 6H), 4.22-4.11 (m, 1H), 3.56-3.47 (m, 1H), 2.14-1.79 (m, 2H).

MS (ESI m/z): 382 (M+H)
RT (min): 0.49

Example 26-2

Compounds of Table 21 and Table 22 were obtained in the same manner as in Example 26-1.

TABLE 21

| R | Compound name | MS (ESI m/z) (M + H) | RT (min) |
|---|---|---|---|
| (phenyl-substituted dioxaphosphinane) | 4-(bis(tert-butoxycarbonyl])amino)-1-((2R,3S,4S,5R)-4-((tert-butoxycarbonyl)oxy)-3-fluoro-5-((((1RS,4R)-2-oxido-4-phenyl-1,3,2-dioxaphosphinan-2-yl)oxy)methyl)tetrahydrothiophen-2-yl)pyrimidin-2(1H)-one | 758 | 1.83 |
| (3-chlorophenyl-substituted dioxaphosphinane) | 4-(bis(tert-butoxycarbonyl)amino)-1-((2R,3S,4S,5R)-5-((((1RS,4RS)-4-(3-chlorophenyl)-2-oxido-1,3,2-dioxaphosphinan-2-yl)oxy)methyl)-4-((tert-butoxycarbonyl)oxy)-3-fluorotetrahydrothiophen-2-yl)pyrimidin-2(1H)-one | 792 | 1.92 |
| (benzo-fused dioxaphosphinine) | 4-(bis(tert-butoxycarbonyl)amino)-1-((2R,3S,4S,5R)-4-((tert-butoxycarbonyl)oxy)-3-fluoro-5-((((RS)-2-oxido-4H-benzo[d][1,3,2]dioxaphosphinin-2-yl)oxy)methyl)tetrahydrothiophen-2-yl)pyrimidin-2(1H)-one | 730 | 1.87 |

TABLE 21-continued

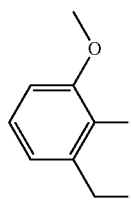

| R | Compound name | MS (ESI m/z) (M + H) | RT (min) |
|---|---|---|---|
| ![methoxybenzodioxaphosphinine] | 4-(bis(tert-butoxycarbonyl)amino)-1-((2R,3S,4S,5R)-4-((tert-butoxycarbonyl)oxy)-3-fluoro-5-((((RS)-8-methoxy-2-oxido-4H-benzo[d][1,3,2]dioxaphosphinin-2-yl)oxy)methyl)tetrahydrothiophen-2-yl)pyrimidin-2(1H)-one | 760 | 1.85 |

TABLE 22

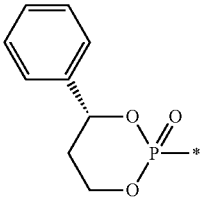

| Example No. | R | Compound name | $^1$H-NMR | MS (ESI m/z) (M + H) | RT (min) |
|---|---|---|---|---|---|
| 26-2-1 | phenyl-dioxaphosphinane | 4-amino-1-((2R,3S,4S,5R)-3-fluoro-4-hydroxy-5-((((2RS,4R)-2-oxido-4-phenyl-1,3,2-dioxaphosphinan-2-yl)oxy)methyl)tetrahydrothiophen-2-yl)pyrimidin-2(1H)-one | $^1$H-NMR (DMSO-d$_6$) δ: 8.11 (d, 1H, J = 8.1 Hz), 7.45-7.38 (m, 6H), 7.33-7.23 (m, 2H), 6.47-6.33 (m, 1H), 6.06-6.01 (m, 1H), 5.91 (d, 1H, J = 8.1 Hz), 5.11-4.91 (m, 1H), 4.31-4.26 (m, 1H), 4.18-4.16 (m, 1H), 4.05-3.85 (m, 3H), 3.17-3.09 (m, 1H), 2.42-2.36 (m, 1H), 2.28-2.15 (m, 1H), 1.91-1.85 (m, 1H). | 458 | 0.99 |
| 26-2-2 | 3-chlorophenyl-dioxaphosphinane | 4-amino-1-((2R,3S,4S,5R)-5-((((2RS,4RS)-4-(3-chlorophenyl)-2-oxido-1,3,2-dioxaphosphinan-2-yl)oxy)methyl)-3-fluoro-4-hydroxy-tetrahydrothiophen-2-yl)pyrimidin-2(1H)-one | $^1$H-NMR (DMSO-d$_6$) δ: 7.92-7.84 (m, 1H), 7.53-7.38 (m, 4H), 7.31 (m, 1H), 7.25 (s, 1H), 6.56 (dd, 1H, J = 18.0, 4.8 Hz), 6.12 (d, 1H, J = 4.6 Hz), 5.76-5.73 (m, 2H), 5.07-4.87 (m, 1H), 4.63-4.17 (m, 6H), 3.51-3.48 (m, 1H), 2.31-2.12 (m, 2H). | 492 | 0.93 |
| 26-2-3 | benzodioxaphosphinine | 4-amino-1-((2R,3S,4S,5R)-3-fluoro-4-hydroxy-5-((((RS)-2-oxido-4H-benzo[d][1,3,2]dioxaphosphinin-2-yl)oxy)methyl)tetrahydrothiophen-2-yl)pyrimidin-2(1H)-one | $^1$H-NMR (DMSO-d$_6$) δ: 7.83-7.70 (m, 1H), 7.43-7.13 (m, 6H), 6.54-6.51 (m, 1H), 6.11 (d, 1H, J = 4.0 Hz), 5.73 (t, 1H, J = 7.9 Hz), 5.57-5.50 (m, 2H), 5.00-4.90 (m, 1H), 4.50-4.28 (m, 3H), 3.52-3.48 (m, 1H). | 430 | 0.78 |
| 26-2-4 | 8-methoxybenzodioxaphosphinine | 4-amino-1-((2R,3S,4S,5R)-3-fluoro-4-hydroxy-5-((((RS)-8-methoxy-2-oxido-4H-benzo[d][1,3,2]dioxaphosphinin-2-yl)oxy)methyl)tetrahydrothiophen-2-yl)pyrimidin-2(1H)-one | $^1$H-NMR (DMSO-d$_6$) δ: 7.96-7.91 (m, 2H), 7.66 (s, 1H), 7.19-7.07 (m, 2H), 6.83 (d, 1H, J = 5.6 Hz), 6.51-6.45 (m, 1H), 6.14-6.13 (m, 1H), 5.93 (t, 1H, J = 6.8 Hz), 6.53-6.46 (m, 2H), 5.12-4.88 (m, 1H), 4.54-4.41 (m, 1H), 4.34-4.19 (m, 2H), 3.84 (s, 3H), 3.64-3.46 (m, 1H). | 460 | 0.78 |

Example 27

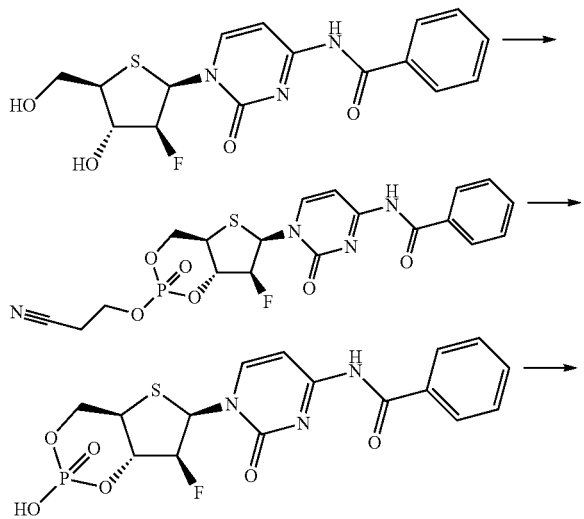

First Step

A mixture of N-(1-((2R,3S,4S,5R)-3-fluoro-4-hydroxy-5-(hydroxymethyl)tetrahydrothiophen-2-yl)-2-oxo-1,2-dihydropyrimidin-4-yl)benzamide (920 mg), 2-cyanoethyl N,N,N',N'-tetraisopropylphosphorodiamidite (800 mg), 1H-tetrazole (530 mg) and methylene chloride (10.0 mL) was stirred at room temperature for 1 hour and 20 minutes. A mixture of meta-chloroperbenzoic acid (618 mg) and methylene chloride (10.0 mL) was added at −40° C. to the reaction liquid which was then stirred for 2 hours. An aqueous saturated sodium hydrogen carbonate solution and a 10% aqueous sodium bisulfite solution were added to the reaction liquid which was then extracted with methylene chloride. The organic layer was washed with water and an aqueous saturated sodium chloride solution, and then dried over anhydrous sodium sulfate. The solvent was distilled off under reduced pressure. A mixture of hexane and ethyl acetate (=1/1) was added to the resulting residue, and the precipitated solid was collected by filtration to give N-(1-((2RS,4aR,6R,7S,7aS)-2-(2-cyanoethoxy)-7-fluoro-2-oxidotetrahydro-4H-thieno[3,2-d][1,3,2]dioxaphosphinin-6-yl)-2-oxo-1,2-dihydropyrimidin-4-yl)benzamide (580 mg) as a white solid.

MS (ESI m/z): 481 (M+H)
RT (min): 1.02, 1.05

Second Step

A mixture of N-(1-((2RS,4aR,6R,7S,7aS)-2-(2-cyanoethoxy)-7-fluoro-2-oxidotetrahydro-4H-thieno[3,2-d][1,3,2]dioxaphosphinin-6-yl)-2-oxo-1,2-dihydropyrimidin-4-yl)benzamide (580 mg) and a 7.0 mol/L ammonia/methanol solution (10.0 mL) was stirred at room temperature for 1 hour. The solvent was distilled off under reduced pressure. Ethyl acetate was added to the resulting residue, and the precipitated solid was collected by filtration to give N-(1-((4aR,6R,7S,7aS)-7-fluoro-2-hydroxy-2-oxidotetrahydro-4H-thieno[3,2-d][1,3,2]dioxaphosphinin-6-yl)-2-oxo-1,2-dihydropyrimidin-4-yl)benzamide (467 mg) as a pale yellow solid.

MS (ESI m/z): 428 (M+H)
RT (min): 0.74

Third Step

A mixture of N-(1-((4aR,6R,7S,7aS)-7-fluoro-2-hydroxy-2-oxidotetrahydro-4H-thieno[3,2-d][1,3,2]dioxaphosphinin-6-yl)-2-oxo-1,2-dihydropyrimidin-4-yl)benzamide (350 mg) and 7.0 mol/L ammonia/methanol solution (4.0 mL) was stirred at 40° C. for 4 hours. The solvent was distilled off under reduced pressure. Ethyl acetate was added to the resulting residue, and the precipitated solid was collected by filtration to give 4-amino-1-((4aR,6R,7S,7aS)-7-fluoro-2-hydroxy-2-oxidotetrahydro-4H-thieno[3,2-d][1,3,2]dioxaphosphinin-6-yl)pyrimidin-2(1H)-one (265 mg) as a pale yellow solid.

$^1$H-NMR (CD$_3$OD) δ: 8.05 (d, 1H, J=7.9 Hz), 6.72-6.60 (m, 1H), 5.98 (d, 1H, J=7.9 Hz), 5.33-5.04 (m, 1H), 4.83-4.65 (m, 1H), 4.41-4.21 (m, 2H), 3.57-3.39 (m, 1H).

MS (ESI m/z): 324 (M+H)
RT (min): 0.21, 0.26

Example 28

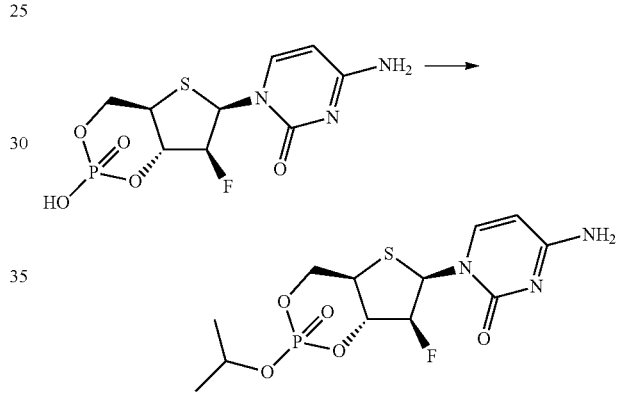

Oxalyl chloride (20 μL) was added under ice-cooling to a mixture of 4-amino-1-((4aR,6R,7S,7aS)-7-fluoro-2-hydroxy-2-oxidotetrahydro-4H-thieno[3,2-d][1,3,2]dioxaphosphinin-6-yl)pyrimidin-2(1H)-one (20.0 mg), trimethyl phosphate (1.0 mL), N,N-dimethylformamide (10 μL) and methylene chloride (1.0 mL) which was then stirred for 40 minutes. Isopropyl alcohol (2.0 mL) was added to the reaction liquid which was then stirred at room temperature for 3 hours and 40 minutes and allowed to stand for 12 hours. The solvent was distilled off under reduced pressure. Methylene chloride was added to the resulting residue, and the insoluble matter was separated by filtration. The solvent was distilled off under reduced pressure. Water was added to the resulting residue which was then extracted with methylene chloride and dried over anhydrous sodium sulfate. The solvent was distilled off under reduced pressure. Diisopropyl ether was added to the resulting residue, and the precipitated solid was collected by filtration to give 4-amino-1-((2RS,4aR,6R,7S,7aS)-7-fluoro-2-isopropoxy-2-oxidotetrahydro-4H-thieno[3,2-d][1,3,2]dioxaphosphinin-6-yl)pyrimidin-2(1H)-one (3.4 mg) as a pale yellow solid.

$^1$H-NMR (CD$_3$OD) δ: 8.08-8.02 (m, 1H), 6.75-6.68 (m, 1H), 5.97 (d, 1H, J=7.3 Hz), 5.47-5.19 (m, 1H), 5.14-4.99 (m, 1H), 4.82-4.70 (m, 1H), 4.70-4.56 (m, 2H), 3.84-3.71 (m, 1H), 1.37 (d, 6H, J=5.9 Hz).

MS (ESI m/z): 366 (M+H)
RT (min): 0.71

Example 29-1

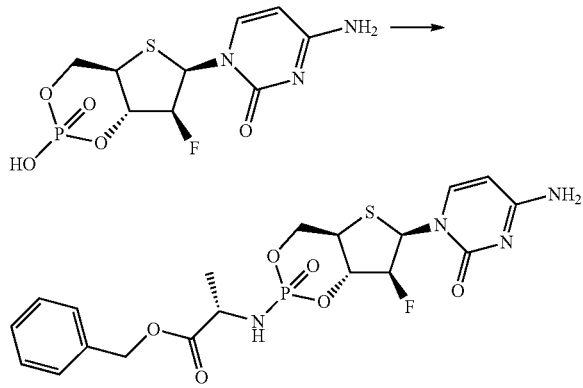

Oxalyl chloride (40 μL) was added under ice-cooling to a mixture of 4-amino-1-((4aR,6R,7S,7aS)-7-fluoro-2-hydroxy-2-oxidotetrahydro-4H-thieno[3,2-d][1,3,2]dioxaphosphinin-6-yl)pyrimidin-2(1H)-one (20.0 mg), trimethyl phosphate (1.0 mL), N,N-dimethylformamide (10 μL) and methylene chloride (1.0 mL) which was then stirred at room temperature for 1 hour and 20 minutes. The reaction liquid was added under ice-cooling to a mixture of L-alanine benzyl ester hydrochloride (20.0 mg), N,N-diisopropylethylamine (200 μL) and methylene chloride (2.0 mL), followed by stirring at room temperature for 2 hours and 40 minutes. Water was added to the reaction liquid which was then extracted with methylene chloride and dried over anhydrous sodium sulfate. The solvent was distilled off under reduced pressure. Diisopropyl ether was added to the resulting residue, and the precipitated solid was collected by filtration to give (2S)-benzyl 2-(((2RS,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)amino)propanoate (6.7 mg) as a pale brown solid.

$^1$H-NMR (CD$_3$OD) δ: 8.07-8.01 (m, 1H), 7.41-7.30 (m, 5H), 6.73-6.66 (m, 1H), 5.97 (d, 1H, J=7.3 Hz), 5.40-5.11 (m, 3H), 5.02-4.91 (m, 1H), 4.63-4.47 (m, 2H), 4.04-3.89 (m, 1H), 3.65-3.50 (m, 1H), 1.39 (d, 3H, J=5.9 Hz).

MS (ESI m/z): 485 (M+H)

RT (min): 1.00

Example 29-2

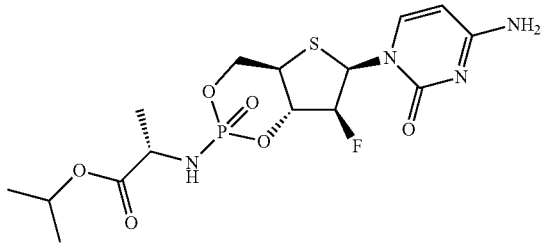

The following compound was obtained in the same manner as in Example 29-1.

(2S)-isopropyl 2-(((2RS,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)amino)propanoate $^1$H-NMR (CD$_3$OD) δ: 8.05 (d, 1H, J=7.6 Hz), 6.74-6.67 (m, 1H), 5.97 (d, 1H, J=7.6 Hz), 5.42-5.15 (m, 1H), 5.06-4.91 (m, 2H), 4.65-4.52 (m, 2H), 3.95-3.81 (m, 1H), 3.70-3.56 (m, 1H), 1.41-1.32 (m, 3H), 1.32-1.20 (m, 6H).

MS (ESI m/z): 437 (M+H)

RT (min): 0.81

Comparative Example 1

The following compound was obtained in accordance with the method described in Journal of Medicinal Chemistry, Vol. 52, pp 1531 to 1542, 2014.

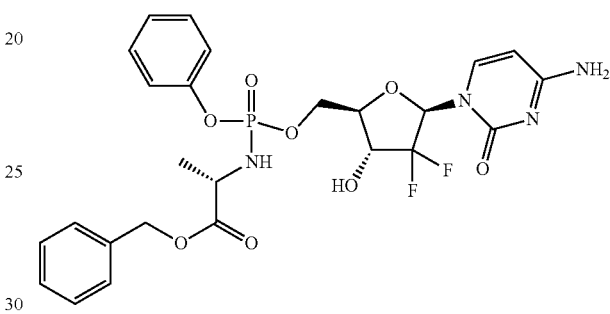

(2S)-benzyl 2-(((RS)-(((2R,3R,5R)-5-(4-amino-2-oxopyrimidin-1(2H)-yl)-4,4-difluoro-3-hydroxytetrahydrofuran-2-yl)methoxy)(phenoxy)phosphoryl)amino)propanoate $^1$H-NMR (CD$_3$OD) δ: 7.57-7.45 (m, 1H), 7.39-7.26 (m, 6H), 7.26-7.14 (m, 3H), 6.28-6.17 (m, 1H), 5.89-5.78 (m, 1H), 5.19-5.07 (m, 2H), 4.50-4.38 (m, 1H), 4.38-4.26 (m, 1H), 4.26-4.10 (m, 1H), 4.10-3.94 (m, 2H), 1.39-1.32 (m, 3H).

MS (ESI m/z): 581 (M+H)

RT (min): 1.14

Comparative Example 2

The following compound was obtained in accordance with the method described in Nucleosides, Nucleotides & Nucleic Acids, Vol. 24, Nos. 10 to 12, pp 1635 to 1649, 2005.

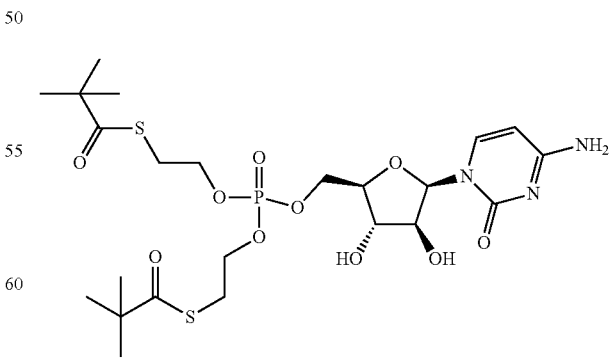

((2R,3S,4S,5R)-5-(4-amino-2-oxopyrimidin-1(2H)-yl)-3,4-dihydroxytetrahydrofuran-2-yl)methyl bis(S-pivaloyl-2-mercaptoethan-1-yl) phosphate ¹H-NMR (CD₃OD) δ: 7.81 (d, 1H, J=7.3 Hz), 6.26-6.20 (m, 1H), 5.88 (d, 1H, J=7.3 Hz), 4.46-4.23 (m, 2H), 4.21-4.07 (m, 6H), 4.04-3.99 (m, 1H), 3.22-3.09 (m, 4H), 1.26-1.18 (m, 18H).

MS (ESI m/z): 612 (M+H)

RT (min): 1.31

Comparative Example 3

The following compound was obtained in accordance with the method described in Bioorganic & Medicinal Chemistry, Vol. 17, No. 17, pp 6340 to 6347, 2009.

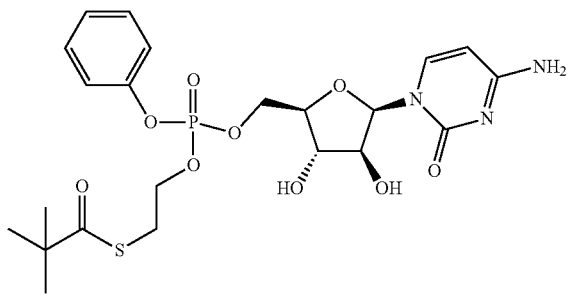 [SMILES: CC(C)(C)C(=O)SCCOP(=O)(OC[C@H]1O[C@@H](n2ccc(N)nc2=O)[C@@H](O)[C@@H]1O)Oc1ccccc1]

S-(2-(((RS)-(((2R,3S,4S,5R)-5-(4-amino-2-oxopyrimidin-1(2H)-yl)-3,4-dihydroxytetrahydrofuran-2-yl)methoxy)(phenoxy)phosphoryl)oxy)ethyl) 2,2-dimethylpropanethioate ¹H-NMR (CD₃OD) δ: 7.82-7.68 (m, 1H), 7.45-7.32 (m, 2H), 7.28-7.18 (m, 3H), 6.27-6.19 (m, 1H), 5.84-5.73 (m, 1H), 4.58-4.30 (m, 2H), 4.29-4.08 (m, 4H), 4.06-3.99 (m, 1H), 3.23-3.12 (m, 2H), 1.23-1.18 (m, 9H).

MS (ESI m/z): 544 (M+H)

RT (min): 1.16

Comparative Example 4

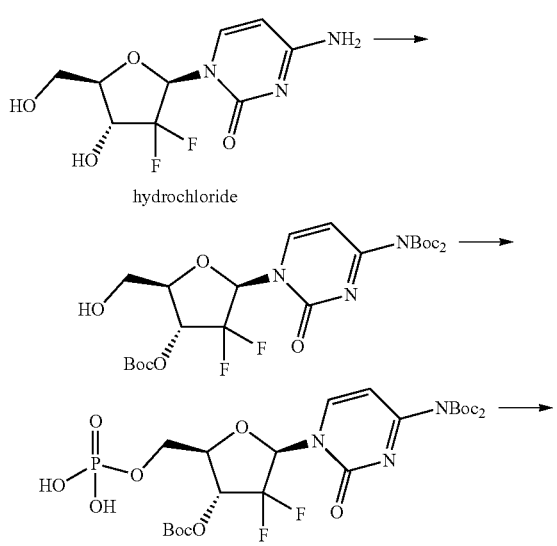

-continued

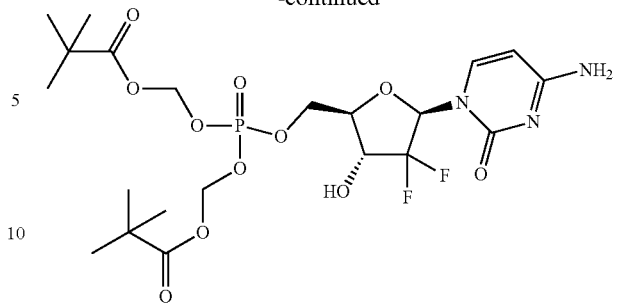

First Step

The following compound was obtained in the same manner as in Reference Example 1.

tert-Butyl tert-butoxycarbonyl(1-((2R,4S,5R)-4-((tert-butoxycarbonyl)oxy)-3,3-difluoro-5-(hydroxymethyl)-tetrahydrofuran-2-yl)-2-oxo-1,2-dihydropyrimidin-4-yl)carbamate MS (ESI m/z): 564 (M+H)

RT (min): 1.72

Second Step

The following compound was obtained in the same manner as in the second step of Example 11.

((2R,3S,5R)-5-(4-(bis(tert-butoxycarbonyl)amino)-2-oxopyrimidin-1(2H)-yl)-3-((tert-butoxycarbonyl)oxy)-4,4-difluorotetrahydrofuran-2-yl)methyl dihydrogen phosphate MS (ESI m/z): 644 (M+H)

RT (min): 1.35

Third Step

The following compound was obtained in the same manner as in the first step of Example 11.

((2R,3S,5R)-5-(4-amino-2-oxopyrimidin-1(2H)-yl)-4,4-difluoro-3-hydroxytetrahydro furan-2-yl)methyl bis(pivaloyloxymethyl) phosphate ¹H-NMR (CD₃OD) δ: 7.61 (d, 1H, J=7.9 Hz), 6.31-6.21 (m, 1H), 5.95 (d, 1H, J=7.9 Hz), 5.73-5.63 (m, 4H), 4.53-4.32 (m, 1H), 4.30-4.14 (m, 1H), 4.13-4.03 (m, 1H), 1.26-1.18 (m, 18H).

MS (ESI m/z): 572 (M+H)

RT (min): 1.20

Test Example

Gemcitabine-Resistant Cell Growth Inhibition Test

The gemcitabine-resistant strain of pancreatic cancer cell line Capan-1 (ATCC Number: HTB-79) was constructed in accordance with the method described in Neoplasia, Vol. 12, pp 807-817, 2010 and subjected to a cell growth inhibition test of the present invention compounds and the Comparative Example compounds. The cell growth inhibition test was carried out in accordance with the method described below.

For the purpose of measuring compound-induced growth inhibition, the total cell count was quantified based on the total cellular ATP concentration using a CellTiter Glo (Promega Corporation) reagent using a firefly luciferase. The Capan-1 was suspended in an IMDM medium (Life Technologies, Inc.) containing penicillin/streptomycin (penn/strep) and 20% FBS and adjusted to a cell density of 33333 cells/mL. 90 μL (3000 cells)/well of the cell suspension was seeded onto a 96-well plate (Corning, Inc.).

The cells were subjected to whole culture under standard cell growth conditions (37° C., 5% CO₂) for 24 hours. 10 μL of a serial dilution of compounds or 0.1% DMSO (solvent control) was added to the cells which were then cultured to proliferate under standard cell growth conditions (37° C., 5% CO$_2$) for 72 hours. For the purpose of measuring the total cell growth, in accordance with the instructions of the CellTiter Glo, an equal volume of the CellTiter Glo reaction liquid was added to each well and then luminescence counts (relative light unit, RLU) were quantified. An IC$_{50}$ value for growth inhibition corresponds to a compound liquid concentration causing 50% inhibition of total cell growth in a DMSO solvent control when an RLU signal exhibited by the DMSO solvent control after 72 hours of culture is defined as 0% inhibition. Each data point was obtained from duplicate samples.

The IC$_{50}$ was calculated by the following method.

The results of the test substance-treated group was plotted by taking a logarithm of a cell treatment concentration (nmol/L) on the X-axis and taking a cell growth inhibition rate (%) on the Y-axis. A straight line connecting the nearest two points with the cell growth inhibition rate Y=50(%) being therebetween was obtained, and a 50% cell growth inhibitory concentration (IC$_{50}$ value) as defined by the above straight line was calculated.

Also with respect to the results of a control substance group, the IC$_{50}$ value was determined by the same method.

IC$_{50}$ values were calculated for the triplicate test results, and an average value and a standard deviation thereof were determined. The results are shown in the following table.

Evaluation Standards
+++ 2 µmol/L>IC$_{50}$
++ 5 µmol/L>IC$_{50}$≥2 µmol/L
+ 15 µmol/L>IC$_{50}$≥5 µmol/L
− IC$_{50}$≥15 µmol/L

TABLE 23

| Example No. | Growth inhibitory activity IC$_{50}$ (µmol/L) | Example No. | Growth inhibitory activity IC$_{50}$ (µmol/L) | Comparative Example No. | Growth inhibitory activity IC$_{50}$ (µmol/L) |
|---|---|---|---|---|---|
| 1-1 | +++ | 7-1 | + | 1 | − |
| 1-2-5 | +++ | 7-3-1 | + | 2 | − |
| 2-2 | + | 7-3-2 | + | 3 | − |
| 3-1 | + | 7-3-3 | + | 4 | − |
| 3-2 | + | 8 | +++ | | |
| 4-1 | ++ | 9-1 | ++ | | |
| 4-2 | + | 9-2-1 | ++ | | |
| 5-2-1 | + | 10-1 | ++ | | |
| 5-2-2 | + | 10-2 | ++ | | |
| 5-2-3 | + | 11-1-2 | + | | |
| 5-2-4 | ++ | 11-2-2 | ++ | | |
| 5-2-5 | ++ | 12-1 | + | | |
| 5-2-6 | + | 12-2-4 | +++ | | |
| 5-2-7 | + | 13-1 | ++ | | |
| 5-2-8 | + | 13-2-1 | ++ | | |
| 5-2-9 | + | 13-2-2 | + | | |
| 6-1 | + | 14-1 | ++ | | |
| 6-2-1 | + | 14-2 | + | | |
| 6-2-2 | + | 26-2-3 | ++ | | |
| 6-2-3 | + | 26-2-4 | + | | |
| 6-2-4 | + | 29-1 | ++ | | |
| | | 29-2 | ++ | | |

The compounds of the present invention had an excellent cell growth inhibitory activity against gemcitabine-resistant strains of tumor cells.

INDUSTRIAL APPLICABILITY

The thionucleoside derivative or the salt thereof of the present invention has an excellent growth inhibitory activity against tumor cells and is useful as a tumor treatment agent.

Further, the thionucleoside derivative or the salt thereof of the present invention has an excellent growth inhibitory activity against a tumor cell which has acquired resistance to gemcitabine and is useful as a tumor treatment agent against a tumor which has acquired resistance to gemcitabine.

What is claimed is:
1. A thionucleoside derivative represented by General Formula [1]:

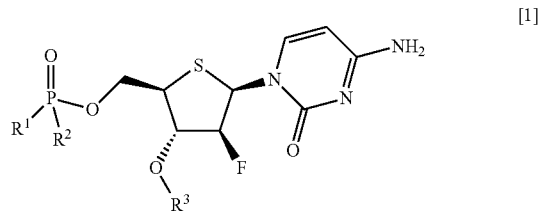

in the formula,
R$^1$ represents a hydroxyl group which may be protected, a C$_{1-20}$ alkoxy group which may be substituted, a C$_{3-8}$ cycloalkoxy group which may be substituted, an aryloxy group which may be substituted, a heterocyclic oxy group which may be substituted, or an amino group which may be substituted;

R$^2$ represents a C$_{1-20}$ alkoxy group which may be substituted, a C$_{3-8}$ cycloalkoxy group which may be substituted, an aryloxy group which may be substituted, a heterocyclic oxy group which may be substituted, or an amino group which may be substituted; or R$^1$ and R$^2$, together with the phosphorus atom to which they are bonded, may form a 5- to 10-membered nitrogen.phosphorus-containing heterocyclic ring which may be substituted, a 5- to 10-membered oxygen.phosphorus-containing heterocyclic ring which may be substituted, or a 5- to 10-membered nitrogen.oxygen.phosphorus-containing heterocyclic ring; and R$^3$ represents a hydrogen atom; or R$^2$ and R$^3$, together with the phosphorus atom to which R$^2$ is bonded, an oxygen atom, methylene, two carbon atoms constituting the tetrahydrothiophene ring and the oxygen atom to which R$^3$ is bonded, may form a 6 to 10-membered oxygen.phosphorus-containing heterocyclic ring which may be substituted; or a salt thereof.

2. The thionucleoside derivative according to claim 1, wherein R$^1$ is a hydroxyl group which may be protected, a C$_{1-6}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or an amino group which may be substituted with one or more substituents selected from Substituent group A; or the salt thereof;

Substituent group A:
A halogen atom; a hydroxyl group which may be protected; a cyano group; a nitro group; a carbamoyl group; an oxo group; a C$_{1-6}$ alkyl group which may be substituted with one or more substituents selected from Substituent group B; a C$_{1-6}$ alkyldisulfanyl group which may be substituted with one or more substituents selected from Substituent group B; a C$_{2-6}$ alkenyl group which may be substituted with one or more substituents selected from Substituent group B; a C$_{2-6}$ alkynyl group which may be substituted with one or more substituents selected from Substituent group B; a C$_{3-8}$ cycloalkyl group which may be substituted with one or more substituents selected from Substituent group B; a C$_{3-8}$ cycloalkyldisulfanyl group which may be substituted with one or more substituents selected from Substituent group B; a C$_{1-6}$ alkoxy group which may be substituted with one or more substituents selected from Substituent group B; a C$_{1-6}$ alkoxycarbonyloxy group which may be substituted with one or more substituents selected from Substituent group B; a C$_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B;

Substituent group B:

A halogen atom; a hydroxyl group; a cyano group; a nitro group; a carboxyl group; a carbamoyl group; a hydroxymethyl group; a C$_{1-6}$ alkyl group; a C$_{2-6}$ alkenyl group; a C$_{2-6}$ alkynyl group; a C$_{3-8}$ cycloalkyl group; a C$_{1-6}$ alkoxy group; a C$_{1-6}$ alkoxycarbonyl group; a C$_{3-8}$ cycloalkoxycarbonyl group; an ar-C$_{1-6}$ alkoxycarbonyl group; an aryl group; an aryloxy group; a heterocyclic oxy group which may be substituted with one or more substituents selected from a hydroxyl group and a hydroxymethyl group; an ar-C$_{1-6}$ alkoxy group; and an acyloxy group.

3. The thionucleoside derivative according to claim 1, wherein R$^2$ is a C$_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A; or the salt thereof.

4. The thionucleoside derivative according to claim 2, wherein R$^2$ is a C$_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A; or the salt thereof.

5. The thionucleoside derivative according to claim 1, wherein R$^1$ is a hydroxyl group which may be protected, a C$_{1-6}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or an amino group which may be substituted with one or more substituents selected from Substituent group A; and R$^2$ is a C$_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A; or the salt thereof.

6. The thionucleoside derivative according to claim 3, wherein R$^1$ is a hydroxyl group which may be protected, a C$_{1-6}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or an amino group which may be substituted with one or more substituents selected from Substituent group A; and R$^2$ is a C$_{1-6}$ alkoxy group which may be substituted with one or more substituents selected from Substituent group A, an aryloxy group which may be substituted with one or more substituents selected from Substituent group A, or an amino group which may be substituted with one or more substituents selected from Substituent group A; or the salt thereof.

7. The thionucleoside derivative according to claim 1, wherein R$^1$ is an aryloxy group which may be substituted with one or more substituents selected from Substituent group A, and R$^2$ is an amino group which may be substituted with one or more substituents selected from Substituent group A, or R$^1$ is a C$_{1-6}$ alkoxy group which may be substituted with one or more substituents selected from Substituent group A, and R$^2$ is a C$_{1-6}$ alkoxy group which may be substituted with one or more substituents selected from Substituent group A; or the salt thereof.

8. The thionucleoside derivative according to claim 3, wherein R$^1$ is an aryloxy group which may be substituted with one or more substituents selected from Substituent group A, and R$^2$ is an amino group which may be substituted with one or more substituents selected from Substituent group A, or R$^1$ is a C$_{1-6}$ alkoxy group which may be substituted with one or more substituents selected from Substituent group A, and R$^2$ is a C$_{1-6}$ alkoxy group which may be substituted with one or more substituents selected from Substituent group A; or the salt thereof.

9. The thionucleoside derivative according to claim 1, wherein the thionucleoside derivative is a compound selected from:
  (2S)-benzyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino) propanoate,
  (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-chlorophenoxy)phosphoryl) amino)propanoate,
  (2S)-cyclobutyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl) amino)propanoate,
  (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-bromophenoxy)phosphoryl) amino)propanoate,
  (2S)-methyl 2-(((RS)-(((2R,3S,4S,5R)-5-(4-amino-2-oxopyrimidin-1(2H)-yl)-4-fluoro-3-hydroxytetrahydrothiophen-2-yl)methoxy)(4-iodophenoxy)phosphoryl) amino)propanoate, ((2R,3S,4S,5R)-5-(4-amino-2-oxopyrimidin-1(2H)-yl)-4-fluoro-3-hydroxytetrahydrothiophen-2-yl)methyl bis (S-pivaloyl-2-mercaptoethan-1-yl) phosphate, ((2R,3S,4S,5R)-5-(4-amino-2-oxopyrimidin-1(2H)-yl)-4-fluoro-3-hydroxytetrahydrothiophen-2-yl)methyl bis (S-isobutyryl-2-mercaptoethan-1-yl) phosphate, ((2R,3S,4S,5R)-5-(4-amino-2-oxopyrimidin-1(2H)-yl)-4-fluoro-3-hydroxytetrahydrothiophen-2-yl)methyl bis (S-propionyl-2-mercaptoethan-1-yl) phosphate, (((RS)-(((2R,3S,4S,5R)-5-(4-amino-2-oxopyrimidin-1(2H)-yl)-4-fluoro-3-hydroxytetrahydrothiophen-2-yl)methoxy)(2-(pivaloylthio)ethoxy)phosphoryl)oxy) methyl pivalate, S-(2-(((RS)-(((2R,3S,4S,5R)-5-(4-amino-2-oxopyrimidin-1(2H)-yl)-4-fluoro-3-hydroxytetrahydrothiophen-2-yl)methoxy)(((isopropoxycarbonyl)oxy)methoxy) phosphoryl)oxy)ethyl) 2,2-dimethylpropanethioate, ((2R,3S,4S,5R)-5-(4-amino-2-oxopyrimidin-1(2H)-yl)-4-fluoro-3-hydroxytetrahydrothiophen-2-yl)methyl bis (pivaloyloxymethyl) phosphate, ((2R,3S,4S,5R)-5-(4-amino-2-oxopyrimidin-1(2H)-yl)-4-fluoro-3-hydroxytetrahydrothiophen-2-yl)methyl bis (2-((2-(benzyloxy)ethyl)disulfanyl)ethyl) phosphate, ((2R,3S,4S,5R)-5-(4-amino-2-oxopyrimidin-1(2H)-yl)-4-fluoro-3-hydroxytetrahydrothiophen-2-yl)methyl bis (2-((2-pivaloyloxyethyl)disulfanyl)ethyl) phosphate, ((2R,3S,4S,5R)-5-(4-amino-2-oxopyrimidin-1(2H)-yl)-4-fluoro-3-hydroxytetrahydrothiophen-2-yl)methyl bis (2-((2-isobutyroyloxyethyl)disulfanyl)ethyl) phosphate, S-(2-(((RS)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)oxy)ethyl) 2,2-dimethylpropanethioate, 4-amino-1-((2R,3S,4S,5R)-3-fluoro-4-hydroxy-5-((((RS)-2-oxido-4H-benzo[d][1,3,2]dioxaphosphinin-2-yl)oxy)methyl)tetrahydrothiophen-2-yl)pyrimidin-2(1H)-one, (2S)-benzyl 2-(((2RS,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)amino)propanoate, and (2S)-isopropyl 2-(((2RS,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)amino) propanoate; or the salt thereof.

10. A pharmaceutical composition comprising the thionucleoside derivative or the salt thereof according to claim 1.

11. A pharmaceutical composition comprising the thionucleoside derivative or the salt thereof according to claim 9.

12. The pharmaceutical composition according to claim 10 which comprises a pharmacologically acceptable additive in conjunction with the thionucleoside derivative represented by the General Formula [1] or a salt thereof.

13. The pharmaceutical composition according to claim 11 which comprises a pharmacologically acceptable additive in conjunction with the thionucleoside derivative represented by the General Formula [1] or a salt thereof.

14. A method for the treatment of pancreatic cancer, comprising a step of administering a therapeutically effective amount of the thionucleotide derivative or a salt thereof according to claim 9 to a subject in need of such a treatment.

15. A method for use of the pharmaceutical composition of claim 10 in the treatment of pancreatic cancer, which comprises a step of administering a therapeutically effective amount of the pharmaceutical composition of claim 10 to a subject in need of such a treatment.

16. A method for use of the pharmaceutical composition of claim 11 in the treatment of pancreatic cancer, which comprises a step of administering a therapeutically effective amount of the pharmaceutical composition of claim 11 to a subject in need of such a treatment.

* * * * *